US010597662B2

(12) United States Patent
Hara et al.

(10) Patent No.: US 10,597,662 B2
(45) Date of Patent: Mar. 24, 2020

(54) TRANSFORMANT AND PROCESS FOR PRODUCTION THEREOF, AND PROCESS FOR PRODUCTION OF LACTIC ACID

(71) Applicant: JMTC Enzyme Corporation, Tokyo (JP)

(72) Inventors: Futoshi Hara, Tokyo (JP); Shuichiro Kimura, Tokyo (JP); Yuichiro Hagiya, Tokyo (JP); Takayuki Tanaka, Tokyo (JP)

(73) Assignee: JMTC Enzyme Corporation, Tokyo (JP)

( * ) Notice: Subject to any disclaimer, the term of this patent is extended or adjusted under 35 U.S.C. 154(b) by 792 days.

(21) Appl. No.: 15/037,877

(22) PCT Filed: Nov. 21, 2014

(86) PCT No.: PCT/JP2014/080982
§ 371 (c)(1),
(2) Date: May 19, 2016

(87) PCT Pub. No.: WO2015/076393
PCT Pub. Date: May 28, 2015

(65) Prior Publication Data
US 2019/0153453 A1 May 23, 2019

(30) Foreign Application Priority Data

Nov. 22, 2013 (JP) .................... 2013-242236

(51) Int. Cl.
| C12N 9/04 | (2006.01) |
| C12P 7/56 | (2006.01) |
| C12N 1/20 | (2006.01) |
| C12N 15/00 | (2006.01) |
| C12N 1/14 | (2006.01) |
| C07H 21/04 | (2006.01) |
| C12N 15/52 | (2006.01) |
| C12N 9/88 | (2006.01) |
| C12N 15/81 | (2006.01) |

(52) U.S. Cl.
CPC .......... *C12N 15/52* (2013.01); *C12N 9/0006* (2013.01); *C12N 9/88* (2013.01); *C12N 15/81* (2013.01); *C12P 7/56* (2013.01); *C12N 15/815* (2013.01); *C12Y 101/01028* (2013.01); *C12Y 401/01001* (2013.01)

(58) Field of Classification Search
None
See application file for complete search history.

(56) References Cited

U.S. PATENT DOCUMENTS

| 9,284,561 B2 * | 3/2016 | Hara | ................ | C12N 9/0006 |
| 9,428,777 B2 * | 8/2016 | Hara | ................ | C12N 1/16 |
| 2005/0112737 A1 * | 5/2005 | Liu | ................ | C12N 1/18 435/139 |
| 2007/0031950 A1 * | 2/2007 | Winkler | ................ | C12N 9/0006 435/139 |
| 2011/0136192 A1 * | 6/2011 | Paul | ................ | C12N 9/0006 435/160 |
| 2012/0214214 A1 * | 8/2012 | Hara | ................ | C12N 9/0006 435/139 |

FOREIGN PATENT DOCUMENTS

| JP | 2003505065 A | 2/2003 |
| JP | 2003274958 A | 9/2003 |
| JP | 2003535583 A | 12/2003 |
| JP | 2005102625 A | 4/2005 |
| JP | 2007512018 A | 5/2007 |
| JP | 2007530007 A | 11/2007 |
| JP | 2008092862 A | 4/2008 |
| JP | 2009537144 A | 10/2009 |
| WO | 03049525 A2 | 6/2003 |
| WO | 2007032792 A2 | 3/2007 |
| WO | 2011021629 A1 | 2/2011 |
| WO | 2012074818 A2 | 6/2012 |
| WO | 2012114979 A1 | 8/2012 |
| WO | WO-2014030655 A1 * | 2/2014 ............... C12N 1/16 |

OTHER PUBLICATIONS

Fukao. C4TGIO. UniProtKB database. 2009.*
Akada et al, Sets of Integrating Plasmids and Gene Disruption Cassettes Containing Improved Counter-Selection Markers Designed for Repeated Use in Budding, Yeast, 2002, vol. 19, p. 393-402.
Japanese Office Action, Office Action issued in JP 2014-236022 dated Jun. 19, 2018, 9 pages.
European Patent Office, Search Report issued in corresponding European Patent Application No. 14864444.6 dated Mar. 21, 2017, 10 pages.
Arndt, GM, et al., Gene regulation by antisense RNA in the fission yeast Schizosaccharomyces pombe, Mol Gen Genet, 1995, 248 (3), 293-300.
P40370 ver 110, UniProt/Swiss-Prot, Nov. 13, 2013, Schizosaccharomyces pombe (strain 972/ATCC24843) gene eno101.
Q8NKC2 ver 83, UniProt/Swiss-Prot, Nov. 13, 2013, Schizosaccharomyces pombe (strain 972/ATCC 24843) gene eno102.

(Continued)

*Primary Examiner* — Yong D Pak
(74) *Attorney, Agent, or Firm* — Wood Herron & Evans LLP

(57) ABSTRACT

The present invention relates to a transformant which uses *Schizosaccharomyces pombe* as a host into which a D-LDH gene derived from bacteria of the genus *Pediococcus* and a D-LDH gene derived from bacteria of the genus *Lactobacillus* are incorporated and in which some of the genes in a group of pyruvate decarboxylase-encoding genes of the *Schizosaccharomyces pombe* host have been deleted or inactivated.

10 Claims, 6 Drawing Sheets
Specification includes a Sequence Listing.

(56) References Cited

OTHER PUBLICATIONS

P36580 ver 98, UniProt/Swiss-Prot, Nov. 13, 2013, Schizosaccharomyces pombe (strain 972/ATCC 24843) gene fba1.
O43026 ver 106, UniProt/Swiss-Prot, Nov. 13, 2013, Schizosaccharomyces pombe (strain 972/ATCC 24843) gene gpd3.
P36623 ver 122, UniProt/Swiss-Prot, Nov. 13, 2013, Schizosaccharomyces pombe (strain 972/ATCC 24843) gene gpm1.
P09988 ver 124, UniProt/Swiss-Prot, Nov. 13, 2013, Schizosaccharomyces pombe (strain 972/ATCC 24843) gene hht2.
O60101 ver 94, UniProt/Swiss-Prot, Nov. 13, 2013, Schizosaccharomyces pombe (strain 972/ATCC 24843) gene pgk1.
P07669 ver 113, UniProt/Swiss-Prot, Nov. 13, 2013, Schizosaccharomyces pombe (strain 972/ATCC 24843) gene tpi1.
P0CG72 ver 23, UniProt/Swiss-Prot, Nov. 13, 2013, Schizosaccharomyces pombe (strain 972/ATCC 24843) gene ubi4.
P78958 ver 113, UniProt/Swiss-Prot, Nov. 13, 2013, Schizosaccharomyces pombe (strain 972/ATCC 24843) gene gpd1.
Japanese Patent Office, Office Action issued in JP 2014-236021 dated Aug. 7, 2018, 10 pages.
Wanmeng, Mu, et al., "Characterization of D-Lactate Dehydrogenase from Pediococcus Acidilactici that Converts Phenylpyruvic Acid into Phenyllactic Acid," Biotechnol. Lett., vol. 34, No. 5, pp. 907-911 (Jan. 20, 2012).
Xiaoqiang, Jia, et al., "D-Lactic Acid Production by a Genetically Engineered Strain Corynebacterium Glutamicum," World J. Microbiol. Biotechnol., vol. 27, No. 9, pp. 2117-2124 (Feb. 4, 2011).
Hara, Futoshi, et al., "Lactate Production Using Schizosaccharomyces Pombe," Dai 61 Kai Abstracts of the Annual Meeting of the Society for Biotechnology, Japan, 2Mp08, p. 190 (2009).
Okino, Shohei, et al., "Coryneform Saikin o Mochiita D-Nyusan no Seisan," Japan Society for Bioscience, Biotechnology and Agrochemistry Taikai Koen Yoshishu, 3A26p12, p. 267 (2008).
Japanese Patent Office, International Search Report issued in International Patent Application No. PCT/JP2014/080982 and English-language Translation dated Feb. 17, 2015.

* cited by examiner

TRANSFORMANT AND PROCESS FOR PRODUCTION THEREOF, AND PROCESS FOR PRODUCTION OF LACTIC ACID

TECHNICAL FIELD

The present invention relates to a transformant, a process for production thereof, and a process for production of lactic acid. More specifically, the present invention relates to a transformant which is obtained by incorporating a D-lactate dehydrogenase gene derived from bacteria of the genus *Pediococcus* and a D-lactate dehydrogenase gene derived from bacteria of the genus *Lactobacillus* into *Schizosaccharomyces pombe* and in which some of the genes in a group of pyruvate decarboxylase-encoding genes have been deleted or inactivated, a process for production of the transformant, and a process for production of lactic acid in which the transformant is cultured or fermented in a culture solution or a fermentation solution and lactic acid is obtained from the culture solution or the fermentation solution.

BACKGROUND ART

Lactic acid is widely used for foods, medical purposes, and chemical raw materials of cosmetics and the like. Furthermore, polylactic acid obtained using lactic acid is drawing attention as a biodegradable plastic which is finally decomposed into carbon dioxide and water by microorganisms and the like. Therefore, there is a need to produce lactic acid with high productivity at low cost.

As a process for production of lactic acid, a biological process for producing lactic acid by fermenting sugar with lactic acid bacteria is known. However, because lactic acid bacteria have poor acid resistance, in order to obtain high productivity in the aforementioned process, the lactic acid produced through fermentation needs to be changed into a lactate by being neutralized by an alkali. In the production process in which neutralization is performed by an alkali, a step of reverting the lactate to lactic acid is necessary. Accordingly, the production process becomes complicated, and the production costs increase.

As a process for obtaining lactic acid without performing neutralization by an alkali, there is a process using a transformant obtained by introducing a lactate dehydrogenase-encoding gene into yeast. For example, PTL 1 discloses a case where lactic acid can be produced with high productivity without performing a neutralization step with an alkali by conducting lactic acid fermentation by using a transformant which is obtained by incorporating a lactate dehydrogenase gene derived from mammals such as human beings into *Schizosaccharomyces pombe* and in which some of the genes in a group of pyruvate decarboxylase-encoding genes of the *Schizosaccharomyces pombe* host have been deleted or inactivated. Furthermore, PTL 2 discloses a case where L-lactic acid is obtained by culturing a transformant which is obtained by introducing an L-lactate dehydrogenase gene of *Lactobacillus plantarum* into *Saccharomyces cerevisiae* which substantially does not produce ethanol when cultured in a culture medium.

CITATION LIST

Patent Literature

[PTL 1] PCT International Publication No. WO2011/021629

[PTL 2] Published Japanese Translation No. 2007-512018 of the PCT International Publication for Patent Applications

SUMMARY OF INVENTION

Technical Problem

The present invention aims to provide a transformant of *Schizosaccharomyces pombe* which can produce D-lactic acid with high productivity without requiring neutralization by an alkali, and to provide a process for production of the transformant.

The present invention also aims to provide a process for producing lactic acid with high productivity by using the transformant without performing a neutralization step with an alkali.

Solution to Problem

A transformant according to the present invention uses *Schizosaccharomyces pombe* as a host into which a D-lactate dehydrogenase gene derived from bacteria of the genus *Pediococcus* and a D-lactate dehydrogenase gene derived from bacteria of the genus *Lactobacillus* are incorporated, in which some of the genes in a group of pyruvate decarboxylase-encoding genes of the *Schizosaccharomyces pombe* host have been deleted or inactivated.

In the transformant according to the present invention, the bacteria of the genus *Pediococcus* are preferably *Pediococcus acidilactici* or *Pediococcus pentosaceus*, and the bacteria of the genus *Lactobacillus* are preferably *Lactobacillus pentosus*, *Lactobacillus bulgaricus*, or *Lactobacillus brevis*. In addition, in the transformant according to the present invention, the deleted or inactivated genes in the group of pyruvate decarboxylase-encoding genes are preferably PDC2 genes. Furthermore, the D-lactate dehydrogenase gene is preferably incorporated into a chromosome of the *Schizosaccharomyces pombe*.

A process for production of a transformant according to the present invention is a process for producing a transformant using *Schizosaccharomyces pombe* as a host into which a D-lactate dehydrogenase gene derived from bacteria of the genus *Pediococcus* and a D-lactate dehydrogenase gene derived from bacteria of the genus *Lactobacillus* are incorporated, in which some of the genes in a group of pyruvate decarboxylase-encoding genes of the *Schizosaccharomyces pombe* host have been deleted or inactivated. The process includes a step of obtaining a transformant by introducing an expression cassette into the host, in which the expression cassette consists of an expression cassette including a promoter and a terminator functioning in the *Schizosaccharomyces pombe* and a D-lactate dehydrogenase gene derived from bacteria of the genus *Pediococcus* and an expression cassette including a promoter and a terminator functioning in the *Schizosaccharomyces pombe* and a D-lactate dehydrogenase gene derived from bacteria of the genus *Lactobacillus*, or consists of an expression cassette including a promoter or a terminator functioning in the *Schizosaccharomyces pombe*, a D-lactate dehydrogenase gene derived from bacteria of the genus *Pediococcus*, and a D-lactate dehydrogenase gene derived from bacteria of the genus *Lactobacillus*, and a host, in which some of the genes in a group of pyruvate decarboxylase-encoding genes have been deleted or inactivated, is used as the aforementioned host, or some of the genes in a group of pyruvate decarboxylase-encoding genes of the transformant obtained as above are deleted or inactivated.

In the process for production of a transformant according to the present invention, the deleted or inactivated genes in a group of pyruvate decarboxylase-encoding genes are preferably PDC2 genes. In addition, the D-lactate dehydrogenase gene derived from bacteria of the genus *Pediococcus* and the D-lactate dehydrogenase gene derived from bacteria of the genus *Lactobacillus* are preferably introduced into a chromosome of the host.

In a process for production of lactic acid according to the present invention, the transformant is cultured or fermented in a culture solution or a fermentation solution, and D-lactic acid is obtained from the culture solution or the fermentation solution.

In the process for production of lactic acid according to the present invention, the culture or the fermentation is preferably performed using a culture solution or a fermentation solution containing glucose or sucrose at a concentration of 1% by mass to 50% by mass. Furthermore, it is preferable that the culture or the fermentation be further continued after the pH of the culture solution or the fermentation solution becomes equal to or less than 3.5 due to the D-lactic acid produced by the transformant. It is also preferable that the culture or the fermentation be continued without neutralizing the D-lactic acid in the culture solution or the fermentation solution that is produced by the transformant. Moreover, it is preferable that lactic acid be separated from the culture solution or the fermentation solution without neutralizing the D-lactic acid in the culture solution or the fermentation solution that is produced by the transformant. In addition, it is preferable that an initial bacterial cell concentration of the transformant in the culture solution or the fermentation solution be set to be 0.1 g/L to 50 g/L (expressed in terms of dry bacterial cells).

Advantageous Effects of Invention

The transformant of *Schizosaccharomyces pombe* according to the present invention can produce D-lactic acid with high productivity without requiring neutralization by an alkali. Furthermore, the transformant is suitable for the production of D-lactic acid in the presence of high concentrations of sugars, particularly, glucose, fructose, sucrose, or maltose, and for high-density lactic acid fermentation.

The transformant can be simply obtained by the process for production of a transformant according to the present invention.

Furthermore, the process for production of lactic acid according to the present invention can produce D-lactic acid with high productivity without a neutralization step with an alkali being performed.

DESCRIPTION OF EMBODIMENTS

[Transformant]

Figure 1:
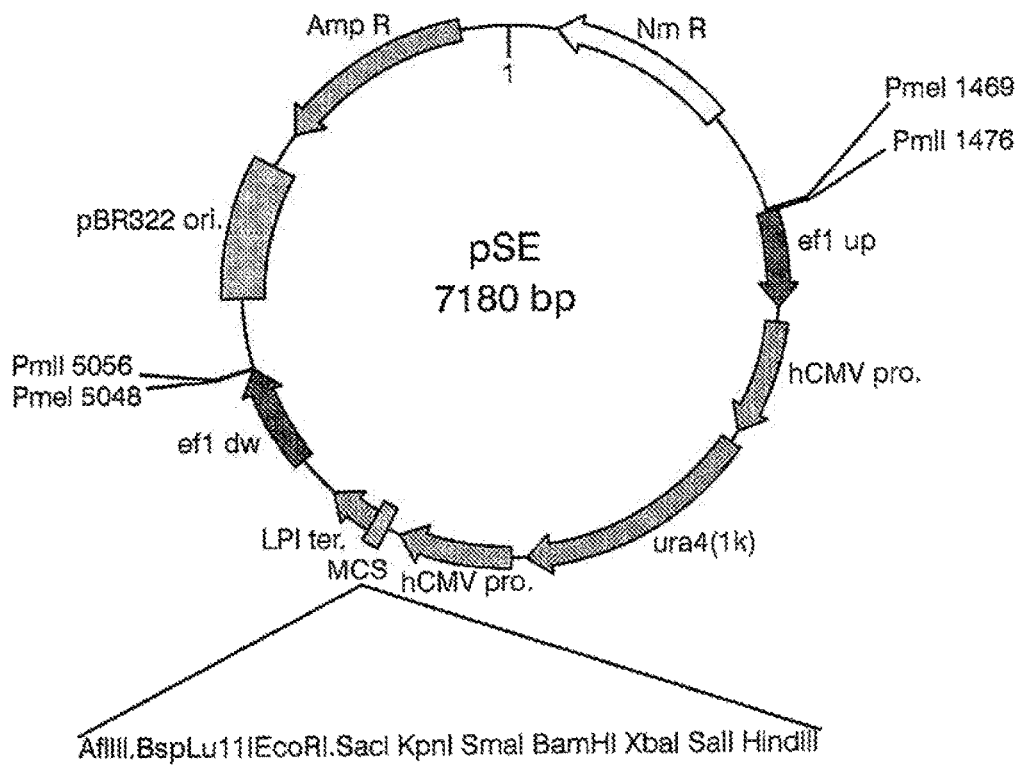
FIG. 1 is a schematic view of the structure of a recombinant vector pSE.

The transformant according to the present invention is a transformant which uses *Schizosaccharomyces pombe* (hereinafter, referred to as "*S. pombe*" as well) as a host into which a D-lactate dehydrogenase gene derived from bacteria of the genus *Pediococcus* and a D-lactate dehydrogenase gene derived from bacteria of the genus *Lactobacillus* are incorporated, in which some of the genes in a group of pyruvate decarboxylase-encoding genes of the *S. pombe* host have been deleted or inactivated.

<*S. pombe*>

The *S. pombe* as a host is yeast (fission yeast) that belongs to the genus *Schizosaccharomyces*, and is a microorganism having particularly excellent acid resistance compared to other yeasts. It is known that the *S. pombe* is excellent at producing D-lactic acid in the presence of high-concentration glucose compared to other yeasts such as *Saccharomyces cerevisiae*, and is suitable for high-density fermentation (fermentation using a large amount of yeast) as well. Therefore, by using the transformant of the *S. pombe*, D-lactic acid can be produced with extremely high productivity.

The entire base sequence of choromosomes of the *S. pombe* has been published "*Schizosaccharomyces pombe* Gene DB (http://www.genedb.org/genedb/*pombe*)" in the database "Gene DB" of the Sanger Institute. The gene sequence data of the *S. pombe* described in the present specification can be obtained by searching the gene name or the aforementioned strain name in the database described above.

In addition, the *S. pombe* is available from public or private depository institutes such as American Type Culture Collection (ATCC, Manassas, Va., USA), National Collection of Yeast Cultures (NCYC, Norwich, United Kingdom), Nite Biological Resource Center (NBRC, Kisarazu-shi, Chiba), and Yeast Genetic Resource Center (YGRC, Graduate School of Science, Osaka University).

<Pyruvate Decarboxylase-encoding Gene>

The group of pyruvate decarboxylase-encoding genes (pyruvate decarboxylase genes, hereinafter, referred to as "PDC genes" as well) in the *S. pombe* consists of 4 kinds of genes, namely, a gene encoding pyruvate decarboxylase 1 (hereinafter, referred to as a "PDC1 gene"), a gene encoding pyruvate decarboxylase 2 (hereinafter, referred to as a "PDC2 gene"), a gene encoding pyruvate decarboxylase 3 (hereinafter, referred to as a "PDC3 gene"), and a gene encoding pyruvate decarboxylase 4 (hereinafter, referred to as a "PDC4 gene"). Among these, the PDC2 gene and the PDC4 gene are PDC genes that play a key functional role in the *S. pombe*. The strain name of each of the PDC genes is as follows.

PDC1 gene (Pdc1); SPAC13A11. 06
PDC2 gene (Pdc2); SPAC1F8. 07c
PDC3 gene (Pdc3); SPAC186. 09
PDC4 gene (Pdc4); SPAC3G9. 11c The PDC gene sequence data can be obtained by searching the gene name or the strain name in the aforementioned *S. pombe* gene database.

In the wild-type *S. pombe*, glucose is metabolized into pyruvic acid by a glycolytic system, and by the pyruvate decarboxylase expressed from the PDC genes described above, the pyruvic acid is converted into acetaldehyde. Then, the acetaldehyde is converted into ethanol by alcohol dehydrogenase, and in this way, ethanol fermentation is performed. Because the wild-type *S. pombe* does not have a functioning lactate dehydrogenase gene (a gene encoding lactate dehydrogenase (LDH), hereinafter, referred to as an "LDH gene" as well), a route through which lactic acid is generated from pyruvic acid is not present in the *S. pombe*.

In contrast, LDH expressed from the incorporated LDH gene generates lactic acid by reducing pyruvic acid into lactic acid. Accordingly, simply by incorporating the LDH gene into the wild-type *S. pombe* so as to enable the production of lactic acid, both of the ethanol fermentation and the lactic acid fermentation are performed, and hence the lactic acid productivity is not sufficiently increased.

The transformant according to the present invention has a chromosome in which some of the genes in a group of pyruvate decarboxylase-encoding genes have been deleted or inactivated. Due to the deletion or inactivation of some of the genes in the group of PDC genes of the transformant, the ethanol fermentation efficiency of the transformant is reduced, and the amount of pyruvic acid to be converted into ethanol is decreased. Therefore, the lactic acid productivity is improved. Here, if the group of PDC genes is totally deleted or inactivated, ethanol fermentation is not performed at all, and the growth of the transformant is inhibited. Accordingly, only some of the genes in the group of PDC genes should be deleted or inactivated.

The PDC genes to be deleted or inactivated are particularly preferably the PDC2 genes. The PDC2 genes are PDC genes that particularly play a key functional role.

As described above, if all of the PDC genes are deleted or inactivated, the transformant does not perform ethanol fermentation, and thus the growth of the transformant is hindered. Therefore, the deletion or inactivation of the PDC genes should be performed by maintaining the ethanol fermentation ability necessary for the growth so as to obtain a sufficient amount of transformant and simultaneously by lowering the ethanol fermentation ability so as to improve the fermentation efficiency of lactic acid. In order to accomplish such a task, the inventors of the present invention conducted investigation. As a result, they found that if the PDC2 genes are deleted or inactivated, the PDC4 genes are activated to some extent, and enough ethanol fermentation ability for obtaining a sufficient amount of transformant and the production of lactic acid with high fermentation efficiency can be accomplished simultaneously.

The deletion or inactivation of the PDC genes can be performed by a known process. For example, by using a Latour method (described in the journal of Nucleic Acids Res., 2006, Vol. 34, p. e11, PCT International Publication No. WO2007/063919, and the like), the PDC genes can be deleted.

Furthermore, by introducing a mutation into a portion of the base sequence of the PDC genes by means of deletion, insertion, substitution, or addition, the PDC genes can be deleted. The mutation to be introduced may be only one of the deletion, insertion, substitution, and addition, or two or more mutations of these.

As the process for introducing the mutation into a portion of the PDC genes, a known process can be used.

For example, a mutation separation method using a mutagen ("Experimental Method of Yeast Molecular Genetics", 1996, Gakkai Shuppan Center) and a random mutation method using a polymerase chain reaction (PCR) (the journal of PCR Methods Appl., 1992, Vol. 2, pp 28-33) can be used.

The PDC genes that carry the mutation introduced into a portion thereof may be genes expressing temperature-sensitive mutant-type pyruvate decarboxylase. The temperature-sensitive mutant-type pyruvate decarboxylase is an enzyme which shows activity equivalent to the activity of wild-type pyruvate decarboxylase at a certain culture temperature but undergoes the loss or deterioration of the activity at a temperature equal to or higher than a specific culture temperature.

A mutant strain expressing the mutant-type pyruvate decarboxylase can be obtained by being selected from genes whose growth rate is equivalent to the growth rate of the wild-type yeast under the conditions in which the activity is not limited by the temperature but is greatly reduced under specific temperature conditions in which the activity is limited.

<LDH Gene>

The transformant according to the present invention has an LDH gene. As described above, the *S. pombe* does not originally have the LDH gene. Therefore, by introducing the LDH gene of a living organism other than the *S. pombe* into the *S. pombe* through a genetic engineering process, the transformant is obtained.

The transformant according to the present invention has a D-lactate dehydrogenase (D-LDH) gene derived from bacteria of the genus *Pediococcus* and a D-LDH gene derived from bacteria of the genus *Lactobacillus*. The transformant according to the present invention does not have only one D-LDH gene but has at least two or more D-LDH genes. Therefore, the expression efficiency of the D-LDH gene can be improved, and in turn the production efficiency of D-lactic acid is improved. Furthermore, because of having the D-LDH genes derived from specific microorganisms in combination, the transformant can produce a larger amount of D-lactic acid.

The D-LDH gene derived from bacteria of the genus *Pediococcus* includes a D-LDH gene (wild type) that the bacteria of the genus *Pediococcus* originally have, a mutant gene which is obtained by the substitution, insertion, or deletion of one or several bases in the D-LDH gene and encodes a protein having the D-LDH activity, a mutant gene which is obtained by the substitution, insertion, or deletion of one or several amino acid bases in D-LDH encoded by the D-LDH gene and encodes a protein having the D-LDH activity, and a gene obtained by adding a base sequence encoding other peptides and the like to the upstream or the downstream side of the aforementioned gene. The same is applied to the D-LDH gene derived from bacteria of the genus *Lactobacillus*.

Specifically, examples of bacteria of the genus *Pediococcus* or D-LDH derived from the bacteria include D-LDH of *Pediococcus acidilactici* (PaDLDH) (GenBank accession number: CAA50275. 1) and D-LDH of *Pediococcus pentosaceus* (PpDLDH) (GenBank accession number: ABJ67935. 1). Examples of D-LDH derived from bacteria of the genus *Lactobacillus* include D-LDH of *Lactobacillus pentosus* (LpDLDH) (GenBank accession number: BAA14352. 1), D-LDH gene of *Lactobacillus bulgaricus* (LbDLDH) (GenBank accession number: CAA42781. 1), and D-LDH of *Lactobacillus brevis* (LbrDLDH) (GenBank accession number: AFR11459. 1). Herein, Genbank is the database of the National Center for Biotechnology Information (NCBI).

The transformant according to the present invention has at least one D-LDH gene derived from bacteria of the genus *Pediococcus* or at least one D-LDH gene derived from bacteria of the genus *Lactobacillus*. Alternatively, the transformant according to the present invention has at least one D-LDH gene derived from bacteria of the genus *Pediococcus* and at least one D-LDH gene derived from bacteria of the genus *Lactobacillus*. The transformant according to the present invention may have only one D-LDH gene derived from bacteria of the genus *Pediococcus* or two or more such D-LDH genes. In a case where the transformant has two or more such D-LDH genes, the genes may be either D-LDH genes derived from the homologues of bacteria of the genus *Pediococcus* or D-LDH genes derived from heterologous of bacteria of the genus *Pediococcus*. The same is applied to the D-LDH gene derived from bacteria of the genus *Lactobacillus*.

[Production of Transformant]

The transformant according to the present invention is obtained by a process wherein *S. pombe* in which some of the genes in a group of PDC genes have been deleted or inactivated is used as a host, and a D-LDH gene derived from bacteria of the genus *Pediococcus* and a D-LDH gene derived from bacteria of the genus *Lactobacillus* are introduced into the *S. pombe* by a genetic engineering process. In addition, it is possible to obtain the transformant according to the present invention by a process wherein *S. pombe* in which a group of PDC genes have not been deleted or inactivated is used as a host; a D-LDH gene derived from bacteria of the genus *Pediococcus* and a D-LDH gene derived from bacteria of the genus *Lactobacillus* are introduced into the *S. pombe* by a genetic engineering process so as to obtain a transformant; and then some of the genes in a group of PDC genes of the obtained transformant are deleted or inactivated. In examples which will be described later, an intended transformant is produced by the former process. However, by the latter process, a transformant almost equivalent to the above transformant can also be obtained. In any of the processes, the D-LDH gene derived from bacteria of the genus *Pediococcus* and the D-LDH gene derived from bacteria of the genus *Lactobacillus* may be introduced sequentially (in different orders) or introduced simultaneously.

Hereinafter, the process for production of a transformant will be described by illustrating the process wherein *S. pombe* in which some of the genes in a group of PDC genes have been deleted or inactivated is used as a host, and a D-LDH gene derived from bacteria of the genus *Pediococcus* and a D-LDH gene derived from bacteria of the genus *Lactobacillus* are introduced into the host by a genetic engineering process.

<Host>

The *S. pombe* used as a host may be a wild type or a mutant type in which specific genes have been deleted or inactivated according to the purpose. As the process for deleting or inactivating the specific genes, a known process can be used. Specifically, by using a Latour method (described in the journal of Nucleic Acids Res., 2006, Vol. 34, p. ell, PCT International Publication No. WO2007/063919, and the like), the genes are deleted. Furthermore, by a mutation separation method using a mutagen ("Experimental Method of Yeast Molecular Genetics", 1996, Gakkai Shuppan Center), a random mutation method using a polymerase chain reaction (PCR) (the journal of PCR Methods Appl., 1992, Vol. 2, pp 28-33), and the like, a mutation is introduced into some of the genes, thereby inactivating the genes. The yeast host of the genus *Schizosaccharomyces* in which specific genes have been deleted or inactivated is described in, for example, PCT International Publication No. WO2002/101038 and PCT International Publication No. WO2007/015470.

The portion in which the specific genes are deleted or inactivated may be an open reading frame (ORF) portion or an expression control sequence portion. It is particularly preferable to use a deletion or inactivation process by a PCR-mediated homologous recombination method (the journal of Yeast, 1998, Vol. 14, pp 943-951) in which the ORF portion of a structural gene is substituted with a marker gene.

A transformant in which PDC genes have been deleted or inactivated can be preferably used as a host for producing the transformant according to the present invention. Furthermore, the *S. pombe* in which the PDC genes and specific genes other than the PDC genes have been deleted or inactivated can also be used as a host. By the deletion or inactivation of a protease gene and the like, the expression efficiency of heterologous proteins can be improved, and if a host obtained in this way is used as the host in the present invention, the improvement of the production efficiency of D-lactic acid can be expected.

As the *S. pombe* used as a host, it is preferable to use those having a marker for selecting the transformant. For example, it is preferable to use a host that essentially requires a specific nutritional component for growth due to the lack of certain genes. In a case where a transformant is prepared by transformation using a vector including a target gene sequence, if the lacked gene (complementary auxotrophic marker) is introduced in advance into the vector, the auxotrophy of the host disappears in the transformant. By the difference in auxotrophy between the host and the transformant, it is possible to make a differentiation between a host and a transformant and to obtain a transformant.

For example, by using *S. pombe* which becomes uracil auxotrophic due to the deletion or inactivation of an orotidine phosphate decarboxylase gene (ura4 gene) as a host, performing transformation using a vector having a ura4 gene (complementary auxotrophic marker), and then selecting a transformant in which uracil auxotrophy has disappeared, a transformant into which the vector is incorporated can be obtained. The missing gene that makes the host auxotrophic is not limited to the ura4 gene as long as it can be used for selecting the transformant, and may be an isopropylmalate dehydrogenase gene (leu1 gene) or the like.

In addition, the *S. pombe* in which a group of PDC genes have not been deleted or inactivated can be used as a host for producing a transformant. In this case, as the host, it is possible to use a host in which the aforementioned gene (an auxotrophic marker, a protease gene, or the like) other than the PDC genes has been deleted or inactivated.

By producing a transformant by using the host and then deleting or inactivating some of the genes in a group of PDC genes of the obtained transformant, the transformant according to the present invention can be obtained.

<Process for Introduction of D-LDH Gene>

As the process for introducing a D-LDH gene into a host by a genetic engineering process, a known process can be used. As the process in which *S. pombe* is used as a host and structural genes of heterologous proteins are introduced into the host, for example, it is possible to use the processes described in Japanese Unexamined Patent Application, First Publication No. H05-15380, PCT International Publication No. WO95/09914, Japanese Unexamined Patent Application, First Publication No. 1110-234375, Japanese Unexamined Patent Application, First Publication No. 2000-262284, Japanese Unexamined Patent Application, First Publication No. 2005-198612, PCT International Publication No. WO2011/021629, and the like.

<Expression Cassette>

An expression cassette is a combination of DNA necessary for expressing an intended protein, and includes a structural gene which encodes the intended protein and a promoter and a terminator which function in a host. An expression cassette used for production of the transformant according to the present invention includes at least either a D-LDH gene derived from bacteria of the genus *Pediococcus* or a D-LDH gene derived from bacteria of the genus *Lactobacillus* and a promoter and a terminator which function in the *S. pombe*. The expression cassette may include any one or more domains among a 5'-untranslated domain and a 3'-untranslated domain. Furthermore, the cassette may include the aforementioned complementary auxotrophic marker. A plurality of D-LDH genes may be present in a single cassette. The number of D-LDH genes in a single cassette is preferably 1 to 8, and more preferably 1 to 5. In a case where a plurality of D-LDH genes is included in a single cassette, the cassette may include two or more kinds of D-LDH genes. As the expression cassette, an expression cassette which includes one or plural D-LDH genes, a promoter, a terminator, a 5'-untranslated domain, a 3'-untranslated domain, and a complementary auxotrophic marker is preferable.

In producing the transformant according to the present invention, the D-LDH gene derived from bacteria of the genus *Pediococcus* and the D-LDH gene derived from bacteria of the genus *Lactobacillus* may be introduced into the host by different expression cassettes or by a single expression cassette. As the expression cassette including the D-LDH gene derived from bacteria of the genus *Pediococcus* and the D-LDH gene derived from bacteria of the genus *Lactobacillus*, for example, an expression cassette is preferable which includes a promoter, the D-LDH gene derived from bacteria of the genus *Pediococcus*, a cleavage sequence, a complementary auxotrophic marker (for example, a ura4 gene), the D-LDH gene derived from bacteria of the genus *Lactobacillus*, and a terminator in this order from the 5' terminal side.

As the D-LDH gene derived from bacteria of the genus *Pediococcus* or the D-LDH gene derived from bacteria of the genus *Lactobacillus* that is included in the expression cassette, a gene encoded by the wild type may be used as it is. However, in order to increase the expression amount of the gene in the *S. pombe* used as a host, the gene sequence of the wild type may be modified into a codon used at a high frequency in the *S. pombe*.

The promoter and the terminator functioning in the *S. pombe* should be able to maintain the expression of LDH by functioning in the transformant even if D-lactic acid is accumulated by the transformant according to the present invention and hence the intracellular environment of the transformant becomes acidic (pH of equal to or less than 6). As the promoter functioning in the *S. pombe*, it is possible to use a promoter (preferably a promoter having high transcription initiation activity) the *S. pombe* originally has or a promoter (such as a promoter derived from a virus) the *S. pombe* does not originally have. Herein, two or more kinds of promoters may be present in a vector.

Examples of the promoter the *S. pombe* originally has include an alcohol dehydrogenase gene promoter, an nmt1 gene promoter involved in the thiamine metabolism, fructose-1,6-bisphosphatase gene promoter involved in the glucose metabolism, an invertase gene promoter involved in the catabolite repression (see PCT International Publication No. WO99/23223), a heat-shock protein gene promoter (see PCT International Publication No. WO2007/26617), and the like.

Examples of the promoter the *S. pombe* does not originally have include promoters derived from animal cell viruses, described in Japanese Unexamined Patent Application, First Publication No. H05-15380, Japanese Unexamined Patent Application, First Publication No. H07-163373, and Japanese Unexamined Patent Application, First Publication No. H10-234375. As such promoters, an hCMV promoter and an SV40 promoter are preferable.

As the terminator functioning in the *S. pombe*, it is possible to use a terminator the *S. pombe* originally has or a terminator the *S. pombe* does not originally have. Herein, two or more kinds of terminators may be present in a vector. Examples of the terminator include terminators derived from human beings, described in Japanese Unexamined Patent Application, First Publication No. H05-15380, Japanese Unexamined Patent Application, First Publication No. H07-163373, and Japanese Unexamined Patent Application, First Publication No. H10-234375. As such terminators, terminators of human lipocortin I are preferable.

<Vector>

The transformant according to the present invention has, in a chromosome, an expression cassette which includes a D-LDH gene derived from bacteria of the genus *Pediococcus* and a D-LDH gene derived from bacteria of the genus *Lactobacillus*, or both of an expression cassette which includes a D-LDH gene derived from bacteria of the genus *Pediococcus* and an expression cassette which includes a D-LDH gene derived from bacteria of the genus *Lactobacillus*. Alternatively, the transformant according to the present invention has the aforementioned cassette as an extrachromosomal gene. Having the expression cassette in a chromosome means a state where the expression cassette is incorporated into one or more sites in a chromosome of the host cell. Having the cassette as an extrachromosomal gene means a state where the transformant has a plasmid including the expression cassette in a cell. The transformant having each expression cassette is obtained by causing transformation of the *S. pombe* as a host by using a vector including each expression cassette.

The vector including each expression cassette can be produced by incorporating the expression cassette into a vector having a cyclic DNA structure or a linear DNA structure. In a case where a transformant in which the expression cassette is retained as an extrachromosomal gene in the host cell is prepared, the vector is preferably a plasmid including a sequence to be replicated in the host cell, that is, an Autonomously Replicating Sequence (ARS). In contrast, in a case where a transformant in which the expression cassette is incorporated into a chromosome of the host cell is prepared, the vector is preferably a vector which has a linear DNA structure, does not have ARS, and is introduced into the host cell. For example, the vector may be a vector consisting of linear DNA or a vector having a cyclic DNA structure that has a restriction enzyme recognition sequence for cutting and opening the vector into linear DNA when being introduced into the host. In a case where the vector is a plasmid having ARS, a linear DNA structure can be established by deleting the ARS portion or by inactivating the function of ARS by cleaving the ARS portion, and then the plasmid can be introduced into the host.

The vector having each expression cassette preferably has a marker for selecting the transformant. Examples of the marker include an orotidine phosphate decarboxylase gene (ura4 gene) and an isopropylmalate dehydrogenase gene (leu1 gene) that are complementary auxotrophic markers.

Each D-LDH gene is preferably introduced into a chromosome of the S. pombe. By the introduction of the D-LDH gene into the chromosome, a transformant excellent in passage-maintaining stability is obtained. Furthermore, a plurality of D-LDH genes can be introduced into the chromosome. In the transformant according to the present invention, the number of D-LDH genes derived from bacteria of the genus Pediococcus that are incorporated into the chromosome is preferably 1 to 20 and particularly preferably 1 to 8. In addition, the number of D-LDH genes derived from bacteria of the genus Lactobacillus that are incorporated into the chromosome of the transformant is preferably 1 to 20 and particularly preferably 1 to 8.

As the process for introducing a D-LDH gene into a chromosome, a known process can be used. For example, by the process described in Japanese Unexamined Patent Application, First Publication No. 2000-262284, a plurality of D-LDH genes can be introduced into the chromosome. By the same process, a single D-LDH gene can be introduced into the chromosome. Furthermore, as will be described later, a single D-LDH gene or a plurality of D-LDH genes can be introduced into a plurality of sites of the chromosome.

As the process for introducing the D-LDH gene derived from bacteria of the genus Pediococcus or the D-LDH gene derived from bacteria of the genus Lactobacillus into the chromosome of the S. pombe, a process is preferable in which the D-LDH gene is introduced into the chromosome by a homologous recombination method by using a vector having an expression cassette which has each D-LDH gene and a recombination site.

The recombination site of the vector is a site having a base sequence that can cause homologous recombination with a target site of homologous recombination in a chromosome of the S. pombe. The target site is a site into which the expression cassette is incorporated in the chromosome of the S. pombe. The target site can be freely set by designing the base sequence of the recombination site of the vector such that the recombination site can cause homologous recombination with the target site.

The base sequence of the recombination site and the base sequence of the target site need to share identity of equal to or higher than 70%. Furthermore, in view of facilitating the occurrence of homologous recombination, the identity shared between the base sequence of the recombination site and the base sequence of the target site is preferably equal to or higher than 90%, and more preferably equal to or higher than 95%. By using the vector having the recombination site described above, the expression cassette can be incorporated into the target site through homologous recombination.

The length (number of bases) of the recombination site is preferably 20 bp to 2,000 bp. If the length of the recombination site is equal to or greater than 20 bp, homologous recombination easily occurs. If the length of the recombination site is equal to or less than 2,000 bp, it is easy to prevent a case where the vector becomes too long and thus the homologous recombination does not easily occur. The length of the recombination site is more preferably equal to or greater than 100 bp, and even more preferably equal to or greater than 200 bp. In addition, the length of the recombination site is more preferably equal to or less than 800 bp, and even more preferably equal to or less than 400 bp.

The vector may have other DNA domains in addition to the aforementioned expression cassette and recombination site. Examples of the DNA domains include a replication initiation domain called "ori" that is necessary for the replication in E. coli and an antibiotic resistance gene (a neomycin resistance gene or the like). These are genes generally required in a case where a vector is constructed using E. coli. Here, it is preferable that the replication initiation domain be removed when the vector is incorporated into the chromosome of the host as will be described later.

In a case were the D-LDH gene is incorporated into the chromosome, the vector preferably has a linear DNA structure when being introduced into the S. pombe cell. That is, in a case where the vector is a vector having a cyclic DNA structure such as plasmid DNA that is generally used, it is preferable that the vector be introduced into the S. pombe cell after being cut and opened to become linear DNA by a restriction enzyme.

In this case, the position in which the vector having a cyclic DNA structure is cut and opened is in the recombination site. As a result, in each of both ends of the vector cut and opened, the recombination site is partially present, and through the homologous recombination, the entirety of the vector is incorporated into the target site of the chromosome.

As long as a linear DNA structure can be established for the vector such that a portion of the recombination site is present in each of both ends thereof, the vector may be constructed by a process other than the process of cut-opening the vector having a cyclic DNA structure.

As the vector, for example, plasmids derived from E. coli, such as pBR 322, pBR 325, pUC 118, pUC 119, pUC 18, and pUC 19, can be suitably used.

In this case, it is preferable that a replication initiation domain called "ori" necessary for the replication in E. coli be removed from the plasmid vector used for homologous recombination of the chromosome of the S. pombe. In this way, when the vector is incorporated into the chromosome, the incorporation efficiency can be improved.

The process for construction of the vector from which the replication initiation domain has been removed is not particularly limited, but it is preferable to use the process described in Japanese Unexamined Patent Application, First Publication No. 2000-262284. That is, it is preferable to use a process of constructing in advance a precursor vector in which a replication initiation domain is inserted into a cleavage site in the recombination site such that the vector has the linear DNA structure described above and the replication initiation domain is cut off. By the process, a vector from which a replication initiation domain has been removed can be easily obtained.

Furthermore, it is also preferable to use a process in which a precursor vector having an expression cassette and a recombination site is constructed by using the expression vector described in Japanese Unexamined Patent Application, First Publication No. H05-15380, Japanese Unexamined Patent Application, First Publication No. H07-163373, PCT International Publication No. WO96/23890, Japanese Unexamined Patent Application, First Publication No. H10-234375, and the like or using the construction process thereof, and a replication initiation domain is removed from the precursor vector by a general genetic engineering technique so as to obtain a vector used for homologous recombination.

<Target Site>

The target site into which the vector is incorporated may be present in only one site or two or more sites in the chromosome of the S. pombe. In a case where two or more target sites are present, the vector is incorporated into the two or more sites of the chromosome of the S. pombe. In a case where a plurality of D-LDH genes are included in a single expression cassette, a plurality of LDH genes can be incorporated into one target site. In addition, by using two or more kinds of vectors having recombination sites corresponding to each of the target sites, the expression cassette can be incorporated into two or more target sites. By this process, a plurality of LDH genes can be incorporated into the chromosome of the S. pombe. As a result, the expression amount of D-LDH can be increased, and the productivity of D-lactic acid can be improved. For example, by incorporating an expression cassette including a D-LDH gene derived from bacteria of the genus Pediococcus into a vector having a first target site, incorporating an expression cassette including a D-LDH gene derived from bacteria of the genus Lactobacillus into a vector having a second target site, and performing transformation by using the vectors and S. pombe in which some of the genes in a group of PDC genes have been deleted or inactivated as a host, the transformant according to the present invention is obtained.

In a case where an expression cassette is incorporated into one target site, for example, it is possible to use the target site shown in the process described in Japanese Unexamined Patent Application, First Publication No. 2000-262284. If the above process is used, it is also possible to incorporate vectors into different target sites by using two or more kinds of vectors having different recombination sites. However, the process is complicated for incorporating vectors into two or more sites of the chromosome.

As long as a plurality of portions present in a chromosome and having base sequences substantially the same as each other, can be used as target sites, and a vector can be incorporated into each of the plurality of target sites, the vector can be incorporated into two or more sites in the chromosome by using one kind of vector. The base sequences substantially the same as each other mean that the sequences share identity of equal to or higher than 90%. The identity shared between the target sites is preferably equal to or higher than 95%. The length of each of the base sequences substantially the same as each other is a length including the recombination site of the aforementioned vector, which is preferably equal to or greater than 1,000 bp. In a case where LDH genes are incorporated into a plurality of target sites in a dispersed state, even if the same number of D-LDH genes are incorporated into the target sites, a phenomenon in which the D-LDH genes are broken away all at once from the chromosome when the transformant grows occurs less than in a case where a plurality of D-LDH genes is incorporated into a single target site. Therefore, the passage-maintaining stability of the transformant is improved.

As the plurality of target sites present in the chromosome, transposon genes Tf2 are preferable. Tf2 is a transposon gene present in a total of 13 sites in each triple-strand (monoploid) chromosome of the S. pombe. The length (number of bases) thereof is known to be about 4,900 bp, and the base sequence identity shared between the genes thereof is known to be 99.7% (see the following documents).

Nathan J. Bowen et al, "Retrotransposons and Their Recognition of pol II Promoters: A Comprehensive Survey of the Transposable Elements from the Complete Genome Sequence of *Schizosaccharomyces pombe*", Genome Res. 2003 13: 1984-1997

It is possible to incorporate a vector into only one of the Tf2s present in 13 sites in the chromosome. In this case, by incorporating a vector having two or more D-LDH genes, a transformant having two or more D-LDH genes can be obtained. Furthermore, by incorporating a vector into Tf2 in two or more sites, a transformant having two or more D-LDH genes can be obtained. In this case, by incorporating the vector having two or more D-LDH genes, a transformant having more D-LDH genes can be obtained.

If a vector is incorporated into all of the 13 Tf2s, too much burden may be imposed on the survival or growth of the transformant. Therefore, the vector is preferably incorporated into 8 or less of the 13 Tf2s, and more preferably incorporated into 5 or less Tf2s.

<Transformation Process>

As the transformation process, any of known transformation processes can be used. Examples of the transformation processes include the processes known in the related art, such as a lithium acetate method, an electroporation method, a spheroplast method, and a glass bead method, and the process described in Japanese Unexamined Patent Application, First Publication No. 2005-198612. Furthermore, commercially available yeast transformation kits may be used.

As the process for transforming the S. pombe host by a homologous recombination method, a known homologous recombination method can be used. As the transformation process at the time of producing the transformant according to the present invention, a process is preferable wherein S. pombe in which some of the genes in a group of PDC genes described above have been deleted or inactivated is used as a host, and an expression cassette is incorporated into the chromosome of the S. pombe through homologous recombination by using the vector described above. According to this process, the transformant according to the present invention can be simply produced.

At the time of producing the transformant, generally, after homologous recombination is performed, the obtained transformant is selected. As the selection process, for example, the following process can be used. By using a medium that can select the transformant by the aforementioned auxotrophic marker, screening is carried out, thereby selecting a plurality of transformants from the obtained colony. Then, each of the transformants is individually subjected to liquid culture. Thereafter, the expression amount of a heterologous protein (in the present invention, D-LDH derived from bacteria of the genus Pediococcus or D-LDH derived from bacteria of the genus Lactobacillus) in each culture solution is investigated, and transformants showing a greater expression amount of the heterologous protein are selected. Through a pulse field gel electrophoresis method, genomic analysis is performed on the selected transformants, and in this way, the number of vectors or expression cassettes incorporated into the chromosome is investigated.

The number of vectors incorporated into the chromosome can be adjusted to some extent by adjusting the incorporation conditions or the like. It is considered that the incorporation efficiency or the number of vectors incorporated may vary with the size (number of bases) or structure of the vector.

Generally, the greater the number of expression cassettes, the higher the expression efficiency of D-LDH, and presumably, this may lead to the increase in the production efficiency of D-lactic acid. Therefore, it is considered that by incorporating a plurality of D-LDH genes into the chromosome of the S. pombe, the expression amount of D-LDH can be increased, and the productivity of D-lactic acid can be improved. However, it is also considered that if the number of expression cassettes is too great, the burden imposed on the survival or growth of the cells may be increased, and in turn the production efficiency of D-lactic acid may be reduced. In contrast, by including a plurality of genes in a single expression cassette, it is possible to reduce the number of expression cassettes to be incorporated into the chromosome and to incorporate a large number of D-LDH genes into the chromosome. However, it is considered that if the size of the vector is increased, a probability that the vector will be incorporated into the chromosome may be reduced, the number of vectors to be incorporated may not be easily increased, and thus the transformant may not be easily obtained.

Therefore, the inventors of the present invention thought that even in a case where a relatively small number of expression cassettes having an appropriate size are incorporated into the chromosome, in order to obtain a S. pombe transformant having high D-lactic acid production efficiency, a foreign D-LDH gene, which is highly efficiently expressed in the S. pombe and results in high activity of the expressed D-LDH, needs to be selected and introduced into the chromosome. As a result of investigating D-LDH genes derived from various microorganisms, the inventors found that by incorporating a D-LDH gene derived from bacteria of the genus Pediococcus or a D-LDH gene derived from bacteria of the genus Lactobacillus into a S. pombe transformant in which some of the genes in a group of PDC genes have been deleted or inactivated, a transformant having extremely high D-lactic acid production efficiency can be obtained. In addition, surprisingly, it was found that in a case where both of the D-LDH gene derived from bacteria of the genus Pediococcus and the D-LDH gene derived from bacteria of the genus Lactobacillus are incorporated into the S. pombe transformant, a transformant having markedly higher D-lactic acid production efficiency is obtained, than in a case where D-LDH genes derived from other species of living organisms are incorporated into the S. pombe transformant in combination.

[Process for Production of Lactic Acid]

A process for production of lactic acid according to the present invention is a production process of lactic acid, in which the transformant according to the present invention is fermented in a fermentation solution, and D-lactic acid is obtained from the fermentation solution.

By fermenting the transformant according to the present invention in a sugar-containing fermentation solution, pyruvic acid obtained from the sugar through a glycolytic system is reduced by D-lactate dehydrogenase, and D-lactic acid is produced. By obtaining the D-lactic acid produced in the fermentation solution from the fermentation solution, lactic acid can be produced.

As the culture medium or the fermentation medium used for producing D-lactic acid, a known sugar-containing culture medium or fermentation medium for yeast can be used. Furthermore, the culture medium or the fermentation medium should contain a nitrogen source, inorganic salts, and the like the S. pombe can utilize and should enable the S. pombe to be efficiently cultured or fermented. As the culture medium or the fermentation medium, a natural medium or a synthetic medium may be used.

Examples of the sugar as a carbon source include sugars such as glucose, fructose, sucrose, and maltose. Examples of the nitrogen source include ammonia, an ammonium salt of an inorganic or organic acid, such as ammonium chloride or ammonium acetate, peptone, casamino acid, yeast extract, and the like. Examples of the inorganic salts include magnesium phosphate, magnesium sulfate, sodium chloride, and the like. It is also possible to further add a fermentation-accelerating factor such as proteolipid.

In the process for production of lactic acid according to the present invention, it is preferable to use a fermentation medium particularly containing glucose or sucrose as sugar. The concentration of glucose or sucrose in the fermentation solution (100% by mass) at the initial stage of fermentation is preferably equal to or greater than 1% by mass, more preferably 1% by mass to 50% by mass, and even more preferably 2% by mass to 16% by mass. After the glucose concentration or the sucrose concentration is reduced due to fermentation, it is preferable to continue the fermentation by adding glucose or a fermentation medium as necessary. At the final stage of fermentation, the glucose concentration or the like may become equal to or less than 1% by mass. In a case where continuous fermentation is performed in which fermented supernatant containing D-lactic acid is continuously collected from the fermentation tank, and at the same time the fermentation medium is supplied, it is preferable to maintain the glucose concentration or the like. If the glucose concentration is set to be equal to or greater than 2% by mass, the productivity of D-lactic acid is further improved. Furthermore, if the concentration of glucose or sucrose in the fermentation solution is set to be equal to or less than 16% by mass, the production efficiency of D-lactic acid is further improved.

In order to improve the productivity of D-lactic acid production, it is preferable to perform high-density fermentation. During the high-density fermentation, the initial bacterial cell concentration of the transformant in the fermentation solution, expressed in terms of the weight of dry bacterial cells, is preferably set to be 0.1 g/L to 50 g/L. The initial bacterial cell concentration of the transformant in the fermentation solution, expressed in terms of the weight of dry bacterial cells, is more preferably set to be 10 g/L to 40 g/L. If the initial bacterial cell concentration is set to be high, high productivity can be achieved within a short period of time. Furthermore, if the initial bacterial cell concentration is too high, a problem such as the aggregation of bacterial cells or the reduction of purification efficiency may occur.

The bacterial cell concentration described in examples and the like, which will be described later, is a value converted from an absorbance ($OD_{660}$) of light having a wavelength of 660 nm measured by a visible-ultraviolet spectrometer V550 manufactured by JASCO Corporation. The value of 1 that equals $OD_{660}$ at 660 nm corresponds to a dry weight of 0.2 g and a wet weight of 0.8 g of fission yeast in 1,000 mL of a culture solution.

For the culture or fermentation of the yeast, a known process can be used. For example, shake culture or shake fermentation or stirring culture or stirring fermentation can be used.

The culture temperature of the fermentation temperature is preferably 23° C. to 37° C., and the culture time or the fermentation time can be appropriately determined.

The culture or the fermentation may be batch culture or batch fermentation or may be continuous culture or continuous fermentation. For example, after the fermentation is performed by batch fermentation, by separating the bacterial cells from the fermentation solution, fermented supernatant containing D-lactic acid can be obtained. In addition, for the continuous fermentation method, for example, a process can be used in which a portion of the fermentation solution is taken out of the fermentation tank, fermented supernatant containing D-lactic acid is separated and collected from the taken fermentation solution while the bacterial cell-containing solution not being separated is returned to the fermentation tank, and glucose or a fermentation medium is newly added to the fermentation tank. By performing the continuous fermentation, the productivity of D-lactic acid is further improved.

In the process for production of lactic acid using the transformant according to the present invention, the *S. pombe* particularly excellent in acid resistance is used. Therefore, even if the pH is lowered (to about pH 2 to 4) due to the accumulation of lactic acid, D-lactic acid can be produced without performing neutralization. Accordingly, even after the pH of the fermentation solution becomes equal to or less than 3.5, it is possible to produce D-lactic acid by further continuing fermentation by means of continuous fermentation or the like. The pH at the final stage of the fermentation or the pH during the continuous fermentation is preferably 1.5 to 3.5, and particularly preferably 2.3 to 3.5. In order to improve the productivity of D-lactic acid, it is preferable to further continue fermentation after the pH of the fermentation solution becomes equal to or less than 3.5. The transformant according to the present invention is excellent in acid resistance. Consequently, it is possible to continue fermentation without neutralizing D-lactic acid in the fermentation solution that is produced by the transformant.

The D-lactic acid can be obtained from the fermentation solution by a known process. Particularly, it is preferable to obtain the D-lactic acid by separating it from the fermentation solution without neutralizing the D-lactic acid in the fermentation solution. For example, it is possible to use a process in which bacterial cells are separated by centrifugation from the fermentation solution after the end of the fermentation, and D-lactic acid is extracted using diethyl ether or ethyl acetate after the pH becomes equal to or less than 1; a process in which the fermentation solution is absorbed onto an ion-exchange resin and washed, and then D-lactic acid is eluted; a process in which impurities are removed using activated carbon; a process in which the fermentation solution is reacted with alcohol in the presence of an acid catalyst and then subjected to distillation; and a process in which D-lactic acid is separated using a separation membrane. Furthermore, in some cases, by neutralizing D-lactic acid in the fermentation solution and then separating lactate from the fermentation solution, D-lactic acid can be obtained. For example, by a process of converting D-lactic acid in the fermentation solution into a calcium salt or a lithium salt and crystallizing the neutralized salt, D-lactic acid can also be obtained.

The process for production of lactic acid according to the present invention described above uses the transformant using *S. pombe* particularly excellent in acid resistance as a host. Therefore, even if neutralization by an alkali is not performed, D-lactic acid can be simply produced with high productivity. In addition, because some of the genes in a group of PDC genes are deleted or inactivated, the ethanol fermentation efficiency is reduced. Accordingly, the sugar-based yield (a ratio of the amount of produced lactic acid to the amount of consumed sugar) of the D-lactic acid is improved. In the present invention, the sugar-based yield of the D-lactic acid can easily become equal to or greater than 50%. In some cases, the sugar-based yield of the D-lactic acid becomes equal to or greater than 70%. Furthermore, the process for production of lactic acid according to the present invention is also suitable for high-density fermentation that is performed in the presence of high-concentration glucose by using a high-concentration transformant.

EXAMPLES

Hereinafter, the present invention will be specifically described by illustrating examples and comparative examples, but the present invention is not limited to the following description. In the present examples, unless otherwise specified, "%" means "% by mass". Furthermore, in the following examples, unless otherwise specified, D-lactic acid will be simply referred to as "lactic acid" as well.

Example 1

<Preparation of PDC2 Gene Deletion Strain of *S. pombe*>

A uracil auxotrophic ARC010 strain of *S. pombe* (genotype: h-, leu1-32, and ura4-D18) (see PCT International Publication No. WO2007/015470) was transformed according to a Latour method (described in the journal of Nucleic Acids Res., 2006, Vol. 34, p. ell, PCT International Publication No. WO2007/063919, and the like), thereby preparing a deletion strain (IGF543 strain) from which PDC 2 genes (strain name: SPAC1F8. 07c) were deleted.

For preparing a deletion fragment, total genomic DNA prepared from an ARC032 strain of *S. pombe* (genotype: h-) (see PCT International Publication No. WO2007/015470) by using DNeasy (manufactured by QUIAGEN) was used as a template, and 8 kinds of synthetic oligo DNA (manufactured by Operon Biotechnologies) having the base sequences shown in were used.

TABLE 1

Oligo DNA for preparing pdc2 deletion fragment

| Oligo DNA | Base sequence | SEQ ID No. |
|---|---|---|
| UF | 5'-CTCTCCAGCTCCATCCATAAG-3' | 1 |
| UR | 5'-GACACAACTTCCTACCAAAAAGCCTTTCTGCCCATG TTTTCTGTC-3' | 2 |
| OF | 5'-GCTTTTTGGTAGGAAGTTGTGTC-3' | 3 |
| OR | 5'-AGTGGGATTTGTAGCTAAGCTGTATCCATTTCAGCC GTTTGTG-3' | 4 |
| DF | 5'-AAGTTTCGTCAATATCACAAGCTGACAGAAAACATG GGCAGAAAG-3' | 5 |
| DR | 5'-GTTCCTTAGAAAAAGCAACTTTGG-3' | 6 |
| FF | 5'-CATAAGCTTGCCACCACTTC-3' | 7 |
| FR | 5'-GAAAAAGCAACTTTGGTATTCTGC-3' | 8 |

Specifically, by a PCR method using KOD-Dash (manufactured by TOYOBO CO., LTD.), a UP domain was prepared using UF and UR, an OL domain was prepared using OF and OR, and a DN domain was prepared using DF and DR. Then, by using these as templates, a full-length deletion fragment was prepared by the same PCR method using FF and FR respectively. At the time of preparing the full-length deletion fragment, 2 kinds of synthetic oligo DNA (manufactured by Operon Biotechnologies) having the base sequences shown in Table 2 were used, and the total genomic DNA prepared from the ARC032 strain in the same manner was used as a template. Furthermore, the fragment of a domain of a uracil auxotrophic marker ura4 of *S. pombe* (strain name listed in GeneDB: SPCC330.05c, orotidine-5'- phosphate decarboxylase gene) prepared by the same PCR method was also used in combination as a template.

TABLE 2

Oligo DNA for preparing ura4 fragment

| Oligo DNA | Base sequence | SEQ ID No. |
|---|---|---|
| F | 5'-AGCTTAGCTACAAATCCCACT-3' | 9 |
| R | 5'-AGCTTGTGATATTGACGAAACTT-3' | 10 |

The obtained PDC2 gene deletion strain of *S. pombe* (an IGF543 strain, h-, leu1-32, ura4-D18, and pdc2-D23) had a slow growth rate. Therefore, in order to restore the growth rate, the IGF543 strain was streaked on a YES plate (0.5% of yeast extract, 3% of glucose, and SP supplements) and cultured at 25° C., and the obtained colony was seeded into a YPD medium (1% of yeast extract, 2% of peptone, and 2% of glucose) and then cultured at 25° C. Then, by using the culture solution containing full-grown cells, a glycerol stock was prepared and stored at −80° C. By repeating the above operation until an appropriate growth rate was obtained, a strain whose growth rate was restored was prepared (named after IGF543).

Example 2

<Preparation of LDH Gene Single-copy Introduction Strain of *S. pombe*>

*S. pombe* transformants were prepared (Table 13) into which a PaDLDH gene, a PpDLDH gene, an LbDLDH gene, an LbrDLDH gene, an LpDLDH gene, a D-LDH gene of *Lactobacillus fermentum* (LfDLDH gene) (GenBank accession number: BAG28106. 1.), a D-LDH gene of *Lactobacillus casei* (LcDLDH gene) (GenBank accession number: CAQ67405.1.), a D-LDH gene of *Lactobacillus plantarum* (LplDLDH gene) (GenBank accession number: CCC79301. 1.), a D-LDH gene of *Staphylococcus aureus* (SaDLDH gen) (GenBank accession number: BAB96309. 1.), or a D-LDH gene of *Leuconostoc mesenteroides* (LmDLDH gene) (GenBank accession number: ABJ62843. 1.) was introduced.

Specifically, according to the process of Bahler et al (the journal of Yeast, 1998, Vol. 14, pp 943-951), the IGF543 strain (gene deletion strain of *S. pombe*) prepared in Example 1 was transformed using a digest of a restriction enzyme BsiWI of a monodentate integrative recombinant vector pSLh-PaDLDH retaining a PaDLDH gene expression cassette, a monodentate integrative recombinant vector pSLh-PpDLDH retaining a PpDLDH gene expression cassette, a monodentate integrative recombinant vector pSLh-LbDLDH retaining an LbDLDH gene expression cassette, a monodentate integrative recombinant vector pSLh-LbrDLDH retaining an LbrDLDH gene expression cassette, a monodentate integrative recombinant vector pSLh-LpDLDH retaining an LpDLDH gene expression cassette, a monodentate integrative recombinant vector pSLh-LfDLDH retaining an LfDLDH gene expression cassette, a monodentate integrative recombinant vector pSLh-LcDLDH retaining an LcDLDH gene expression cassette, a monodentate integrative recombinant vector pSLh-LplDLDH retaining an LplDLDH gene expression cassette, a monodentate integrative recombinant vector pSE-SaDLDH retaining an SaDLDH gene expression cassette, or a monodentate integrative recombinant vector pSE-LmDLDH retaining an LmDLDH gene expression cassette.

The monodentate integrative recombinant vector pSE was prepared by the following process. That is, first, through ligation, a DNA fragment obtained by double digestion of an integrative vector pTL2M5 (see PTL 1) for fission yeast by restriction enzymes AflIII and XbaI was connected to a ura4-ORF fragment amplified by PCR using *S. pombe* genome as a template and a primer set represented by SEQ ID NOS: 11 and 12, thereby obtaining a vector pTL2M5-ura4. Then, through ligation, a DNA fragment which was obtained by the digestion of pTL2M5-ura with a restriction enzyme Bst1107I was connected to a DNA fragment of SEQ ID NO: 13 including recognition sequences of totally synthetic restriction enzymes PmeI and PmaCI, thereby obtaining a pRU vector. Thereafter, through ligation, a fragment which was obtained by the digestion of the obtained pRU vector with a restriction enzyme PmeI was connected to a fragment obtained by the digestion of an ef1-DW fragment which was amplified by means of PCR using the *S. pombe* genome as a template and a primer set represented by SEQ ID NOS: 14 and 15 with a restriction enzyme PmeI, thereby obtaining a pRU-efd vector. Subsequently, through ligation, a fragment which was obtained by the digestion of the obtained pRU-efd vector with a restriction enzyme SpeI was connected to a fragment obtained by the digestion of an ef1-UP fragment which was amplified by means of PCR using the *S. pombe* genome as a template and a primer set represented by SEQ ID NOS: 16 and 17 with a restriction enzyme NheI, thereby preparing a pSE vector (7,180 bp, FIG. 1) having a sequence (5'→3', cyclic) represented by SEQ ID NO: 18.

Figure 2:
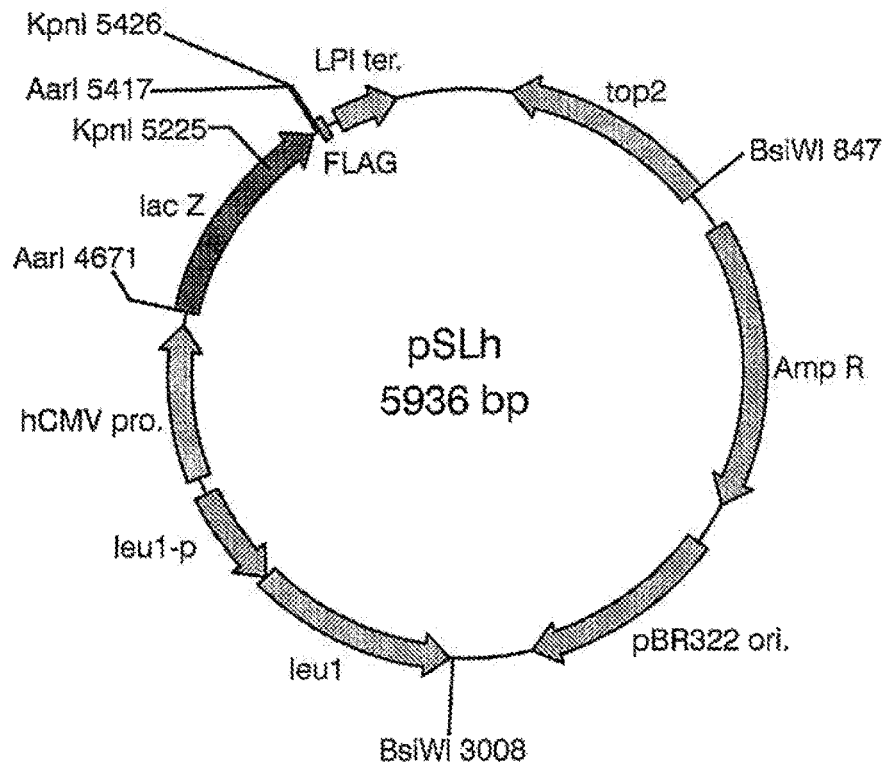
FIG. 2 is a schematic view of the structure of a recombinant vector pSLh.

A monodentate integrative recombinant vector pSLh was prepared by the following process. That is, first, by using a vector which was prepared by total synthesis of DNA and includes a sequence Y1 represented by SEQ ID NO: 19 as a template and a primer set represented by SEQ ID NOS: 20 and 21, a PCR reaction was performed, and the amplified PCR product was subjected to double digestion by using restriction enzymes KpnI and SnaBI, thereby obtaining a DNA fragment. Through ligation, the DNA fragment was connected to a fragment which was obtained by the digestion of a pSL1 vector with a restriction enzyme BsiWI and a DNA fragment obtained by the digestion of a PCR product which was obtained by a PCR reaction by using a pSL6 vector as a template and a primer set represented by SEQ ID NOS: 22 and 23 with a restriction enzyme BsiWI and then by the double-digestion of the obtained digest with restriction enzymes KpnI and SnaBI. In this way, pSLh (5,936 bp, FIG. 2) having a sequence (5'→3', cyclic) represented by SEQ ID NO: 24 was prepared.

pSLh-PaDLDH was prepared by the following process. That is, first, by using total genomic DNA prepared by DNeasy (manufactured by QUIAGEN) from the culture of a *Pediococcus acidilactici* NBRC 3076 strain (obtained from NBRC (Biological Resource Center, NITE)) as a template and using two kinds of synthetic oligo DNA (PaDLDH-F and PaDLDH-R, manufactured by Operon Biotechnologies) described in Table 3, an ORF fragment of a PaDLDH gene was obtained by a PCR method using KOD-Dash (manufactured by TOYOBO CO., LTD.). The ORF fragment encoded PaDLDH (SEQ ID NO: 27).

TABLE 3

| | Sequence | SEQ ID No. |
|---|---|---|
| PaDLDH-F | gacactttttcaaaCATGAAGATTATTGCTTATGGAATTCGTGAC | 25 |
| PaDLDH-R | atcatcatcatccttgtaatcCTCAAACTTAACTTCATTCTTTGAAGAATTCTTTC | 26 |
| PaDLDH | MKIIAYGIRDDEKPYLDEWVTKNHIEVKAVPDLLDSSNIDLAKD YDGVVAYQQKPYTADLEDKMHEFGIHAFSLRNVGLDNVPADALK KNDIKISNVPAYSPRAIAELSVTQLLALLRKIPEFEYKMAHGDY RWEPDIGLELNQMTVGVIGTGRIGRAAIDIFKPFGAKVIAYDVF RNPALEKEGMYVDTLEELYQQANVITLHVPALKDNYHMLDEKAF GQMQDGTFILNFARGTLVDTPALLKALDSGKVAGAALDTYENEV GIFDVDHGDQPIDDPVFNDLMSRRNVMITPHAAFYTRPAVKNMV QIALDNNRDLIEKNSSKNEVKFE | 27 |

By using an In-Fusion (registered trademark) HD Cloning Kit (manufactured by Clontech Laboratories, Inc.), the obtained amplified fragment was incorporated into pSLh, thereby preparing pSLh-PaDLDH. The In-Fusion method was performed according to the manual included in the kit. That is, the obtained PCR product was purified using a spin column, added to an In-Fusion reaction solution together with pSLh, and reacted for 15 minutes at 50° C.

pSLh-PpDLDH was prepared by the following process. That is, first, by using total genomic DNA prepared by DNeasy (manufactured by QUIAGEN) from the culture of a *Pediococcus pentosaceus* NBRC 107768 strain (obtained from NBRC) as a template and using two kinds of synthetic oligo DNA (PpDLDH-F and PpDLDH-R, manufactured by Operon Biotechnologies) described in Table 4, an ORF fragment of a PpDLDH gene was obtained by a PCR method using KOD-Dash (manufactured by TOYOBO CO., LTD.). The ORF fragment encoded PaDLDH (SEQ ID NO: 30).

TABLE 4

| | Sequence | SEQ ID No. |
|---|---|---|
| PpDLDH-F | CACTTTTTCAAAcATGAAAATTATTGCTTATGGCATTCGAGATG | 26 |
| PpDLDH-R | atcatcatcatccttgtaatcGTCAAACTTAACTTCATTTTTTGCAGCAC | 29 |
| PpDLDH | MKIIAYGIRDDEKTYLEEWVKDNKIEVKAVSELLDSNTIEQAKG YDGVVAYQQKPYTDDLFDKMNEFGIHAFSLRNVGVDNVPVEALK RNNIKITNVPAYSPMAIAELSVTQLLALIRRIPEFDAKMARGDF RWEPDIALELNQMTVGVIGTGRIGRAAINIFKGFGAKVIAYDVF RNSELEKEGIYVDSLEELYRQVDVITLHVPALKDNYHMLNDEAF AQMHDGVFVLNFARGSLIDTKALLKALDSGKVAGAALDTYEDEV GVFDVDHQNDPINDPVFNDLYSRRNVKITPHAAFYTKPAVKNMV QIALENNKALIEKGAAKNEVKFD | 30 |

The obtained amplified fragment was incorporated into pSLh by an In-Fusion method, thereby obtaining pSLh-PpDLDH. The In-Fusion method was performed in the same manner as used for preparing pSLh-PaDLDH.

pSLh-LbDLDH was prepared by the following process. That is, first, by using total genomic DNA prepared by DNeasy (manufactured by QUIAGEN) from the culture of a *Lactobacillus bulgaricus* NBRC 13953 strain (obtained from NBRC) as a template and using two kinds of synthetic oligo DNA (LbDLDH-F and LbDLDH-R, manufactured by Operon Biotechnologies) described in Table 5, an ORF fragment of an LbDLDH gene was obtained by a PCR method using KOD-Dash (manufactured by TOYOBO CO., LTD.). The ORF fragment encoded LbDLDH (SEQ ID NO: 33).

TABLE 5

| | Sequence | SEQ ID No. |
|---|---|---|
| LbDLDH-F | gacactttttcaaacATGACTAAAATTTTTGCTTACGCAATTCG | 31 |
| LbDLDH-R | gaaatcaacttttgttcGCCAACCTTAACTGGAGTTTCAGC | 32 |
| LbDLDH | MTKIFAYAIREDEKPFLKEWEDAHKDVEVEYTDKLLTPETAALA | 33 |

TABLE 5-continued

| Sequence | SEQ ID No. |
|---|---|
| KGADGVVVYQQLDYTAETLQALADNGITKMSLRNVGVDNIDMAK AKELGFQITNVPVYSPNAIAEHAATQAARILRQAKAMDEKVARH DLRWAPTIGREVRDQVVGVVGTGHIGQVFMQIMEGFGAKVIAYD IFRNPELEKKGYYVDSLDDLYKQADVISLHVPDVPANVHMINDK SIAKMKQDVVIVNVSRGPLVDTDAVIRGLDSGKVFGYAMDVYEG EVGVFNEDREGKEFPDARLADLIARPNVLVTPHTAFYTTHAVRN MVVKAFDNNLELVEGKEAETPVKVG | |

The obtained amplified fragment was incorporated into pSLh by an In-Fusion method, thereby preparing pSLh-LbDLDH. The In-Fusion method was performed in the same manner as used for preparing pSLh-PaDLDH.

pSLh-LbrDLDH was prepared by the following process. That is, first, by using total genomic DNA prepared by DNeasy (manufactured by QUIAGEN) from the culture of a *Lactobacillus brevis* NBRC 107147 strain (obtained from NBRC) as a template and using two kinds of synthetic oligo DNA (LbrDLDH-F and LbrDLDH-R, manufactured by Operon Biotechnologies) described in Table 6, an ORF fragment of an LbrDLDH gene was obtained by a PCR method using KOD-Dash (manufactured by TOYOBO CO., LTD.). The ORF fragment encoded LbrDLDH (SEQ ID NO: 36).

TABLE 6

| | Sequence | SEQ ID No. |
|---|---|---|
| LbrDLDH-F | GACACTTTTTCAAAcATGAAAATTATTGCTTATGGCATTCGTG AC | 34 |
| LbrDLDH-R | atcatcatcatccttgtaatcGTCGAACGAGACTTCGTTTTCA GC | 35 |
| LbrDLDH | MKIIAYGIRDDEQPYLEQWSKDQGIEVKAVAELLDEQTVDLAK GYDGAVVYQQKPYTAAVLDQLAANGVTNLSLRNVGVDNVNADA VKRNGFKVTNVPAYSPAAIAELTVTQLMRLLRRTPTFDRKQAQ GDLTWAPDIADELNQMTVGIVATGRIGRAAMRIYQGFGAKVIA YDVFHNPELEKQGIYVDTLDELYAQADVISLHAPATKDNDHML DDAAFAKMKDGVWILNPARGALIDTDALTLALDSGKVAGAALD VYEDEVGIFNADFKNFDAIPDERLKNLMKRENVLVTPHIAFYT KTAVKNMVQFALNNNKQLIETGRAENEVSED | 36 |

The obtained amplified fragment was incorporated into pSLh by an In-Fusion method, thereby preparing pSLh-LbDLDH. The In-Fusion method was performed in the same manner as used for preparing pSLh-PaDLDH.

pSLh-LpDLDH was prepared by the following process. That is, first, by using total genomic DNA prepared by DNeasy (manufactured by QUIAGEN) from the culture of a *Lactobacillus pentosus* NBRC 106467 strain (obtained from NBRC) as a template and using two kinds of synthetic oligo DNA (LpDLDH-F and LpDLDH-R, manufactured by Operon Biotechnologies) described in Table 7, an ORF fragment of an LpDLDH gene was obtained by a PCR method using KOD-Dash (manufactured by TOYOBO CO., LTD.). The ORF fragment encoded LpDLDH (SEQ ID NO: 39).

TABLE 7

| | Sequence | SEQ ID No. |
|---|---|---|
| LpDLDH-F | gacactttttcaaacATGAAAATTATTGCATATGCTGTACGTG ATG | 37 |
| LpDLDH-R | atcatcatcatccttgtaatcGTCAAACTTAACTTGCGTGTCA GC | 38 |
| LpDLDH | MKIIAYAVRDDERPFFDTWMKENPDVEVKLVPELLTEDNVDLA KGFDGADVYQQKDYTAEVLNKLADEGVKNISLRNVGVDNLDVP TVKARGLNISNVPAYSPNAIAELSVTQLMQLLRQTPMFNKKLA KQDFRWAPDIAKELNTMTVGVIGTGRIGRAAIDIFKGFGAKVI GYDVYRNAELEKEGMYVDTLDELYAQADVITLHVPALKDNYHM LNADAFSKMKDGAYILNFARGTLIDSEDLIKALDSGKVAGAAL VTYEYETKIFNKDLEGQTIDDKVFMNLFNRDNVLITPHTAFYT ETAVHNMVHVSMNSNKQFIETGKADTQVKFD | 39 |

The obtained amplified fragment was incorporated into pSLh by an In-Fusion method, thereby preparing pSLh-LpDLDH. The In-Fusion method was performed in the same manner as used for preparing pSLh-PaDLDH.

pSLh-LfDLDH was prepared by the following process. That is, first, by using total genomic DNA prepared by DNeasy (manufactured by QUIAGEN) from the culture of a *Lactobacillus fermentum* NBRC 3956 strain (obtained from NBRC) as a template and using two kinds of synthetic oligo DNA (LfDLDH-F and LfDLDH-R, manufactured by Operon Biotechnologies) described in Table 8, an ORF fragment of an LfDLDH gene was obtained by a PCR method using KOD-Dash (manufactured by TOYOBO CO., LTD.). The ORF fragment encoded LfDLDH (SEQ ID NO: 42).

TABLE 8

|  | Sequence | SEQ ID No. |
|---|---|---|
| LfDLDH-F | GACACTTTTTCAAAcATGGCAAAAATTTACGCATACGGAATC | 40 |
| LfDLDH-R | atcatcatcatccttgtaatcACCAACCTTAACTGGGGTTTCAG | 41 |
| LfDLDH | MAKIYAYGIRKDEEPYLNEWAKNHADVTVDYTAELLTPETAAQ AAGADGVVVYQQLDYTAETLQALADQGVTKMSLRNVGIDNIDM AKAKELGFEITNVPVYSPNAIAEHAAIQTARILRQSKKLDKKI ENGDLRWAPTIGREVRDQVVGVVGTGHIGQVFMQIMEGFGAKV IAYDVFKDPELEKKGYYVSLDEIYAQADVISLHVPALESTIHM INDETIAKMKDDAVLVNVSRGPLVDTDAVIRALDSGKLFGFVM DTYEDEVGIFNEDWQGKEFPDARLNDLIHRDNVLVTPHTAFYT THAVRNMVLKAFDNNLALVKGEEPETPVKVG | 42 |

The obtained amplified fragment was incorporated into pSLh by an In-Fusion method, thereby preparing pSLh-LfDLDH. The In-Fusion method was performed in the same manner as used for preparing pSLh-PaDLDH.

pSLh-LplDLDH was prepared by the following process. That is, first, by using total genomic DNA prepared by DNeasy (manufactured by QUIAGEN) from the culture of a *Lactobacillus plantarum* NBRC 15891 strain (obtained from NBRC) as a template and using two kinds of synthetic oligo DNA (LplDLDH-F and LplDLDH-R, manufactured by Operon Biotechnologies) described in Table 9, an ORF fragment of an LplDLDH gene was obtained by a PCR method using KOD-Dash (manufactured by TOYOBO CO., LTD.). The ORF fragment encoded LplDLDH (SEQ ID NO: 45).

TABLE 9

|  | Sequence | SEQ ID No. |
|---|---|---|
| LplDLDH-F | gacacttttcaaacATGAAAATTATTGCATATGCTGTACGTGATG | 43 |
| LplDLDH-R | atcatcatcatccttgtaatcGTCAAACTTAACTTGCGTATCAGCTTTAC | 44 |
| LplDLDH | MKIIAYAVRDDERPFFDTWMKENPDVEVKLVPELLTEDNVDLA KGFDGADVYQQKDYTAEVLNKLADEGVKNISLRNVGVDNLDVP TVKARGLNISNVPAYSPNAIAELSVTQLMQLLRQTPLFNKKLA KQDFRWAPDIAKELNTMTVGVIGTGRIGRAAIDIFKGFGAKVI GYDVYRNAELEKEGMYVDTLDELYAQADVITLHVPALKDNYHM LNADAFSKMKDGAYILNFARGTLIDSEDLIKALDSGKVAGAAL DTYEYETKIFNKDLEGQTIDDKVFMNLFNRDNVLITPHTAFYT ETAVHNMVHVSMNSNKQFIETGKADTQVKFD | 45 |

The obtained amplified fragment was incorporated into pSLh by an In-Fusion method, thereby preparing pSLh-LplDLDH. The In-Fusion method was performed in the same manner as used for preparing pSLh-PaDLDH.

pSLh-LcDLDH was prepared by the following process. That is, first, by using total genomic DNA prepared by DNeasy (manufactured by QUIAGEN) from the culture of a *Lactobacillus casei* NBRC 15883 strain (obtained from NBRC) as a template and using two kinds of synthetic oligo DNA (LcDLDH-F and LcDLDH-R, manufactured by Operon Biotechnologies) described in Table 10, an ORF fragment of an LcDLDH gene was obtained by a PCR method using KOD-Dash (manufactured by TOYOBO CO., LTD.). The ORF fragment encoded LcDLDH (SEQ ID NO: 48).

TABLE 10

| | Sequence | SEQ ID No. |
|---|---|---|
| LcDLDH-F | GACACTTTTTCAAAcATGAAGATCATTGCCTACGGTGC | 46 |
| LcDLDH-R | atcatcatcatccttgtaatcCTTGGCGGGACCGGTGA | 47 |
| LcDLDH | MKIIAYGARVDEIQYFKQWAKDTGNTLEYHTEFLDENTVEWAK GFDGINSLQTTPYAAGVFEKMHAYGIKFLTIRNVGTDNIDMTA MKQYGIRLSNVPAYSPAAIAEFALTDTLYLLRNMGKVQAQLQA GDYEKAGTFIGKELGQQTVGVMGTGHIGQVAIKLFKGFGAKVI AYDPYPMKGDHPDFDYVSLEDLFKQSDIIDLHVPGIEQNTHII NEAAFNLMKPGAIVINTARPNLIDTQAMLSNLKSGKLAGVGID TYEYETEDLLNLAKHGSFKDPLWDELLGMPNVVLSPHIAYYTE TAVHNMVYFSLQHLVDFLTKGETSTEVTGPA | 48 |

The obtained amplified fragment was incorporated into pSLh by an In-Fusion method, thereby preparing pSLh-LcDLDH. The In-Fusion method was performed in the same manner as used for preparing pSLh-PaDLDH.

pSE-SaDLDH was prepared by the following process. That is, first, by using total genomic DNA prepared by DNeasy (manufactured by QUIAGEN) from the culture of a *Staphylococcus aureus* NBRC 102135 strain (obtained from NBRC) as a template and using two kinds of synthetic oligo DNA (SaDLDH-F and SaDLDH-R, manufactured by Operon Biotechnologies) described in Table 11, an ORF fragment of an SaDLDH gene was obtained by a PCR method using KOD-Dash (manufactured by TOYOBO CO., LTD.). The ORF fragment encoded SaDLDH (SEQ ID NO: 51).

TABLE 11

| | Sequence | SEQ ID No. |
|---|---|---|
| SaDLDH-F | gacacttttcaaaCATGTACATAATCTTTAATTTCACTCATT TACTTTTCAATC | 49 |
| SaDLDH-R | gagctcgaattcacatgTTAATTTAAACGTGTTTCACATGTAC CAGTG | 50 |
| SaDLDH | MYIIFNFTHLLFNLLKARFLIMTKIMFFGTRDYEKEMALNWGK KNNVEVTTSKELLSSATVDQLKDYDGVTTMQFGKLENDVYPKL ESYGIKQIAQRTAGFDMYDLDLAKKHNIVISNVPSYSPETIAE YSVSIALQLVRRFPDIERRVQTHDFTWQAEIMSKPVKNMTVAI IGTGRIGAATAKIYAGFGATITAYDAYPNKDLDFLTYKDSVKE AIKDADIISLHVPANKESYHLFDKAMFDHVKKGAILVNAARGA VINTPDLIAAVNDGTLLGAAIDTYENEAAYFTNDWTNKDIDDK TLLELIEHERILVTPHIAFFSDEAVQNLVEGGLNAALSVINTG TCETRLN | 51 |

The obtained amplified fragment was incorporated into pSE by an In-Fusion method, thereby preparing pSE-SaDLDH. The In-Fusion method was performed in the same manner as used for preparing pSLh-PaDLDH.

pSE-LmDLDH was prepared by the following process. That is, first, by using total genomic DNA prepared by DNeasy (manufactured by QUIAGEN) from the culture of a *Leuconostoc mesenteroides* NBRC 100496 strain (obtained from NBRC) as a template and using two kinds of synthetic oligo DNA (LmDLDH-F and LmDLDH-R, manufactured by Operon Biotechnologies) described in Table 12, an ORF fragment of an LmDLDH gene was obtained by a PCR method using KOD-Dash (manufactured by TOYOBO CO., LTD.). The ORF fragment encoded LmDLDH (SEQ ID NO: 54).

TABLE 12

| | Sequence | SEQ ID No. |
|---|---|---|
| LmDLDH-F | gacacttttcaaaCATGAAGATTTTTGCTTACGGCATTCG | 52 |
| LmDLDH-R | gagctcgaattcacatgTTAATATTCAACAGCAATAGCTGGCT TC | 53 |
| LmDLDH | MKIFAYGIRDDEKPSLEEWKAANPEIEVDYTQELLTPETAKLA EGSDSAVVYQQLDYTRETLTALANVGVTNLSLRNVGTDNIDFD AAREFNFNISNVPVYSPNAIAEHSMLQLSRLLRRTKALDAKIA KRDLRWAPTTGREMRMQTVGVIGTGHIGRVAINILKGFGAKVI AYDKYPNAELQAEGLYVDTLDELYAQADAISLYVPGVPENHHL INADAIAKMKDGVVIMNAARGNLMDIDAIIDGLNSGKISDFGM DVYENEVACSMKIGLVKNSPDAKIADLIARENVMITPHTAFYT TKAVLEMVHQSFDAAVAFAKGEKPAIAVEY | 54 |

The obtained amplified fragment was incorporated into pSE by an In-Fusion method, thereby preparing pSE-Lm-DLDH. The In-Fusion method was performed in the same manner as used for preparing pSLh-PaDLDH.

TABLE 13

| Strain name of transformant | Strain name of host | Name of LDH gene introduced |
|---|---|---|
| ASP4550 | IGF543 | PaDLDH |
| ASP4552 | IGF543 | PpDLDH |
| ASP4533 | IGF543 | LbDLDH |
| ASP4535 | IGF543 | LbrDLDH |
| ASP4540 | IGF543 | LfDLDH |
| ASP4541 | IGF543 | LpDLDH |
| ASP4537 | IGF543 | LcDLDH |
| ASP4545 | IGF543 | LplDLDH |
| ASP3462 | IGF543 | LmDLDH |
| ASP3466 | IGF543 | SaDLDH |

<Fermentation Test>

A YPD6 liquid medium (1% of yeast extract, 2% of peptone, and 6% of glucose) was inoculated with each of the obtained transformants, and the cells were cultured for 24 hours under the conditions of a temperature of 32° C. and a shaking rate of 110 rpm.

After the end of the culture, the bacterial cells were collected, 4.5 mL of a 11.1% aqueous glucose solution was inoculated with the bacterial cells such that the initial bacterial cell concentration became 36 g (expressed in terms of dry bacterial cells)/L, followed by fermentation for 3 or 7 hours under the conditions of a temperature of 32° C. and a shaking rate of 110 rpm. After the end of the fermentation, the concentration (g/L) of each of glucose, ethanol, and lactic acid in the fermentation solution was measured. Table 14 shows the measurement results, a lactic acid production rate (g/(L·h)), a sugar-based yield (%) of lactic acid, a dry bacterial cell concentration (g/L) after the end of fermentation, and lactic acid production rate (g/(g·h)) per dry bacterial cells that were calculated from the measurement results, and the fermentation time.

LbrDLDH gene was introduced, the ASP4540 strain into which the LfDLDH gene was introduced, the ASP4541 strain into which the LpDLDH gene was introduced, the ASP4537 strain into which the LcDLDH gene was introduced, and the ASP4545 strain into which the LplDLDH gene was introduced produced lactic acid. Particularly, the ASP4550 strain, the ASP4537 strain, the ASP4540 strain, and the ASP4533 strain had a sugar-based yield of equal to or greater than 55%, showing extremely high lactic acid productivity. In contrast, the ASP3462 strain into which the LmDLDH gene was introduced and the ASP3466 strain into which the SaDLDH gene was introduced were not confirmed to produce lactic acid.

Example 3

<Preparation of D-LDH Gene Double-copy Introduction Strain>

D-LDH genes derived from homologous or heterologous living organisms were introduced into two sites in the chromosome of the IGF543 strain prepared in Example 1, thereby preparing transformants. The lactic acid production ability of each of the transformants was investigated. A strain in which uracil auxotrophy and leucine auxotrophy were restored and into which two copies of PaDLDH gene were introduced was named an ASP4707 strain; a strain into which one copy of PaDLDH gene and one copy of LpDLDH gene were introduced was named an ASP4156 strain; a strain into which one copy of PaDLDH gene and one copy of LbDLDH gene were introduced was named an ASP4703 strain; a strain into which one copy of PaDLDH gene and one copy of LbrDLDH gene were introduced was named an ASP4704 strain; a strain into which one copy of PaDLDH gene and one copy of PpDLDH gene were introduced was named an ASP4708 strain; and a strain into which one copy of LbDLDH gene and one copy of LpDLDH gene were introduced was named an ASP4752 strain (Table 15).

Specifically, first, according to the process of Bahler et al (the journal of Yeast, 1998, Vol. 14, pp 943-951), the IGF543

TABLE 14

| DLDH gene introduced into transformant | Fermentation time [h] | Glucose concentration [g/L] | Ethanol concentration [g/L] | Lactic acid concentration [g/L] | Lactic acid production rate [g/(L·h)] | Sugar-based yield of lactic acid [%] | Dry bacterial cell concentration [g/L] | Lactic acid production rate per dry bacterial cells [g/(g·h)] |
|---|---|---|---|---|---|---|---|---|
| PaDLDH | 3.0 | 19.1 | 4.6 | 57.3 | 19.1 | 62.3 | 36.0 | 0.53 |
| PpDLDH | 3.0 | 38.7 | 6.9 | 32.1 | 10.7 | 44.4 | 36.0 | 0.30 |
| LbDLDH | 3.0 | 52.3 | 0.0 | 33.5 | 11.2 | 57.0 | 36.0 | 0.31 |
| LbrDLDH | 3.0 | 45.0 | 3.1 | 31.0 | 10.3 | 47.0 | 36.0 | 0.29 |
| LfDLDH | 3.0 | 27.1 | 3.5 | 48.9 | 16.3 | 58.4 | 36.0 | 0.45 |
| LpDLDH | 3.0 | 48.6 | 0.0 | 33.0 | 11.0 | 52.9 | 36.0 | 0.31 |
| LcDLDH | 3.0 | 31.0 | 3.6 | 50.1 | 16.7 | 62.7 | 36.0 | 0.46 |
| LplDLDH | 3.0 | 35.4 | 1.1 | 40.9 | 13.6 | 54.1 | 36.0 | 0.38 |
| LmDLDH | 7.0 | 0.0 | 43.3 | 0.5 | 0.07 | 0.45 | 33.4 | 0.0021 |
| SaDLDH | 7.0 | 0.0 | 42.4 | 0.5 | 0.07 | 0.45 | 32.7 | 0.0022 |

As a result, it was confirmed that the ASP4550 strain into which the PaDLDH gene as a D-LDH gene derived from bacteria of the genus *Pediococcus* was introduced, the ASP4552 strain into which the PpDLDH gene was introduced, the ASP4533 strain into which the LbDLDH gene as a D-LDH gene derived from bacteria of the genus *Lactobacillus* was introduced, the ASP4535 strain into which the strain (PDC2 gene deletion strain of *S. pombe*) prepared in Example 1 was transformed using a digest of a restriction enzyme BsiWI of a monodentate integrative recombinant vector pSE-PaDLDH retaining a PaDLDH gene expression cassette or a monodentate integrative recombinant vector pSE-LpDLDH retaining an LpDLDH gene expression cassette. In this way, an LDH gene single-copy introduction strain of *S. pombe* (ASP3472 strain) into which one copy of PaDLDH gene was introduced or an LDH gene single-copy introduction strain of *S. pombe* (ASP3468 strain) into which one copy of LpDLDH gene was introduced was prepared.

pSE-PaDLDH was prepared by the following process. That is, by using pSLh-PaDLDH prepared in Example 2, an expression cassette (hCMV promoter/PaDLDH-ORF/LPI terminator) was cut out by double digestion using restriction enzymes SpeI and Bst1107I, and pSE was introduced thereinto, thereby preparing pSE-PaDLDH.

Likewise, by using pSLh-LpDLDH prepared in Example 2, an expression cassette (hCMV promoter/LpDLDH-ORF/LPI terminator) was cut out by double digestion using restriction enzymes SpeI and BstI107I, and pSE was introduced thereinto, thereby preparing pSE-LpDLDH.

Each of the obtained LDH gene single-copy introduction strains of *S. pombe* was treated with 5-fluoroorotic acid (FOA) so as to remove the ura4 gene. Then, according to the process of Okazaki et al (the journal of Nucleic Acids Res., 1990, Vol. 18, pp 6485-6489), the strains were transformed using the monodentate integrative recombinant vector pSLh-PaDLDH retaining the PaDLDH gene expression cassette, the monodentate integrative recombinant vector pSLh-PpDLDH retaining the PpDLDH gene expression cassette, the monodentate integrative recombinant vector pSLh-LpDLDH retaining the LpDLDH gene expression cassette, the monodentate integrative recombinant vector pSLh-LbDLDH retaining the LbDLDH gene expression cassette, the monodentate integrative recombinant vector pSLh-LbrDLDH retaining the LbrDLDH gene expression cassette, or the monodentate integrative recombinant vector pSLh-LfDLDH retaining the LpDLDH gene expression cassette that was prepared in Example 2. In this way, D-LDH gene double-copy introduction strains of *S. pombe* were prepared into which one more copy of the PaDLDH gene, the PpDLDH gene, the LpDLDH gene, the LbDLDH gene, the LbrDLDH gene, or the LfDLDH gene controlled by the hCMV promoter was introduced into the vicinity of the position of Leu1.

Each of the obtained LDH gene double-copy introduction strains of *S. pombe* was treated with FOA so as to remove the ura4 gene, and then transformed using a leu1 gene fragment (SEQ ID NO: 55) and a ura4 gene fragment (SEQ ID NO: 56), thereby preparing strains in which uracil auxotrophy and leucine auxotrophy were restored.

<Fermentation Test>

A YPD6 liquid medium was inoculated with each of the obtained LDH gene double-copy introduction strains of *S. pombe* in the same manner as in Example 2, the cells were cultured, and the collected bacterial cells were fermented in a 11.1% aqueous glucose solution. After the end of the fermentation, the concentration (g/L) of each of glucose, ethanol, and lactic acid in the fermentation solution was measured. Furthermore, the optical purity of the lactic acid was measured by separating optical isomers by using a ligand exchange-type column. From the peak area of each of the optical isomers, the optical purity was determined by being calculated by the following equation.

$$[\text{Optical purity (\% ee)}] = ([D\text{ isomer}] - [L\text{ isomer}])/([D\text{ isomer}] + [L\text{ isomer}]) \times 100 \qquad \text{Equation:}$$

([D isomer]: peak area of D-lactic acid, [L isomer]: peak area of L-lactic acid)

Table 15 shows the fermentation time, the measurement results, and a sugar-based yield (%) of D-lactic acid and an optical purity (% ee) of D-lactic acid that were calculated from the measurement results. As control, the PaDLDH gene single-copy introduction strain (ASP3472 strain) treated with FOA was subjected to the fermentation test in the same manner.

TABLE 15

| Strain name of transformant | LDH gene introduced into transformant | Fermentation time [h] | Glucose concentration [g/L] | Ethanol concentration [g/L] | Lactic acid concentration [g/L] | Sugar-based yield of lactic acid [%] | Optical purity [% ee] |
|---|---|---|---|---|---|---|---|
| ASP3472 | PaDLDH | 3.0 | 19.1 | 4.6 | 57.3 | 62.3 | 99.2 |
| ASP4707 | PaDLDH/PaDLDH | 23.0 | 0.0 | 7.4 | 75.7 | 68.2 | 99.7 |
| ASP4156 | LpDLDH/PaDLDH | 8.0 | 3.6 | 7.6 | 84.1 | 80.5 | 99.5 |
| ASP4703 | LbDLDH/PaDLDH | 24.0 | 0.0 | 0.5 | 81.7 | 75.0 | 99.6 |
| ASP4704 | LbrDLDH/PaDLDH | 24.0 | 0.0 | 0.0 | 84.1 | 77.2 | 99.4 |
| ASP4708 | PpDLDH/PaDLDH | 8.0 | 0.0 | 12.4 | 71.2 | 64.1 | 99.8 |
| ASP4752 | LfDLDH/LpDLDH | 5.0 | 0.0 | 13.1 | 64.0 | 59.2 | 99.5 |

The sugar-based yield of the ASP4707 strain and the ASP4708 strain into which 2 copies of D-LDH gene derived from bacteria of the genus *Pediococcus* were introduced did not reach 70%, and the lactic acid production ability of these strains was not improved much compared to the lactic acid production ability of the ASP3472 strain into which only 1 copy of D-LDH gene was introduced. Furthermore, although 2 copies of D-LDH gene derived from bacteria of the genus *Lactobacillus* were introduced into the ASP4752 strain, the sugar-based yield was lower in this strain than in the ASP3472 strain which was a single-copy introduction strain. In contrast, in all of the ASP4156 strain, the ASP4703 strain, and the ASP4704 strain into which the D-LDH gene derived from bacteria of the genus *Pediococcus* and the D-LDH gene derived from bacteria of the genus *Lactobacillus* were introduced in combination, the sugar-based yield was equal to or greater than 75% which was markedly higher than the sugar-based yield of the ASP3472 strain. From these results, it was understood that in a case where the D-LDH gene derived from bacteria of the genus *Pediococcus* and the D-LDH gene derived from bacteria of the genus *Lactobacillus* are introduced into *S. pombe* in combination, a transformant having a markedly higher lactic acid production ability can be obtained, compared to the cases where the D-LDH genes are combined in other ways.

Example 4

<Fed-batch Culture of LpDLDHgene/PaDLDH Gene Introduction Strain>

5 mL of a YES medium (pH 4.5) was inoculated with the ASP4156 strain (an LpDLDH gene/PaD-LDH gene introduction strain), and the cells were cultured for 24 hours at 32° C. in a test tube (preculture 1). Furthermore, 200 mL of a YES medium (pH 4.5) was inoculated with 4 mL of the culture solution obtained by the preculture 1, and the cells were cultured for 30 hours at 32° C. in a shake-flask having a volume of 1 L (preculture 2).

Then, by using a jar fermenter having a volume of 5 L, 200 mL of the culture solution obtained by the preculture 2 was added to 1,800 mL of an initial medium (adjusted to have pH 4.5 by using a 1N aqueous sulfuric acid solution) to which an appropriate amount of trace elements and vitamins were added according to the composition shown in Table 16, and culture was started at 30° C. Herein, the concentration of each component in Table 16 signifies the concentration by volume after the inoculation of the preculture 2. 39 hours after the beginning of the culture, by using a feed medium (adjusted to have pH 4.5 by using a 1 N aqueous sulfuric acid solution) to which an appropriate amount of trace elements and vitamins were added according to the composition shown in Table 17, feeding was started. 117 hours after the beginning of culture, the culture was ended. During the culture, the lower limit of the pH was controlled and kept at 4.5 by adding 12.5% aqueous ammonia.

TABLE 16

| Component | Concentration |
| --- | --- |
| Yeast Extract | 20 g/L |
| Aqueous glucose (moisture content: 8% to 9%) | 33 g/L |
| $(NH_4)_2SO_4$ | 15 g/L |
| $KH_2PO_4$ | 8 g/L |
| $MgSO_4 \cdot 7H_2O$ | 5.34 g/L |
| $Na_2HPO_4$ | 0.04 g/L |

TABLE 17

| Component | Concentration |
| --- | --- |
| Yeast Extract | 50 g/L |
| Aqueous glucose (moisture content: 8% to 9%) | 550 g/L |
| $KH_2PO_4$ | 9.00 g/L |
| $MgSO_4 \cdot 7H_2O$ | 4.45 g/L |
| $K_2SO_4$ | 3.50 g/L |
| $Na_2SO_4$ | 0.14 g/L |
| $Na_2HPO_4$ | 0.04 g/L |

<Continuous Fermentation of LpDLDH Gene/PaDLDH Gene Introduction Strain>

From the culture solution obtained after the end of the fed-batch culture, bacterial cells were separated by centrifugation treatment. Then, an initial medium, to which an appropriate amount of trace elements and vitamins were added according to the composition shown in Table 18, was inoculated with the bacterial cells such that the initial bacterial cell concentration became 36 g (expressed in terms of dry bacterial cells)/L ($OD_{660}$=180), thereby obtaining a fermentation solution. 500 mL of the fermentation solution was moved into a jar fermenter having a volume of 1 L connected to a cross flow-type precision filtration membrane. Thereafter, the fermentation solution was circulated through a pathway along which it passes through the precision filtration membrane from the jar fermenter and returned to the jar fermenter. Subsequently, continuous fermentation in which a fermentation medium was supplied at a constant flow rate and the membrane filtrate was extracted was performed for 163 hours at 28° C. At this time, a dilution rate was set to be 0.066 (1/h). During the continuous fermentation, a precision filtration membrane with micropores having a diameter smaller than the size of the bacterial cells was used. Accordingly, the bacterial cells were caused to flow back to the tank such that they were recycled during the 163 hours of the continuous fermentation. During the continuous fermentation, the pH of the fermentation solution was reduced to 2.3 without performing pH neutralization using an alkali.

TABLE 18

| Component | Concentration |
| --- | --- |
| Yeast Extract | 5 g/L |
| Aqueous glucose (moisture content: 8% to 9%) | 136.4 g/L |
| $C_8H_5KO_4$ (potassium hydrogen phthalate) | 3 g/L |
| $Na_2HPO_4$ | 2.2 g/L |
| $MgCl_2 \cdot 6H_2O$ | 1.05 g/L |
| KCl | 1 g/L |
| $Na_2SO_4$ | 0.04 g/L |

Figure 3:
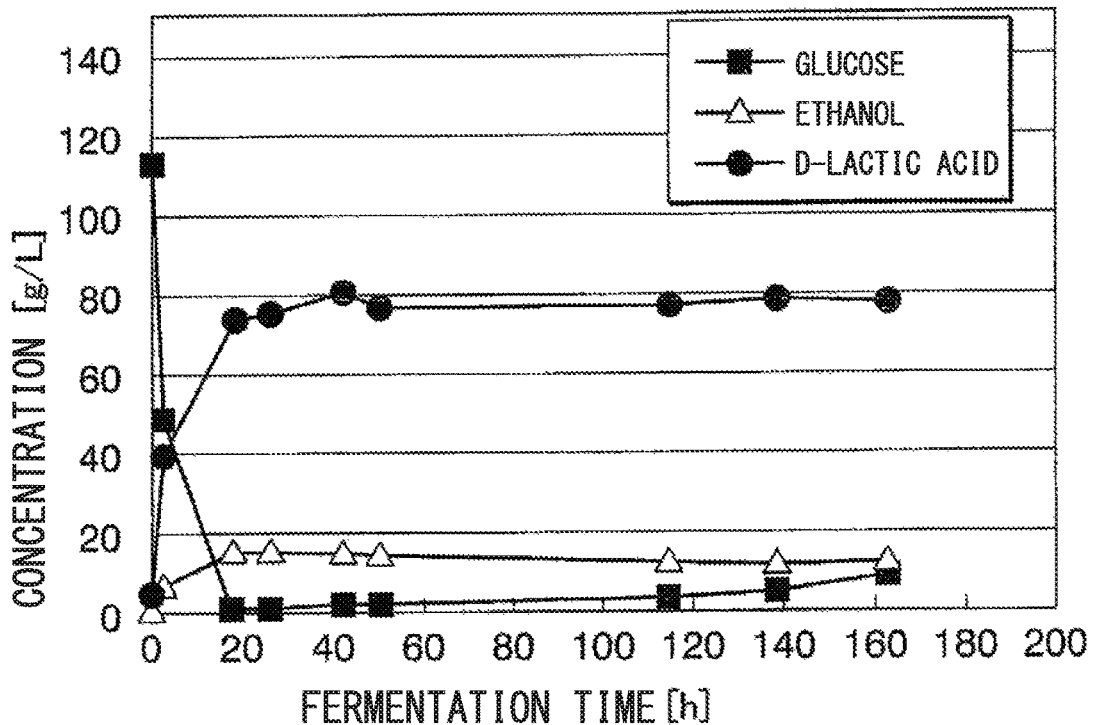
FIG. 3 is a view showing the temporal variation in the concentration (g/L) of glucose, ethanol, and D-lactic acid in a fermentation solution during continuous fermentation in Example 4.
Figure 4:
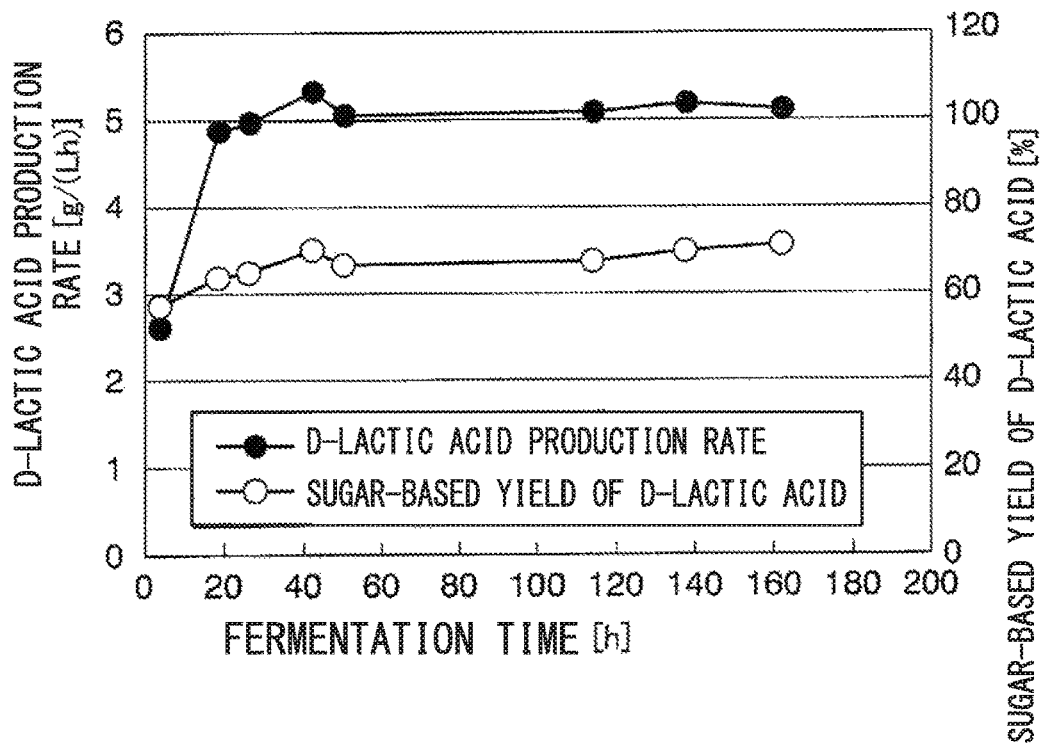
FIG. 4 is a view showing the temporal variation in the D-lactic acid production rate (g/(L·h)) and the sugar-based yield (%) of D-lactic acid in the fermentation solution during the continuous fermentation in Example 4.
Figure 5:
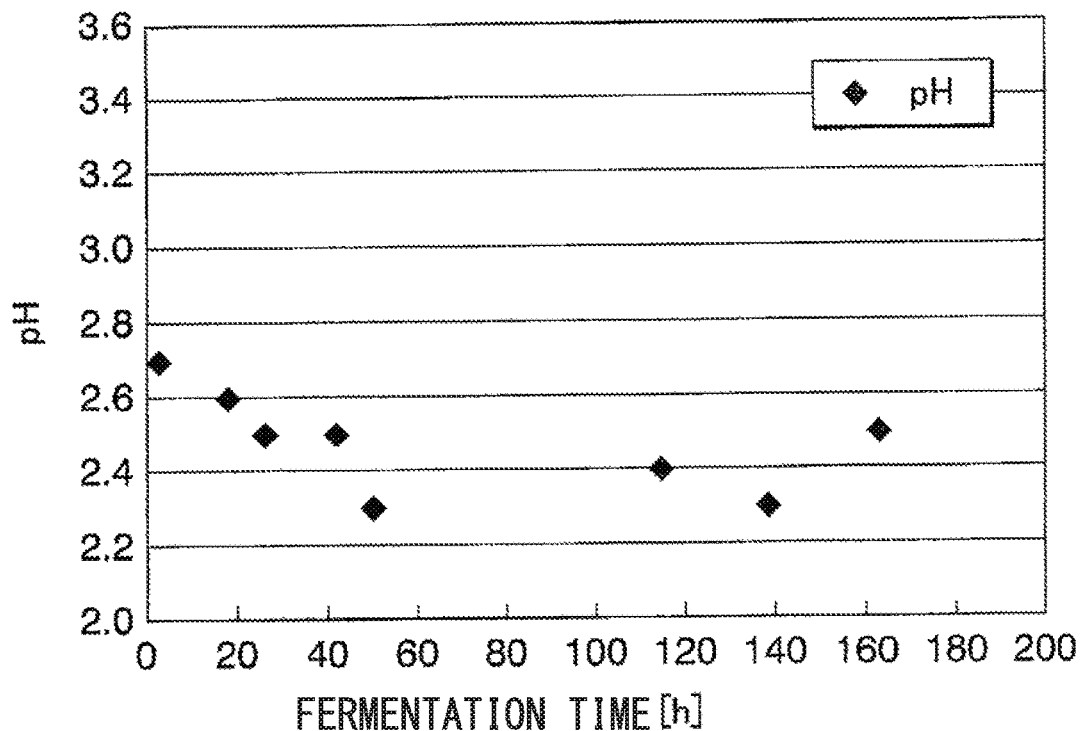
FIG. 5 is a view showing the temporal variation in the pH of the fermentation solution during the continuous fermentation in Example 4.

FIG. 3 shows the temporal variation in the concentration (g/L) of each of glucose, ethanol, and lactic acid in the fermentation solution during the continuous fermentation of the ASP4156 strain. FIG. 4 shows the temporal variation in the lactic acid production rate (g/(L·h)) and the sugar-based yield (%) of lactic acid. FIG. 5 shows the temporal variation in the pH of the fermentation solution. The pH of the fermentation solution was measured for the sampled fermentation solution by using a portable pH meter. As a result of performing continuous fermentation for 163 hours by using bacterial cells obtained by fed-batch culture, it was confirmed that, at a point in time when the fermentation ended, the lactic acid production rate was 5.1 g/(L·h), and the sugar-based yield of lactic acid was 71%. 18 hours after the beginning of the fermentation, the lactic acid concentration was increased and became equal to or greater than 70 g/L and maintained until a point in time when approximately 163 hours elapsed from the beginning of the fermentation. During the continuous fermentation, the pH was reduced to 2.3 without performing pH neutralization using an alkali, but the lactic acid production rate was maintained at about 5 g/(L·h).

At a point in time when the continuous fermentation was ended, the optical purity of the lactic acid in the fermentation solution was measured in the same manner as in Example 3 by separating optical isomers by using a ligand exchange-type column. As a result, it was confirmed that the optical purity of D-lactic acid was 99.28% ee.

Example 5

<Preparation of PaDLDH Gene Introduction Strain (ASP4878) in which Ura4 Reversion is Induced>

By using a DNA fragment obtained by the digestion of pSE with a restriction enzyme BsiWI, the ASP4550 strain into which PaDLDH was introduced was transformed, and the obtained transformant was named ASP4878.

<Fed-batch Culture of PaDLDH Gene Introduction Strain>

5 mL of a YES medium (pH 4.5) was inoculated with the ASP4878 strain (an ura4 reversion PaDLDH gene introduction strain), and the cells were cultured for 24 hours at 32° C. in a test tube (preculture 1). Furthermore, 200 mL of a YES medium (pH 4.5) was inoculated with 4 mL of the culture solution obtained by the preculture 1, and the cells were cultured for 24 hours at 32° C. in a shake-flask having a volume of 1 L (preculture 2).

Then, by using the same initial medium and feed medium as in Example 4 and using an alkali for pH control, fed-batch culture was performed. By using a jar fermenter having a volume of 5 L, 200 mL of the culture solution obtained by the preculture 2 was added to 1,800 mL of the initial medium, and culture was started at 30° C. 24 hours after the beginning of the culture, feeding was started using the feed medium. 71 hours after the beginning of the culture, the culture was ended. During the culture, the lower limit of the pH was kept at 4.5. The bacterial cell concentration at a point in time when the fed-batch culture was ended was 38.7 g (expressed in terms of dry bacterial cell)/L ($OD_{660}$ 196).

<Continuous Fermentation of PaDLDH Gene Introduction Strain>

500 mL of the culture solution after the end of the fed-batch culture was moved into a jar fermenter having a volume of 1 L, and circulated by being passed through a cross flow-type precision filtration membrane in the same manner as in Example 4. Then, by performing the supply of a fermentation medium at a constant flow rate and the extraction of the membrane filtrate under the same conditions as in Example 4, continuous fermentation was performed for 166 hours. Similarly to Example 4, during the continuous fermentation, the pH of the fermentation solution was reduced to 2.5 without performing the pH neutralization using an alkali.

Example 6

<Fed-batch Culture of LpDLDH Gene/PaDLDH Gene Introduction Strain (2)>

5 mL of a YES medium (pH 4.5) was inoculated with the ASP4156 strain (an LpD-LDH gene/PaD-LDH gene introduction strain), and the cells were cultured for 24 hours at 32° C. in a test tube (preculture 1). Furthermore, 120 mL of a YES medium (pH 4.5) was inoculated with 2.4 mL of the culture solution obtained by the preculture 1, and the cells were cultured for 30 hours at 32° C. by using a shake-flask having a volume of 500 mL (preculture 2).

Then, by using the same initial medium and feed medium as in Example 4 and using an alkali for pH control, fed-batch culture was performed. By using a jar fermenter having a volume of 3 L, 120 mL of the culture solution obtained by the preculture 2 was added to 1,080 mL of the initial medium, and culture was started at 30° C. 39 hours after the beginning of the culture, feeding was started using the feed medium. 134 hours after the beginning of the culture, the culture was ended. During the culture, the lower limit of the pH was kept at 4.5. The bacterial cell concentration at a point in time when the fed-batch culture was ended was 28.7 g (expressed in terms of dry bacterial cells)/L ($OD_{660}$=145).

<Continuous Fermentation of LpDLDH Gene/PaDLDH Gene Introduction Strain (2)>

625 mL of the culture solution after the end of the fed-batch culture was moved into a jar fermenter having a volume of 1 L, and circulated by being passed through a cross flow-type precision filtration membrane in the same manner as in Example 4. In order to increase the bacterial cell concentration, 125 mL of membrane filtrate was extracted. Then, by performing the supply of a fermentation medium at a constant flow rate and the extraction of the membrane filtrate under the same conditions as in Example 4, continuous fermentation was performed for 168 hours. Similarly to Example 4, during the continuous fermentation, the pH of the fermentation solution was reduced to 2.3 without performing the pH neutralization using an alkali.

Figure 6:
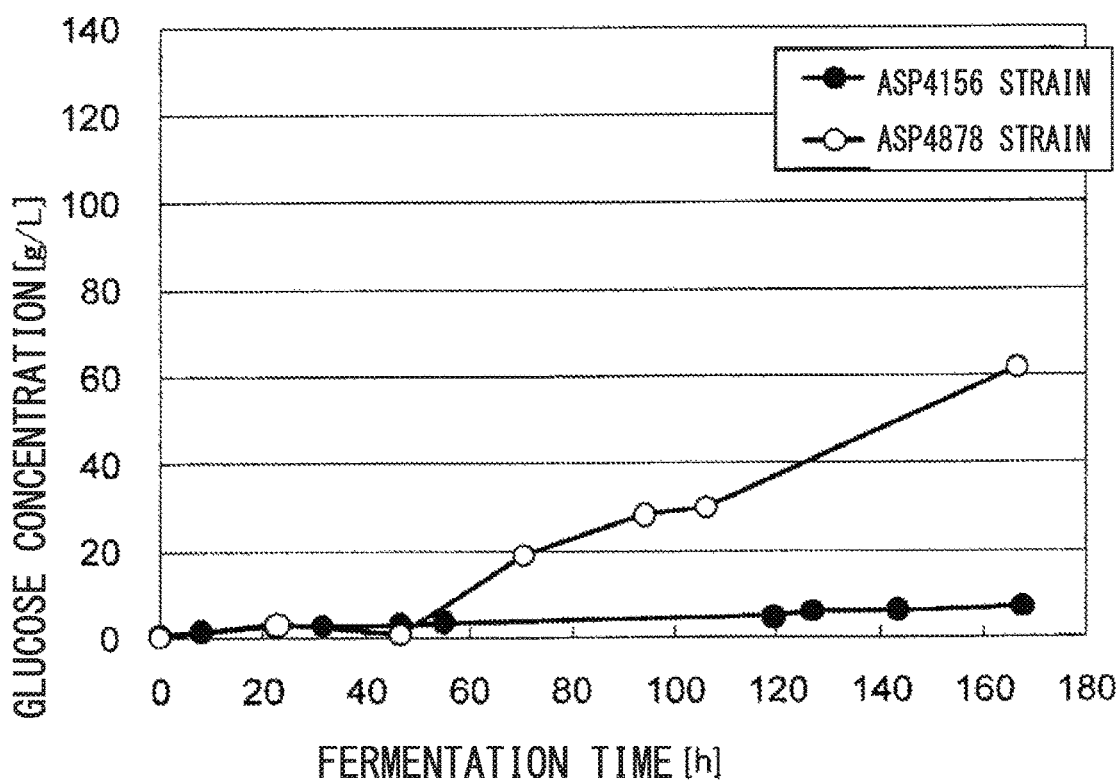
FIG. 6 is a view showing the temporal variation in the glucose concentration (g/L) in a fermentation solution during continuous fermentation in Examples 5 and 6.
Figure 7:
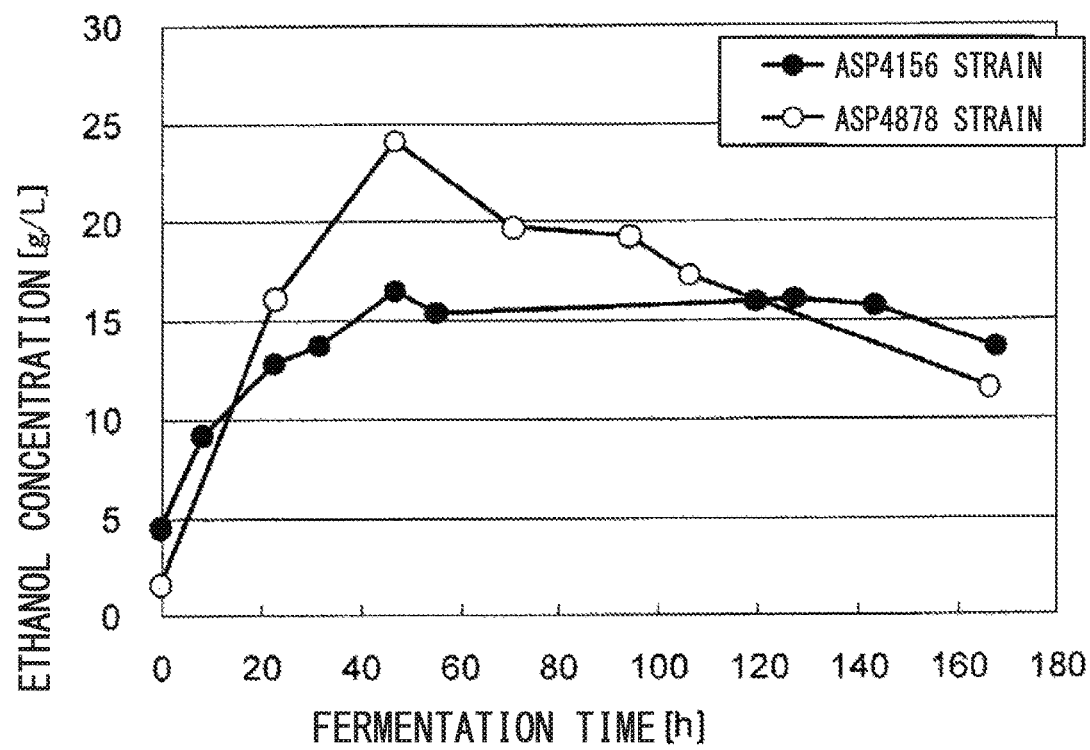
FIG. 7 is a view showing the temporal variation in the ethanol concentration (g/L) in the fermentation solution during the continuous fermentation in Examples 5 and 6.
Figure 8:
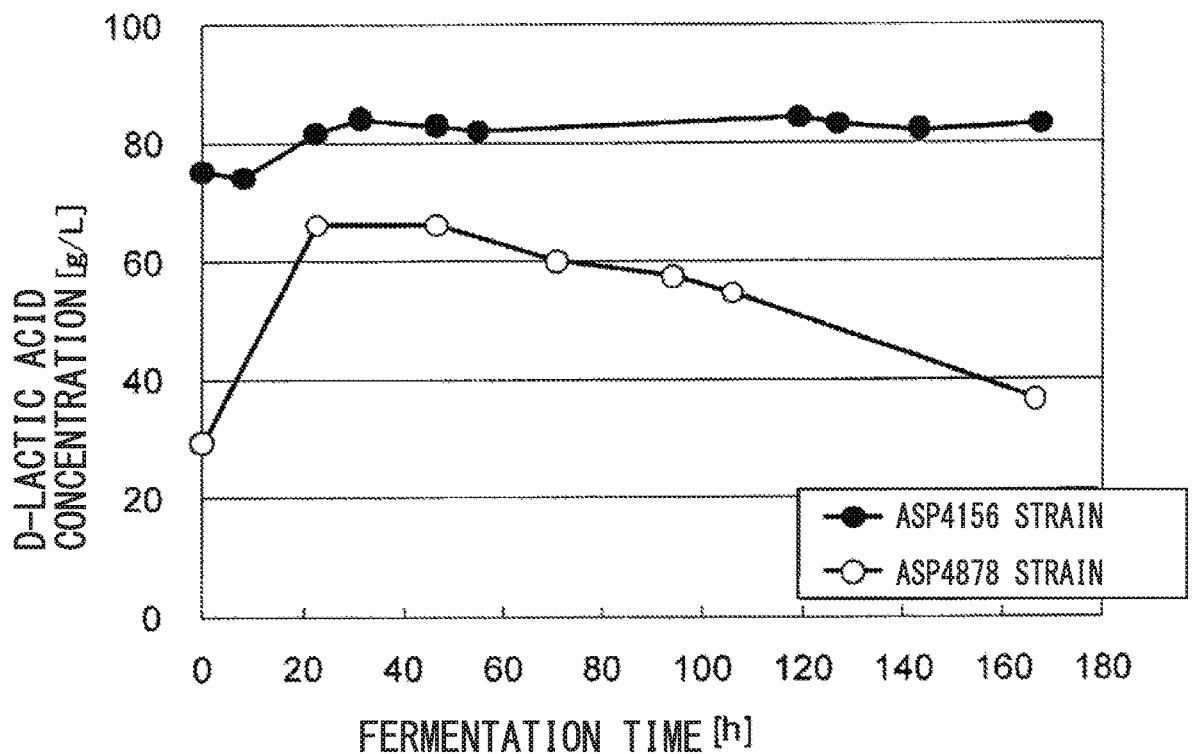
FIG. 8 is a view showing the temporal variation in the D-lactic acid concentration (g/L) in the fermentation solution during the continuous fermentation in Examples 5 and 6.
Figure 9:
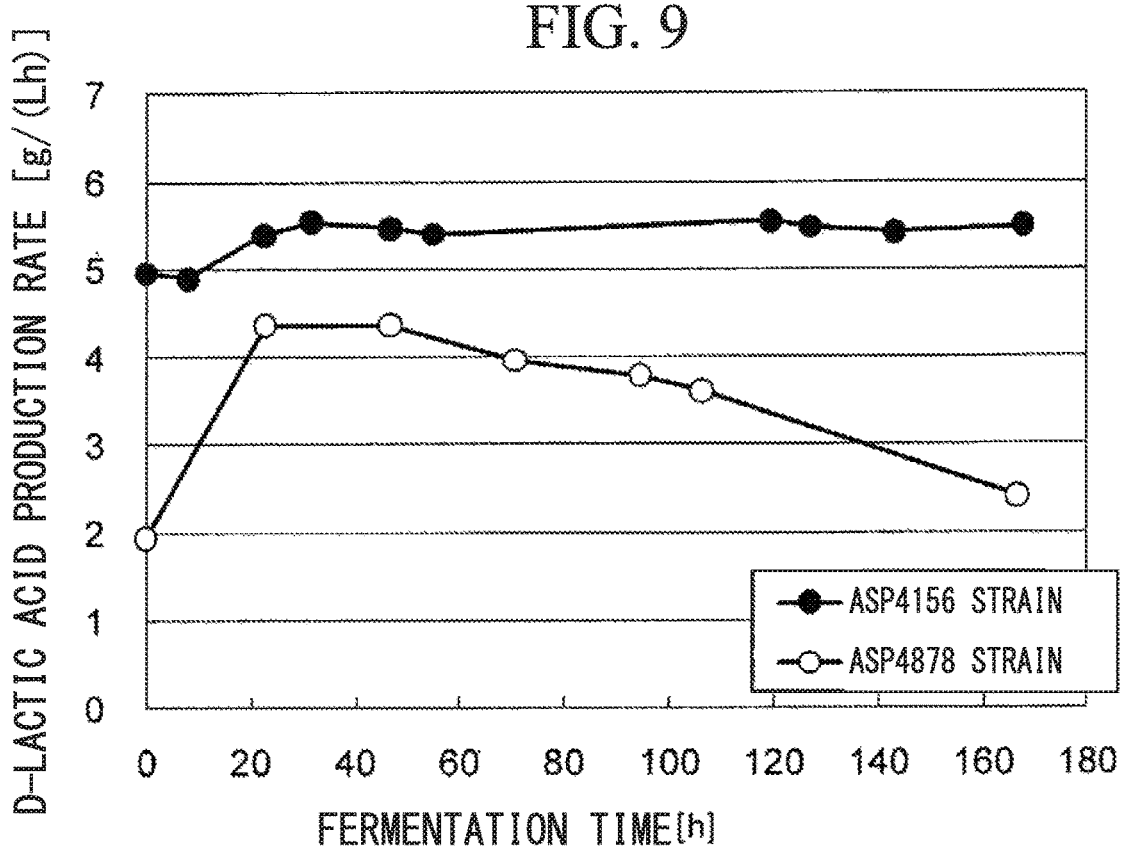
FIG. 9 is a view showing the temporal variation in the D-lactic acid production rate (g/(L·h)) in the fermentation solution during the continuous fermentation in Examples 5 and 6.
Figure 10:
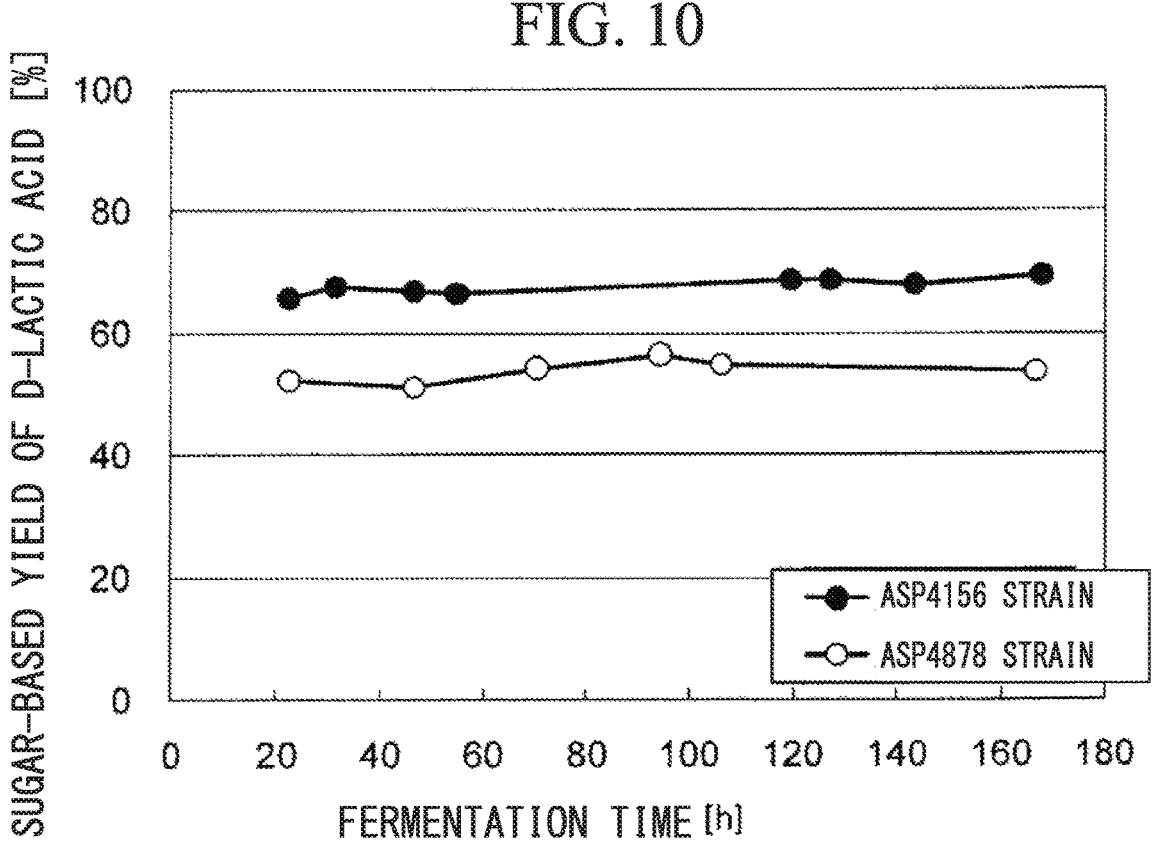
FIG. 10 is a view showing the temporal variation in the sugar-based yield (%) of the D-lactic acid in the fermentation solution during the continuous fermentation in Examples 5 and 6.
Figure 11:
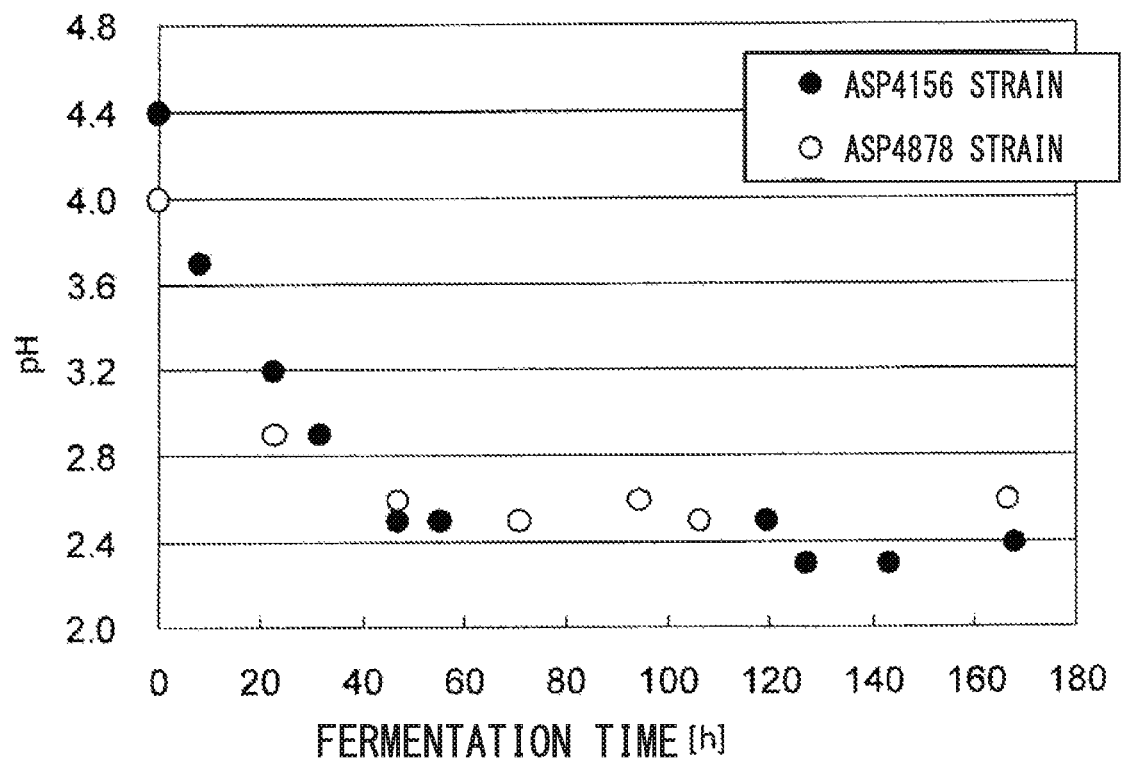
FIG. 11 is a view showing the temporal variation in the pH of the fermentation solution during the continuous fermentation in Examples 5 and 6.
Figure 12:
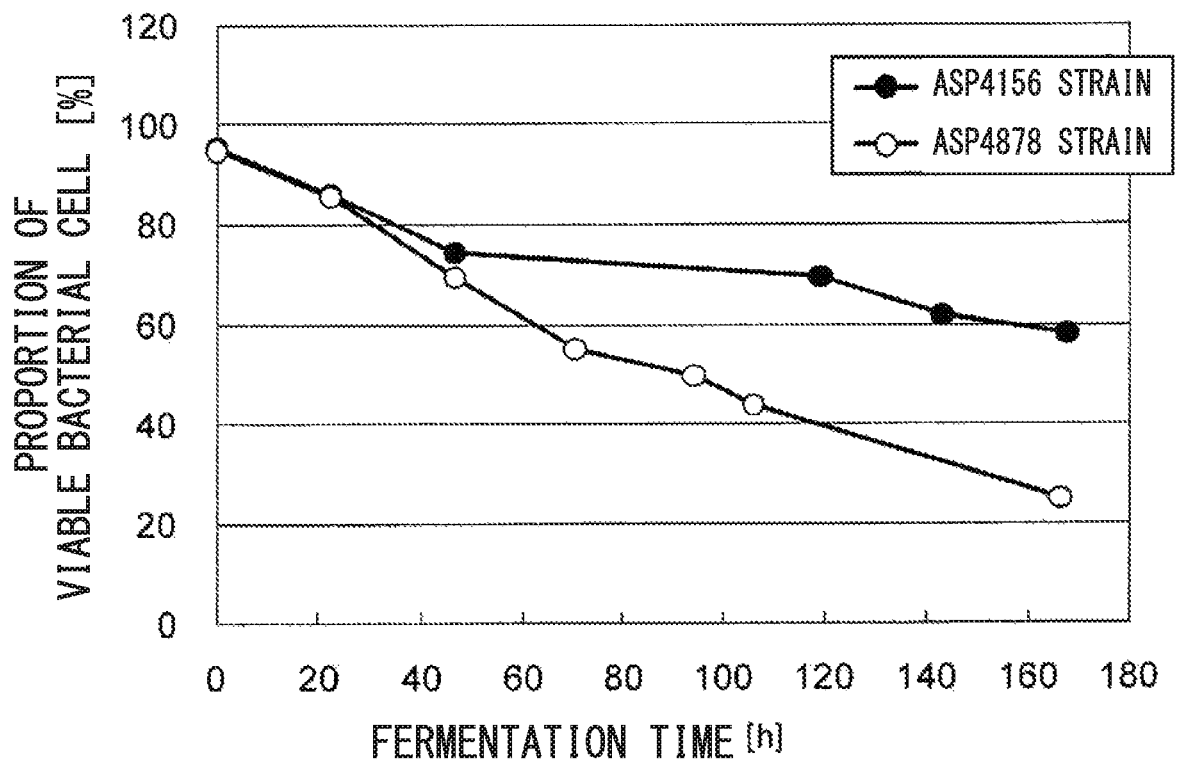
FIG. 12 is a view showing the temporal variation in the proportion of viable bacterial cells in the fermentation solution during the continuous fermentation in Examples 5 and 6.

The results of the continuous fermentation (2) of the ASP4156 strain of Example 6 were compared with the results of the continuous fermentation of the ASP4878 strain of Example 5 so as to investigate the temporal variation in the concentration (g/L) of each of glucose, ethanol, and lactic acid in the fermentation solution. The results are shown in FIGS. 6, 7, and 8. Herein, the lactic acid contained in the fermentation solution from the beginning of fermentation is a fraction of lactic acid produced as a by-product at the stage of fed-batch culture performed for obtaining bacterial cells for lactic acid fermentation. FIGS. 9 and 10 show the temporal variation in the lactic acid production rate (g/(L·h)) and the sugar-based yield (%) of lactic acid, and FIGS. 11 and 12 show the temporal variation in the pH of the fermentation solution and the proportion of viable bacterial cells. The proportion of viable bacterial cells was calculated by mixing the fermentation solution with a trypan blue staining solution in an equal amount and counting the number of stained dead cells and the number of unstained living cells through microscopic observation.

In the ASP4156 strain into which two copies of D-LDH gene were introduced, the lactic acid production rate at a point in time when the fermentation was ended (168 hours of continuous fermentation) was 5.5 g/(L·h), the sugar-based yield of lactic acid was 69%, and the proportion of viable bacterial cells was 58%. In contrast, in the ASP4878 strain into which one copy of D-LDH gene was introduced, the lactic acid production rate at a point in time when the fermentation was ended (166 hours of continuous fermentation) was 2.4 g/(L·h), the sugar-based yield of lactic acid was 54%, and the proportion of viable bacterial cells was 25%. In the ASP4156 strain, the concentration of D-lactic acid was not reduced during the continuous fermentation. However, in the ASP4878 strain, the concentration of D-lactic acid tended to start to be reduced 47 hours after the beginning of the fermentation. Furthermore, the sugar-based yield of lactic acid in the ASP4878 strain was lower by not less than 10% than in the ASP4156 strain, and the proportion of viable bacterial cells tended to be markedly reduced in the ASP4878 strain.

Hitherto, the present invention has been specifically described with reference to specific embodiments. However, as is evident to those in the related art, the present invention can be altered or modified in various ways without departing from the idea and scope of the present invention.

The present application is based on Japanese Patent Application No. 2013-242236, filed Nov. 22, 2013, the content of which is incorporated herein by reference.

The invention claimed is:

1. A *Schizosaccharomyces pombe* transformant into which a D-lactate dehydrogenase gene of bacteria of *Pediococcus acidilactici* and a D-lactate dehydrogenase gene of bacteria of *Lactobacillus bulgaricus* or *Lactobacillus brevis* are incorporated,
wherein pyruvate decarboxylase 2-encoding genes of the *Schizosaccharomyces pombe* transformant have been deleted or inactivated.

2. The *Schizosaccharomyces pombe* transformant according to claim 1,
wherein the D-lactate dehydrogenase gene of bacteria of *Pediococcus acidilactici* and the D-lactate dehydrogenase gene of bacteria of *Lactobacillus bulgaricus* or *Lactobacillus brevis* are incorporated into a chromosome of the *Schizosaccharomyces pombe* transformant.

3. A process for production of a *Schizosaccharomyces pombe* transformant into which a D-lactate dehydrogenase gene of bacteria of *Pediococcus acidilactici* and a D-lactate dehydrogenase gene of bacteria of *Lactobacillus bulgaricus*, or *Lactobacillus brevis* are incorporated and in which pyruvate decarboxylase 2-encoding genes of the *Schizosaccharomyces pombe* transformant have been deleted or inactivated, the process comprising:
a step of obtaining a transformant by introducing an expression cassette into a *Schizosaccharomyces pombe* host,
wherein the expression cassette consists of an expression cassette including a promoter and a terminator functioning in the *Schizosaccharomyces pombe* host and a D-lactate dehydrogenase gene of bacteria of *Pediococcus acidilactici* and an expression cassette including a promoter and a terminator functioning in the *Schizosaccharomyces pombe* host and a D-lactate dehydrogenase gene of bacteria of *Lactobacillus bulgaricus* or *Lactobacillus brevis*, or consists of an expression cassette including a promoter or a terminator functioning in the *Schizosaccharomyces pombe* host, a D-lactate dehydrogenase gene of bacteria of *Pediococcus acidilactici*, and a D-lactate dehydrogenase gene of bacteria of *Lactobacillus bulgaricus* or *Lactobacillus brevis*, and
the *Schizosaccharomyces pombe* host in which pyruvate decarboxylase 2-encoding genes have been deleted or inactivated, or
pyruvate decarboxylase 2-encoding genes of the obtained transformant are deleted or inactivated.

4. The process for production of a *Schizosaccharomyces pombe* transformant according to claim 3,
wherein the D-lactate dehydrogenase gene of bacteria of *Pediococcus acidilactici* and the D-lactate dehydrogenase gene of bacteria of *Lactobacillus bulgaricus* or *Lactobacillus brevis* are introduced into a chromosome of the *Schizosaccharomyces pombe* host.

5. The process for production of lactic acid,
wherein a *Schizosaccharomyces pombe* transformant of claim 1 is cultured or fermented in a culture solution or a fermentation solution, and
D-lactic acid is obtained from the culture solution or the fermentation solution.

6. The process for production of lactic acid according to claim 5,
wherein the culture or the fermentation is performed using a culture solution or a fermentation solution containing glucose or sucrose at a concentration of 1% by mass to 50% by mass.

7. The process for production of lactic acid according to claim 5,
wherein the culture or the fermentation is further continued after the pH of the culture solution or the fermentation solution becomes equal to or less than 3.5 due to the D-lactic acid produced by the *Schizosaccharomyces pombe* transformant.

8. The process for production of lactic acid according to claim 5,
wherein an initial bacterial cell concentration of the *Schizosaccharomyces pombe* transformant in the culture solution or the fermentation solution is set to be 0.1 g/L to 50 g/L (expressed in terms of dry bacterial cells).

9. The process for production of lactic acid according to claim 5,
wherein the culture or the fermentation is continued without neutralizing the D-lactic acid in the culture solution or the fermentation solution that is produced by the *Schizosaccharomyces pombe* transformant.

10. The process for production of lactic acid according to claim 5,
wherein lactic acid is separated from the culture solution or the fermentation solution without neutralizing the D-lactic acid in the culture solution or the fermentation solution that is produced by the *Schizosaccharomyces pombe* transformant.

\* \* \* \* \*

SEQUENCE LISTING

<160> NUMBER OF SEQ ID NOS: 56

<210> SEQ ID NO 1
<211> LENGTH: 21
<212> TYPE: DNA
<213> ORGANISM: Artificial Sequence
<220> FEATURE:
<223> OTHER INFORMATION: Synthesized

<400> SEQUENCE: 1
ctctccagct ccatccataa g                                            21

<210> SEQ ID NO 2
<211> LENGTH: 45
<212> TYPE: DNA
<213> ORGANISM: Artificial Sequence
<220> FEATURE:
<223> OTHER INFORMATION: Synthesized

<400> SEQUENCE: 2
gacacaactt cctaccaaaa agcctttctg cccatgtttt ctgtc                  45

<210> SEQ ID NO 3
<211> LENGTH: 23
<212> TYPE: DNA
<213> ORGANISM: Artificial Sequence
<220> FEATURE:
<223> OTHER INFORMATION: Synthesized

<400> SEQUENCE: 3 gcttttggt aggaagttgt gtc                                           23

<210> SEQ ID NO 4
<211> LENGTH: 43
<212> TYPE: DNA
<213> ORGANISM: Artificial Sequence
<220> FEATURE:
<223> OTHER INFORMATION: Synthesized

<400> SEQUENCE: 4
agtgggattt gtagctaagc tgtatccatt tcagccgttt gtg                    43

<210> SEQ ID NO 5
<211> LENGTH: 45
<212> TYPE: DNA
<213> ORGANISM: Artificial Sequence
<220> FEATURE:
<223> OTHER INFORMATION: Synthesized

<400> SEQUENCE: 5
aagtttcgtc aatatcacaa gctgacagaa acatgggca gaaag                   45

<210> SEQ ID NO 6
<211> LENGTH: 24
<212> TYPE: DNA
<213> ORGANISM: Artificial Sequence
<220> FEATURE:
<223> OTHER INFORMATION: Synthesized

<400> SEQUENCE: 6
gttccttaga aaaagcaact ttgg                                         24

<210> SEQ ID NO 7
<211> LENGTH: 20
<212> TYPE: DNA
<213> ORGANISM: Artificial Sequence

```
<220> FEATURE:
<223> OTHER INFORMATION: Synthesized

<400> SEQUENCE: 7
cataagcttg ccaccacttc                                          20

<210> SEQ ID NO 8
<211> LENGTH: 24
<212> TYPE: DNA
<213> ORGANISM: Artificial Sequence
<220> FEATURE:
<223> OTHER INFORMATION: Synthesized

<400> SEQUENCE: 8
gaaaaagcaa ctttggtatt ctgc                                     24

<210> SEQ ID NO 9
<211> LENGTH: 21
<212> TYPE: DNA
<213> ORGANISM: Artificial Sequence
<220> FEATURE:
<223> OTHER INFORMATION: Synthesized

<400> SEQUENCE: 9
agcttagcta caaatcccac t                                        21

<210> SEQ ID NO 10
<211> LENGTH: 23
<212> TYPE: DNA
<213> ORGANISM: Artificial Sequence
<220> FEATURE:
<223> OTHER INFORMATION: Synthesized

<400> SEQUENCE: 10
agcttgtgat attgacgaaa ctt                                      23

<210> SEQ ID NO 11
<211> LENGTH: 33
<212> TYPE: DNA
<213> ORGANISM: Artificial Sequence
<220> FEATURE:
<223> OTHER INFORMATION: Synthesized

<400> SEQUENCE: 11
tctcaacata tggatgctag agtatttcaa agc                           33

<210> SEQ ID NO 12
<211> LENGTH: 32
<212> TYPE: DNA
<213> ORGANISM: Artificial Sequence
<220> FEATURE:
<223> OTHER INFORMATION: Synthesized

<400> SEQUENCE: 12
agcagctcta gaggtaatgt tgtaggagca tg                            32

<210> SEQ ID NO 13
<211> LENGTH: 34
<212> TYPE: DNA
<213> ORGANISM: Artificial Sequence
<220> FEATURE:
<223> OTHER INFORMATION: Synthesized

<400> SEQUENCE: 13
agcagatatc gtttaaacca cgtggatatc agca                          34
```

<210> SEQ ID NO 14
<211> LENGTH: 27
<212> TYPE: DNA
<213> ORGANISM: Artificial Sequence
<220> FEATURE:
<223> OTHER INFORMATION: Synthesized

<400> SEQUENCE: 14
tagatatcag gataggctag tgaatgt                                   27

<210> SEQ ID NO 15
<211> LENGTH: 30
<212> TYPE: DNA
<213> ORGANISM: Artificial Sequence
<220> FEATURE:
<223> OTHER INFORMATION: Synthesized

<400> SEQUENCE: 15
tagtttaaac ggcttcggat taccaacaaa                                30

<210> SEQ ID NO 16
<211> LENGTH: 41
<212> TYPE: DNA
<213> ORGANISM: Artificial Sequence
<220> FEATURE:
<223> OTHER INFORMATION: Synthesized

<400> SEQUENCE: 16
tagctagcgt ttaaacacgt gcaaatctct gctggttact c                   41

<210> SEQ ID NO 17
<211> LENGTH: 28
<212> TYPE: DNA
<213> ORGANISM: Artificial Sequence
<220> FEATURE:
<223> OTHER INFORMATION: Synthesized

<400> SEQUENCE: 17
tagctagcac attcactagc ctatcctg                                  28

<210> SEQ ID NO 18
<211> LENGTH: 7180
<212> TYPE: DNA
<213> ORGANISM: Artificial Sequence
<220> FEATURE:
<223> OTHER INFORMATION: Synthesized

<400> SEQUENCE: 18
gaattgttgt tgttaacttg tttattgcag cttataatgg ttacaaataa agcaatagca    60
tcacaaattt cacaaataaa gcattttttt cactgcattc tagttgtggt ttgtccaaac   120
tcatcaatgt atcttatcat gtctggatcg atcccggcag gttgggcgtc gcttggtcgg   180
tcatttcgaa ccccagagtc ccgctcagaa gaactcgtca agaaggcgat agaaggcgat   240
gcgctgcgaa tcgggagcgg cgataccgta aagcacgagg aagcggtcag cccattcgcc   300
gccaagctct tcagcaatat cacgggtagc caacgctatg tcctgatagc ggtccgccac   360
acccagccgg ccacagtcga tgaatccaga aaagcggcca ttttccacca tgatattcgg   420
caagcaggca tcgccatggg tcacgacgag atcctcgccg tcgggcatgc gcgccttgag   480
cctggcgaac agttcggctg cgcgagccc ctgatgctct tcgtccagat catcctgatc   540
gacaagaccg gcttccatcc gagtacgtgc tcgctcgatg cgatgtttcg cttggtggtc   600
gaatgggcag gtagccggat caagcgtatg cagccgccgc attgcatcag ccatgatgga   660

```
tactttctcg gcaggagcaa ggtgagatga caggagatcc tgccccggca cttcgcccaa      720
tagcagccag tcccttcccg cttcagtgac aacgtcgagc acagctgcgc aaggaacgcc      780
cgtcgtggcc agccacgata gccgcgctgc ctcgtcctgc agttcattca gggcaccgga      840
caggtcggtc ttgacaaaaa gaaccgggcg cccctgcgct gacagccgga acacggcggc      900
atcagagcag ccgattgtct gttgtgccca gtcatagccg aatagcctct ccacccaagc      960
ggccggagaa cctgcgtgca atccatcttg ttcaatcatg cgaaacgatc ctcatcctgt     1020
ctcttgatca gatccgggac ctgaaataaa agacaaaaag actaaactta ccagttaact     1080
ttctggtttt tcagttcctc gaggagcttt ttgcaaaagc ctaggcctcc aaaaaagcct     1140
cctcactact tctggaatag ctcagaggcc gaggcggcct cggcctctgc ataaataaaa     1200
aaaattagtc agccatgggg cggagaatgg gcggaactgg gcggagttag gggcgggatg     1260
ggcggagtta ggggcgggac tatggttgct gactaattga gatgcatgct ttgcatactt     1320
ctgcctgctg gggagcctgg ggactttcca cacctggttg ctgactaatt gagatgcatg     1380 cttttgcatac ttctgcctgc tggggagcct ggggactttc cacaccctaa ctgacacaca     1440
ttccacagga cattgattat tgactagcgt ttaaacacgt gcaaatctct gctggttact     1500
ctcctgtttt ggattgccac actgctcaca ttgcttgcaa gttcgctgag ctcattgaga     1560
agattgaccg tcgttccggt aagaagattg aggagtcccc caagtttgtc aagtctggtg     1620
atgcttgcat tgctaagatg gttccttcca gcctatgtg tgttgaagct ttcactgact      1680
acgctcctct tggtcgtttc gctgtccgtg acatgcgtca aaccgtcgct gtcggtgtca     1740
tcaaggccgt tgagaaggtt gcccctggtg ccgctaaggt cactaaggcc gctgttaagg     1800
ctggcgccaa gaagtaaaca tttttactt cggatttaag tagatcttga gttgttgtaa      1860
tcaggatagg ctagtgaatg tgctagttat taatagtaat caattacggg gtcattagtt     1920
catagcccat atatgagtt ccgcgttaca aacttacgg taaatggccc gcctggctga       1980
ccgcccaacg acccccgccc attgacgtca ataatgacgt atgttcccat agtaacgcca     2040
atagggactt tccattgacg tcaatgggtg gagtatttac ggtaaactgc ccacttggca     2100
gtacatcaag tgtatcatat gccaagtacg ccccctattg acgtcaatga cggtaaatgg     2160
cccgcctggc attttgccca gtacatgacc ttatgggact ttcctacttg gcagtacatc     2220
tacgtattag tcatcgctat taccatggtg atgcggtttt ggcagtacat caatgggcgt     2280
ggatagcggt ttgactcacg ggatttcca agtctccacc ccattgacgt caatgggagt      2340
ttgttttggc accaaaatca acgggacttt ccaaaatgtc gtaacaactc cgccccattg     2400
acgcaaatgg gcggtaggcg tgtacggtgg gaggtctata taagcagatt tctctttagt     2460
tctttgcaag aaggtagaga taagacact ttttcaaata tggatgctag agtatttcaa      2520
agctattcag ctagagctga ggggatgaaa atcccattg ccaaggaatt gttggctttg      2580
atggaagaaa agcaaagcaa cttgtcagtc gcggtcgatt tgacgaagaa atccgaaatc     2640
ttagaattgg tagataaaat tggaccctat gtctgtgtta tcaagacaca tattgacgtt     2700
gtcgaggatt tcgaccagga tatggtagaa aaactggtgg ccttaggtaa aaagcatcgt     2760
tttcttatct ttgaggatcg caaattcgca gacattggaa ataccgtcaa gctacaatat     2820
gcatctggtg tgtacaaaat tgcttcttgg gctcatatca caaattgcca tacagtgcca     2880
ggcgagggta ttatacaagg cctcaaagaa gttggtttac cttgggacg tggtctcttg      2940 cttttggctg aaatgtcttc caaaggctct ttggctactg gttcctacac agagaaaacc     3000
```

```
ttagaatggt ttgagaagca taccgatttt tgctttggct ttatagctgg tcgtcgattt    3060
cctaaccttc aaagcgacta cataactatg tccctggta tcggcttgga tgttaaagga      3120
gacgggctgg gacagcaata tcgtactcct gaagaagtga ttgtaaactg cggtagcgat    3180
atcatcattg ttggtcgtgg agtctatgga gctggtcgta atcctgttgt cgaagccaag    3240
agatatagag aagctggttg gaaggcatat cagcaaagac tttctcagca ttaaaaaaag    3300
actaatgtaa aatttttttg gttggttatt gaaaaagtcg atgccttgtt tgcgtttgtt    3360
ttcctaggcg tttatgtca gaaggcattt agaattagta tacaagtact ctttggtaaa     3420
attttatgta gcgactaaaa tattaactat tatagataaa caccttggga ataaaaagta    3480
atttgctata gtaatttatt aaacatgctc ctacaacatt acctctagtt attaatagta    3540
atcaattacg gggtcattag ttcatagccc atatatggag ttccgcgtta cataacttac    3600
ggtaaatggc ccgcctggct gaccgcccaa cgacccccgc ccattgacgt caataatgac    3660
gtatgttccc atagtaacgc caatagggac tttccattga cgtcaatggg tggagtattt    3720
acggtaaact gcccacttgg cagtacatca agtgtatcat atgccaagta cgccccctat    3780
tgacgtcaat gacggtaaat ggcccgcctg gcattttgcc cagtacatga ccttatggga    3840 cttcctact tggcagtaca tctacgtatt agtcatcgct attaccatgg tgatgcggtt       3900
ttggcagtac atcaatgggc gtggatagcg gtttgactca cggggatttc caagtctcca    3960
ccccattgac gtcaatggga gtttgttttg gcaccaaat caacgggact ttccaaaatg     4020
tcgtaacaac tccgccccat tgacgcaaat gggcggtagg cgtgtacggt gggaggtcta    4080
tataagcaga tttctctttta gttctttgca agaaggtaga gataaagaca ctttttcaaa    4140
catgtgaatt cgagctcggt acccggggat cctctagagt cgacctgcag gcatgcaagc    4200
ttaaatagga aagtttcttc aacaggatta cagtgtagct acctacatgc tgaaaaatat    4260
agcctttaaa tcatttttat attataactc tgtataatag agataagtcc attttttaaa    4320
aatgttttcc ccaaaccata aaccctata caagttgttc tagtaacaat acatgagaaa     4380
gatgtctatg tagctgaaaa taaaatgacg tcacaagacg atctgcctcg cgcgtttcgg    4440
tgatgacggt gaaaacctct gacacatgca gctcccggag acggtcacag cttgtctgta    4500
agcggatgcc gggagcagac aagcccgtca gggcgcgtca gcgggtgttg gcgggtgtcg    4560
gggcgcagcc atgacccagt cacgtagcga tagcggagtg taatcgttta tcaggatagg    4620
ctagtgaatg ttatattgtt gattaatata atttggtata ctactcagta attaaattta    4680
cttataactt aggaattgaa atttaaattg catggttaaa tatagatttg caacgataat    4740
tctttttttc attttttaag tgcaaaatat gtatatgtag aactaagtgc gtacatatgg    4800
aggactttga ataggtgtcg gagacatagc acgattaaga ttcaacatat caagcagagg    4860
tacacggttg ctcgtttgtc ttgtaagatt tatttccgac ggagaacgta cgacagtact    4920
agcagtgtgt ggccttgata gagcctgttt caatgtgcta accatttctc cacgttgtga    4980
ttgctggtga atagaaacga gcgacttggt agcatgaagt aaaggatttt gttggtaatc    5040
cgaagccgtt taaccacgt ggattactgg cttaactatg cggcatcaga gcagattgta     5100
ctgagagtgc accatatgcg gtgtgaaata ccgcacagat gcgtaaggag aaaataccgc    5160
atcaggcgct cttccgcttc ctcgctcact gactcgctgc gctcggtcgt tcggctgcgg    5220
cgagcggtat cagctcactc aaaggcggta atacggttat ccacagaatc agggggataac    5280 gcaggaaaga acatgcatgt gagcaaaagg ccagcaaaag gccaggaacc gtaaaaaggc    5340
cgcgttgctg gcgtttttcc ataggctccg ccccctgac gagcatcaca aaaatcgacg     5400
```

```
ctcaagtcag aggtggcgaa acccgacagg actataaaga taccaggcgt ttccccctgg    5460
aagctccctc gtgcgctctc ctgttccgac cctgccgctt accggatacc tgtccgcctt    5520
tctcccttcg ggaagcgtgg cgctttctca tagctcacgc tgtaggtatc tcagttcggt    5580
gtaggtcgtt cgctccaagc tgggctgtgt gcacgaaccc cccgttcagc ccgaccgctg    5640
cgccttatcc ggtaactatc gtcttgagtc caacccggta agacacgact tatcgccact    5700
ggcagcagcc actggtaaca ggattagcag agcgaggtat gtaggcggtg ctacagagtt    5760
cttgaagtgg tggcctaact acggctacac tagaaggaca gtatttggta tctgcgctct    5820
gctgaagcca gttaccttcg gaaaaagagt tggtagctct tgatccggca aacaaaccac    5880
cgctggtagc ggtggttttt ttgtttgcaa gcagcagatt acgcgcagaa aaaaggatc    5940 tcaagaagat cctttgatct tttctacggg gtctgacgct cagtggaacg aaaactcacg    6000
ttaagggatt ttggtcatga gattatcaaa aaggatcttc acctagatcc ttttaaatta    6060
aaaatgaagt tttaaatcaa tctaaagtat atatgagtaa acttggtctg acagttacca    6120
atgcttaatc agtgaggcac ctatctcagc gatctgtcta tttcgttcat ccatagttgc    6180
ctgactcccc gtcgtgtaga taactacgat acgggagggc ttaccatctg gccccagtgc    6240
tgcaatgata ccgcgagacc cacgctcacc ggctccagat ttatcagcaa taaaccagcc    6300
agccggaagg gccgagcgca gaagtggtcc tgcaacttta tccgcctcca tccagtctat    6360
taattgttgc cgggaagcta gagtaagtag ttcgccagtt aatagtttgc gcaacgttgt    6420
tgccattgct gcaggcatcg tggtgtcacg ctcgtcgttt ggtatggctt cattcagctc    6480
cggttcccaa cgatcaaggc gagttacatg atcccccatg ttgtgcaaaa aagcggttag    6540
ctccttcggt cctccgatcg ttgtcagaag taagttggcc gcagtgttat cactcatggt    6600
tatggcagca ctgcataatt ctcttactgt catgccatcc gtaagatgct tttctgtgac    6660
tggtgagtac tcaaccaagt cattctgaga atagtgtatg cggcgaccga gttgctcttg    6720
cccggcgtca acacgggata ataccgcgcc acatagcaga actttaaaag tgctcatcat    6780
tggaaaacgt tcttcggggc gaaaactctc aaggatctta ccgctgttga gatccagttc    6840
gatgtaaccc actcgtgcac ccaactgatc ttcagcatct tttactttca ccagcgtttc    6900
tgggtgagca aaaacaggaa ggcaaaatgc cgcaaaaaag ggaataaggg cgacacggaa    6960
atgttgaata ctcatactct tcctttttca atattattga agcatttatc agggttattg    7020
tctcatgagc ggatacatat ttgaatgtat ttagaaaaat aaacaaatag gggttccgcg    7080
cacatttccc cgaaaagtgc cacctgacgt ctaagaaacc attattatca tgacattaac    7140
ctataaaaat aggcgtatca cgaggccctt tcgtcttcaa                           7180
```

<210> SEQ ID NO 19
<211> LENGTH: 1101
<212> TYPE: DNA
<213> ORGANISM: Artificial Sequence
<220> FEATURE:
<223> OTHER INFORMATION: Synthesized

<400> SEQUENCE: 19

```
tggcagtaca tctacgtatt agtcatcgct attaccatgg tgatgcggtt ttggcagtac      60
atcaatgggc gtggatagcg gtttgactca cggggatttc caagtctcca ccccattgac     120
gtcaatggga gtttgttttg gcaccaaaat caacgggact ttccaaaatg tcgtaacaac     180
tccgccccat tgacgcaaat gggcggtagg cgtgtacggt gggaggtcta taagcaga     240
```

```
tttctctttta gttctttgca agaaggtaga gataaagaca cttttttcaaa catgtaaagc    300 aggtgtcagg gcgatggccc actacgtgaa ccatcaccct aatcaagttt tttggggtcg    360
aggtgccgta aagcactaaa tcggaaccct aaagggagcc cccgatttag agcttgacgg    420
ggaaagccgg cgaacgtggc gagaaaggaa gggaagaaag cgaaaggagc gggcgctagg    480
gcgctggcaa gtgtagcggt cacgctgcgc gtaaccacca cacccgccgc gcttaatgcg    540
ccgctacagg gcgcgtccca ttcgccattc aggctgcgca actgttggga agggcgatcg    600
gtgcgggcct cttcgctatt acgccagctg gcgaaagggg gatgtgctgc aaggcgatta    660
agttgggtaa cgccagggtt ttcccagtca cgacgttgta aaacgacggc cagtgagcgc    720
gcgtaatacg actcactata gggcgaattg gagctccacc gcggtggcgg ccgctctaga    780
actagtggat ccccccgggct gcaggaattc gatatcaagc ttatcgatac cgtcgacctc    840
gagggggggc ccggtaccca gcttttgttc cctttagtga gggttaattg cgcgcttggc    900
gtaatcatgg tcatagctgt ttcctgtgtg aaattgttat ccgctcacaa ttccacacaa    960
catacgagcc gggagcataa agtgtaaagc ctggggtgcc taatgagtga gctaactcac    1020
attaattgcg ttgcgccatg tgaagcaggt gtcggtaccg attacaagga tgatgatgat    1080
aagtaacggg gatcctctag a                                              1101
```

<210> SEQ ID NO 20
<211> LENGTH: 27
<212> TYPE: DNA
<213> ORGANISM: Artificial Sequence
<220> FEATURE:
<223> OTHER INFORMATION: Synthesized

<400> SEQUENCE: 20

```
tggcagtaca tctacgtatt agtcatc                                         27
```

<210> SEQ ID NO 21
<211> LENGTH: 62
<212> TYPE: DNA
<213> ORGANISM: Artificial Sequence
<220> FEATURE:
<223> OTHER INFORMATION: Synthesized

<400> SEQUENCE: 21

```
tctagaggat ccccgttact tatcatcatc atccttgtaa tcggtaccga cacctgcttc    60
ac                                                                    62
```

<210> SEQ ID NO 22
<211> LENGTH: 30
<212> TYPE: DNA
<213> ORGANISM: Artificial Sequence
<220> FEATURE:
<223> OTHER INFORMATION: Synthesized

<400> SEQUENCE: 22

```
aaatcgtacg cctagcagcg aatccaaacc                                      30
```

<210> SEQ ID NO 23
<211> LENGTH: 25
<212> TYPE: DNA
<213> ORGANISM: Artificial Sequence
<220> FEATURE:
<223> OTHER INFORMATION: Synthesized

<400> SEQUENCE: 23

```
atatacgtac gggatggctg cggag                                           25
```

<210> SEQ ID NO 24
<211> LENGTH: 5936
<212> TYPE: DNA
<213> ORGANISM: Artificial Sequence
<220> FEATURE:
<223> OTHER INFORMATION: Synthesized

<400> SEQUENCE: 24

```
aacccacaga ggtagaatgt atatataaaa ttaataagct aagtgtaata cttaaaaaat     60
acattaattg gaactcgtat cctaccattt acaatgttca tccaattttt tcagattgta    120
ctgtaaatag cgtttgaaaa caccaaattt tagaagctaa tcactctcat cataatcgtc    180
tacatcctca tcgttatcga cgataaaaga atcatcttgc atgctgggtt catccatgct    240
atcaaacgag ggatcaacgt aaataggtgt tttcactgta gccgctgctc ttctggttgg    300 cctcttttcta atcggagaat ctgaatcttc tggtggctct gcgttagtcg aactagcttt    360
tggagttgaa ctactacctg gaataataaa atcatcatcg tcatcttcag gtgattgttt    420
ctttaccgag cttgcttttt tcccttttat cttcgcagaa gccttcgtgg atgttatggt    480
ggaaggtttc aaactgctag caacaaatc atcttcatcg tctgaagaaa atatggtagt    540
agcaactggt ttattagtct ttcttcctct tccagacgcc gaggctgcta ttttttttgac    600 gggtttttta ctacctgcgt cttcagagtc aacagattga cttcttttc ttgatttttcc    660 actatcactg ctatccaatc ccgggctctt agatatgcga ttttcttcaa ctgataagcc    720
atgagagtta tcctctgtct tgacaatgtt tatgtcagat gatttctcag gttctttcga    780
cgctgcgaac tcaagtaaag tttgttgctt tcgatttgtt gtagatggtt tggattcgct    840
gctaggcgta cgatttaaat gcggccgcaa caacaattct tgaagacgaa agggcctcgt    900
gatacgccta ttttttatagg ttaatgtcat gataataatg gtttcttaga cgtcaggtgg    960
cacttttcgg ggaaatgtgc gcggaaccc tatttgttta ttttttctaaa tacattcaaa   1020 tatgtatccg ctcatgagac aataacctg ataaatgctt caataatatt gaaaaggaa   1080 gagtatgagt attcaacatt tccgtgtcgc ccttattcc tttttttgcgg catttttgcct   1140 tcctgttttt gctcacccag aaacgctggt gaaagtaaaa gatgctgaag atcagttggg   1200
tgcacgagtg ggttacatcg aactggatct caacagcggt aagatccttg agagtttcg   1260 ccccgaagaa cgttttccaa tgatgagcac ttttaaagtt ctgctatgtg gcgcggtatt   1320
atcccgtgtt gacgccgggc aagagcaact cggtcgccgc atacactatt ctcagaatga   1380
cttggttgag tactcaccag tcacagaaaa gcatcttacg gatggcatga cagtaagaga   1440
attatgcagt gctgccataa ccatgagtga taacactgcg gccaacttac ttctgacaac   1500
gatcggagga ccgaaggagc taaccgcttt tttgcacaac atgggggatc atgtaactcg   1560
ccttgatcgt tgggaaccgg agctgaatga agccatacca aacgacgagc gtgacaccac   1620
gatgcctgca gcaatggcaa caacgttgcg caaactatta actggcgaac tacttactct   1680
agcttcccgg caacaattaa tagactggat ggaggcggat aaagttgcag gaccacttct   1740
gcgctcggcc cttccggctg gctggtttat tgctgataaa tctggagccg gtgagcgtgg   1800
gtctcgcggt atcattgcag cactggggcc agatggtaag ccctcccgta tcgtagttat   1860
ctacacgacg gggagtcagg caactatgga tgaacgaaat agacagatcg ctgagatagg   1920
tgcctcactg attaagcatt ggtaactgtc agaccaagtt tactcatata ctttagat   1980 tgatttaaaa cttcattttt aatttaaaag gatctaggtg aagatccttt ttgataatct   2040
```

```
catgaccaaa atcccttaac gtgagttttc gttccactga gcgtcagacc ccgtagaaaa    2100
gatcaaagga tcttcttgag atccttttt tctgcgcgta atctgctgct tgcaaacaaa    2160
aaaaccaccg ctaccagcgg tggtttgttt gccggatcaa gagctaccaa ctctttttcc    2220
gaaggtaact ggcttcagca gagcgcagat accaaatact gtccttctag tgtagccgta    2280
gttaggccac cacttcaaga actctgtagc accgcctaca tacctcgctc tgctaatcct    2340
gttaccagtg ctgctgcca gtggcgataa gtcgtgtctt accgggttgg actcaagacg    2400
atagttaccg gataaggcgc agcggtcggg ctgaacgggg ggttcgtgca cacagcccag    2460
cttggagcga acgacctaca ccgaactgag atacctacag cgtgagctat gagaaagcgc    2520
cacgcttccc gaagggagaa aggcggacag gtatccggta agcggcaggg tcggaacagg    2580
agagcgcacg agggagcttc cagggggaaa cgcctggtat ctttatagtc ctgtcgggtt    2640
tcgccacctc tgacttgagc gtcgattttt gtgatgctcg tcagggggc ggagcctatg    2700 gaaaaacgcc agcaacgcgg cctttttacg gttcctggcc ttttgctggc cttttgctca    2760
catgcatgtt ctttcctgcg ttatcccctg attctgtgga taaccgtatt accgcctttg    2820
agtgagctga taccgctcgc cgcagccgaa cgaccgagcg cagcgagtca gtgagcgagg    2880
aagcggaaga gcgcctgatg cggtattttc tccttacgca tctgtgcggt atttcacacc    2940
gcatatggtg cactctcagt acaatctgct ctgatgccgc atagttaagc catttaaatg    3000
cggccgccgt acgggatggc tgcggagtca atgagctggt tttttaaggt aaggtgagga    3060
tattcctcct taaaaatctt agctacagtc ttgcgccaaa gacgagaagt tgccaaaaca    3120
ttagctttgt cgagtaatgt gacgggagca ggagggttgg aagtttcagc taaccaagca    3180
gccaaacgag caatacgaga aacttcttcc aaactgtaag gccaagtgtc catagcataa    3240
cccgatccgt tgtcctcagt gcgctcacca agtaacaac ctccagtaag ttctcgtaca    3300
acacaaaaat cgacaccttc aacgatttca ggcttcaaag gctgtactt gactaaagac    3360 ttgctggcaa agttgcaagg tcgaaggttg gcccaaacac ccatactctt acgaagcttc    3420
aataaacctt gctcaggacg acaattgggg ttggtccatt caggaccacc aacggcaccc    3480
aaaagaacac cgtcagcttc caaacaagcc ttcacagtct cgtcagtcaa agggttcca    3540 taggcatcaa tagaggcacc tccaatcttg tgttcttcaa actcgagttt taactcaggt    3600
cgcttcttct caacgacttt caaaacctcc aaggcagaag caacaatttc agggccaata    3660
tggtctcctg gtaagacgac gattttcttt gcacacatgt tgttgaagaa gttttgttgt    3720
gaaatggttt cgtgaaagtt tcagacccta ccgcaaaaat gcctggtttc gggaaactca    3780
acactgttgc acttttata ctacagattg ggatatcgat aatattgcgt aaaaaatcct    3840 tttttaaaa agcttgttta cagtaacgta aatgaccaga atcagatga aaatcacaag    3900 aaagcaaata attcacgtta atcctgata tgtttgattt tgtgatgaaa tcatggatgt    3960
tcataggaat tgttgaaatt gcgcttttt aacgaaatat acaagtatcc tggagcttac    4020
ttaattaatt aatgaatctt tgttcctagg cccgggctag taatcaatta cggggtcatt    4080
agttcatagc ccatatatgg agttccgcgt tacataactt acggtaaatg gcccgcctgg    4140
ctgaccgccc aacgaccccc gcccattgac gtcaataatg acgtatgttc ccatagtaac    4200
gccaataggg actttccatt gacgtcaatg ggtggagtat ttacggtaaa ctgcccactt    4260
ggcagtacat caagtgtatc atatgccaag tacgcccccct attgacgtca atgacggtaa    4320
atggcccgcc tggcattttg cccagtacat gaccttatgg gactttccta cttggcagta    4380
catctacgta ttagtcatcg ctattaccat ggtgatgcgg ttttggcagt acatcaatgg    4440
```

```
gcgtggatag cggtttgact cacggggatt tccaagtctc cacccccattg acgtcaatgg     4500 gagtttgttt tggcaccaaa atcaacggga ctttccaaaa tgtcgtaaca actccgcccc     4560
attgacgcaa atgggcggta ggcgtgtacg gtgggaggtc tatataagca gatttctctt     4620
tagttctttg caagaaggta gagataaaga cactttttca aacatgtaaa gcaggtgtca     4680
gggcgatggc ccactacgtg aaccatcacc ctaatcaagt tttttggggt cgaggtgccg     4740
taaagcacta aatcggaacc ctaaagggag cccccgattt agagcttgac ggggaaagcc     4800
ggcgaacgtg gcgagaaagg aagggaagaa agcgaaagga gcgggcgcta gggcgctggc     4860
aagtgtagcg gtcacgctgc gcgtaaccac cacacccgcc gcgcttaatg cgccgctaca     4920
gggcgcgtcc cattcgccat tcaggctgcg caactgttgg aagggcgat cggtgcgggc     4980 ctcttcgcta ttacgccagc tggcgaaagg gggatgtgct gcaaggcgat taagttgggt     5040
aacgccaggg ttttcccagt cacgacgttg taaaacgacg ccagtgagc gcgcgtaata     5100 cgactcacta tagggcgaat ggagctcca ccgcggtggc ggccgctcta gaactagtgg     5160
atccccgggg ctgcaggaat tcgatatcaa gcttatcgat accgtcgacc tcgaggggggg     5220 gcccggtacc cagcttttgt tccctttagt gagggttaat tgcgcgcttg gcgtaatcat     5280
ggtcatagct gtttcctgtg tgaaattgtt atccgctcac aattccacac aacatacgag     5340 ccggagcat aaagtgtaaa gcctggggtg cctaatgagt gagctaactc acattaattg     5400
cgttgcgcca tgtgaagcag gtgtcggtac cgattacaag gatgatgatg ataagtaacg     5460
gggatcctct agagtcgacc tgcaggcatg caagcttaaa taggaaagtt tcttcaacag     5520
gattacagtg tagctaccta catgctgaaa aatatagcct ttaaatcatt tttatattat     5580
aactctgtat aatagagata agtccatttt ttaaaaatgt tttccccaaa ccataaaacc     5640
ctatacaagt tgttctagta acaatacatg agaaagatgt ctatgtagct gaaaatagaa     5700
tgacgtcaca agacgatctg cctcgcgcgt ttcggtgatg acggtgaaaa cctctgacac     5760
atgcagctcc cggagacggt cacagcttgt ctgtaagcgg atgccgggag cagacaagcc     5820
cgtcagggcg cgtcagcggg tgttggcggg tgtcggggcg cagccatgac ccagtcacgt     5880
agcgatagcg gagcccgggc actagtgaat tcgagtatgt gtacgagttg tcttta        5936
```

<210> SEQ ID NO 25
<211> LENGTH: 45
<212> TYPE: DNA
<213> ORGANISM: Artificial Sequence
<220> FEATURE:
<223> OTHER INFORMATION: Synthesized

<400> SEQUENCE: 25
gacacttttt caaacatgaa gattattgct tatggaattc gtgac                          45

<210> SEQ ID NO 26
<211> LENGTH: 57
<212> TYPE: DNA
<213> ORGANISM: Artificial Sequence
<220> FEATURE:
<223> OTHER INFORMATION: Synthesized

<400> SEQUENCE: 26
atcatcatca tccttgtaat cctcaaactt aacttcattc tttgaagaat tcttttc            57

<210> SEQ ID NO 27
<211> LENGTH: 331
<212> TYPE: PRT

<213> ORGANISM: Pediococcus acidilactici
<220> FEATURE:
<223> OTHER INFORMATION: PaDLDH

<400> SEQUENCE: 27

Met Lys Ile Ile Ala Tyr Gly Ile Arg Asp Asp Glu Lys Pro Tyr Leu
                 5                  10                  15
Asp Glu Trp Val Thr Lys Asn His Ile Glu Val Lys Ala Val Pro Asp
                20                  25                  30
Leu Leu Asp Ser Ser Asn Ile Asp Leu Ala Lys Asp Tyr Asp Gly Val
                35                  40                  45
Val Ala Tyr Gln Gln Lys Pro Tyr Thr Ala Asp Leu Phe Asp Lys Met
 50                  55                  60
His Glu Phe Gly Ile His Ala Phe Ser Leu Arg Asn Val Gly Leu Asp
 65                  70                  75                  80
Asn Val Pro Ala Asp Ala Leu Lys Lys Asn Asp Ile Lys Ile Ser Asn
                 85                  90                  95
Val Pro Ala Tyr Ser Pro Arg Ala Ile Ala Glu Leu Ser Val Thr Gln
                100                 105                 110
Leu Leu Ala Leu Leu Arg Lys Ile Pro Glu Phe Glu Tyr Lys Met Ala
                115                 120                 125
His Gly Asp Tyr Arg Trp Glu Pro Asp Ile Gly Leu Glu Leu Asn Gln
                130                 135                 140
Met Thr Val Gly Val Ile Gly Thr Gly Arg Ile Gly Arg Ala Ala Ile
145                 150                 155                 160
Asp Ile Phe Lys Pro Phe Gly Ala Lys Val Ile Ala Tyr Asp Val Phe
                165                 170                 175
Arg Asn Pro Ala Leu Glu Lys Glu Gly Met Tyr Val Asp Thr Leu Glu
                180                 185                 190
Glu Leu Tyr Gln Gln Ala Asn Val Ile Thr Leu His Val Pro Ala Leu
                195                 200                 205
Lys Asp Asn Tyr His Met Leu Asp Glu Lys Ala Phe Gly Gln Met Gln
                210                 215                 220
Asp Gly Thr Phe Ile Leu Asn Phe Ala Arg Gly Thr Leu Val Asp Thr
225                 230                 235                 240
Pro Ala Leu Leu Lys Ala Leu Asp Ser Gly Lys Val Ala Gly Ala Ala
                245                 250                 255
Leu Asp Thr Tyr Glu Asn Glu Val Gly Ile Phe Asp Val Asp His Gly
                260                 265                 270
Asp Gln Pro Ile Asp Asp Pro Val Phe Asn Asp Leu Met Ser Arg Arg
                275                 280                 285
Asn Val Met Ile Thr Pro His Ala Ala Phe Tyr Thr Arg Pro Ala Val
                290                 295                 300
Lys Asn Met Val Gln Ile Ala Leu Asp Asn Asn Arg Asp Leu Ile Glu
305                 310                 315                 320
Lys Asn Ser Ser Lys Asn Glu Val Lys Phe Glu
                325                 330

<210> SEQ ID NO 28
<211> LENGTH: 44
<212> TYPE: DNA
<213> ORGANISM: Artificial Sequence
<220> FEATURE:
<223> OTHER INFORMATION: Synthesized

<400> SEQUENCE: 28

-continued

```
cactttttca aacatgaaaa ttattgctta tggcattcga gatg          44
```

<210> SEQ ID NO 29
<211> LENGTH: 50
<212> TYPE: DNA
<213> ORGANISM: Artificial Sequence
<220> FEATURE:
<223> OTHER INFORMATION: Synthesized

<400> SEQUENCE: 29

```
atcatcatca tccttgtaat cgtcaaactt aacttcattt tttgcagcac    50
```

<210> SEQ ID NO 30
<211> LENGTH: 331
<212> TYPE: PRT
<213> ORGANISM: Pediococcus pentosaceus
<220> FEATURE:
<223> OTHER INFORMATION: PpDLDH

<400> SEQUENCE: 30

```
Met Lys Ile Ile Ala Tyr Gly Ile Arg Asp Asp Glu Lys Thr Tyr Leu
              5                   10                  15

Glu Glu Trp Val Lys Asp Asn Lys Ile Glu Val Lys Ala Val Ser Glu
         20                  25                  30

Leu Leu Asp Ser Asn Thr Ile Glu Gln Ala Lys Gly Tyr Asp Gly Val
     35                  40                  45

Val Ala Tyr Gln Gln Lys Pro Tyr Thr Asp Asp Leu Phe Asp Lys Met
 50                  55                  60

Asn Glu Phe Gly Ile His Ala Phe Ser Leu Arg Asn Val Gly Val Asp
65                  70                  75                  80

Asn Val Pro Val Glu Ala Leu Lys Arg Asn Asn Ile Lys Ile Thr Asn
                 85                  90                  95

Val Pro Ala Tyr Ser Pro Met Ala Ile Ala Glu Leu Ser Val Thr Gln
            100                 105                 110

Leu Leu Ala Leu Ile Arg Arg Ile Pro Glu Phe Asp Ala Lys Met Ala
        115                 120                 125

Arg Gly Asp Phe Arg Trp Glu Pro Asp Ile Ala Leu Glu Leu Asn Gln
    130                 135                 140

Met Thr Val Gly Val Ile Gly Thr Gly Arg Ile Gly Arg Ala Ala Ile
145                 150                 155                 160

Asn Ile Phe Lys Gly Phe Gly Ala Lys Val Ile Ala Tyr Asp Val Phe
                165                 170                 175

Arg Asn Ser Glu Leu Glu Lys Glu Gly Ile Tyr Val Asp Ser Leu Glu
            180                 185                 190

Glu Leu Tyr Arg Gln Val Asp Val Ile Thr Leu His Val Pro Ala Leu
        195                 200                 205

Lys Asp Asn Tyr His Met Leu Asn Asp Glu Ala Phe Ala Gln Met His
    210                 215                 220

Asp Gly Val Phe Val Leu Asn Phe Ala Arg Gly Ser Leu Ile Asp Thr
225                 230                 235                 240

Lys Ala Leu Leu Lys Ala Leu Asp Ser Gly Lys Val Ala Gly Ala Ala
                245                 250                 255

Leu Asp Thr Tyr Glu Asp Glu Val Gly Val Phe Asp Val Asp His Gln
            260                 265                 270

Asn Asp Pro Ile Asn Asp Pro Val Phe Asn Asp Leu Tyr Ser Arg Arg
        275                 280                 285

Asn Val Lys Ile Thr Pro His Ala Ala Phe Tyr Thr Lys Pro Ala Val
```

```
                290                 295                 300
Lys Asn Met Val Gln Ile Ala Leu Glu Asn Asn Lys Ala Leu Ile Glu
305                 310                 315                 320

Lys Gly Ala Ala Lys Asn Glu Val Lys Phe Asp
                325                 330
```

<210> SEQ ID NO 31
<211> LENGTH: 44
<212> TYPE: DNA
<213> ORGANISM: Artificial Sequence
<220> FEATURE:
<223> OTHER INFORMATION: Synthesized

<400> SEQUENCE: 31 gacactttt caaacatgac taaaattttt gcttacgcaa ttcg         44

<210> SEQ ID NO 32
<211> LENGTH: 41
<212> TYPE: DNA
<213> ORGANISM: Artificial Sequence
<220> FEATURE:
<223> OTHER INFORMATION: Synthesized

<400> SEQUENCE: 32
gaaatcaact tttgttcgcc aaccttaact ggagtttcag c          41

<210> SEQ ID NO 33
<211> LENGTH: 333
<212> TYPE: PRT
<213> ORGANISM: Lactobacillus bulgaricus
<220> FEATURE:
<223> OTHER INFORMATION: LbDLDH

<400> SEQUENCE: 33

```
Met Thr Lys Ile Phe Ala Tyr Ala Ile Arg Glu Asp Glu Lys Pro Phe
                5                  10                  15

Leu Lys Glu Trp Glu Asp Ala His Lys Asp Val Glu Val Glu Tyr Thr
            20                  25                  30

Asp Lys Leu Leu Thr Pro Glu Thr Ala Ala Leu Ala Lys Gly Ala Asp
        35                  40                  45

Gly Val Val Val Tyr Gln Gln Leu Asp Tyr Thr Ala Glu Thr Leu Gln
    50                  55                  60

Ala Leu Ala Asp Asn Gly Ile Thr Lys Met Ser Leu Arg Asn Val Gly
65                  70                  75                  80

Val Asp Asn Ile Asp Met Ala Lys Ala Lys Glu Leu Gly Phe Gln Ile
                85                  90                  95

Thr Asn Val Pro Val Tyr Ser Pro Asn Ala Ile Ala Glu His Ala Ala
            100                 105                 110

Ile Gln Ala Ala Arg Ile Leu Arg Gln Ala Lys Ala Met Asp Glu Lys
        115                 120                 125

Val Ala Arg His Asp Leu Arg Trp Ala Pro Thr Ile Gly Arg Glu Val
    130                 135                 140

Arg Asp Gln Val Val Gly Val Val Gly Thr Gly His Ile Gly Gln Val
145                 150                 155                 160

Phe Met Gln Ile Met Glu Gly Phe Gly Ala Lys Val Ile Ala Tyr Asp
                165                 170                 175

Ile Phe Arg Asn Pro Glu Leu Glu Lys Lys Gly Tyr Tyr Val Asp Ser
            180                 185                 190

Leu Asp Asp Leu Tyr Lys Gln Ala Asp Val Ile Ser Leu His Val Pro
```

```
            195                 200                 205
Asp Val Pro Ala Asn Val His Met Ile Asn Asp Lys Ser Ile Ala Lys
    210                 215                 220

Met Lys Gln Asp Val Val Ile Val Asn Val Ser Arg Gly Pro Leu Val
225                 230                 235                 240

Asp Thr Asp Ala Val Ile Arg Gly Leu Asp Ser Gly Lys Val Phe Gly
                245                 250                 255

Tyr Ala Met Asp Val Tyr Glu Gly Glu Val Gly Val Phe Asn Glu Asp
                260                 265                 270

Arg Glu Gly Lys Glu Phe Pro Asp Ala Arg Leu Ala Asp Leu Ile Ala
            275                 280                 285

Arg Pro Asn Val Leu Val Thr Pro His Thr Ala Phe Tyr Thr Thr His
        290                 295                 300

Ala Val Arg Asn Met Val Val Lys Ala Phe Asp Asn Asn Leu Glu Leu
305                 310                 315                 320

Val Glu Gly Lys Glu Ala Glu Thr Pro Val Lys Val Gly
                325                 330
```

<210> SEQ ID NO 34
<211> LENGTH: 45
<212> TYPE: DNA
<213> ORGANISM: Artificial Sequence
<220> FEATURE:
<223> OTHER INFORMATION: Synthesized

<400> SEQUENCE: 34 gacactttt caaacatgaa aattattgct tatggcattc gtgac            45

<210> SEQ ID NO 35
<211> LENGTH: 45
<212> TYPE: DNA
<213> ORGANISM: Artificial Sequence
<220> FEATURE:
<223> OTHER INFORMATION: Synthesized

<400> SEQUENCE: 35
atcatcatca tccttgtaat cgtcgaacga gacttcgttt tcagc            45

<210> SEQ ID NO 36
<211> LENGTH: 332
<212> TYPE: PRT
<213> ORGANISM: Lactobacillus brevis
<220> FEATURE:
<223> OTHER INFORMATION: LbrDLDH

<400> SEQUENCE: 36

```
Met Lys Ile Ile Ala Tyr Gly Ile Arg Asp Asp Glu Gln Pro Tyr Leu
                5                  10                  15

Glu Gln Trp Ser Lys Asp Gln Gly Ile Glu Val Lys Ala Val Ala Glu
            20                  25                  30

Leu Leu Asp Glu Gln Thr Val Asp Leu Ala Lys Gly Tyr Asp Gly Ala
        35                  40                  45

Val Val Tyr Gln Gln Lys Pro Tyr Thr Ala Ala Val Leu Asp Gln Leu
    50                  55                  60

Ala Ala Asn Gly Val Thr Asn Leu Ser Leu Arg Asn Val Gly Val Asp
65                  70                  75                  80

Asn Val Asn Ala Asp Ala Val Lys Arg Asn Gly Phe Lys Val Thr Asn
                85                  90                  95

Val Pro Ala Tyr Ser Pro Ala Ala Ile Ala Glu Leu Thr Val Thr Gln
```

```
            100                 105                 110
Leu Met Arg Leu Leu Arg Arg Thr Pro Thr Phe Asp Arg Lys Gln Ala
                115                 120                 125
Gln Gly Asp Leu Thr Trp Ala Pro Asp Ile Ala Asp Glu Leu Asn Gln
            130                 135                 140
Met Thr Val Gly Ile Val Ala Thr Gly Arg Ile Gly Arg Ala Ala Met
145                 150                 155                 160
Arg Ile Tyr Gln Gly Phe Gly Ala Lys Val Ile Ala Tyr Asp Val Phe
                165                 170                 175
His Asn Pro Glu Leu Glu Lys Gln Gly Ile Tyr Val Asp Thr Leu Asp
            180                 185                 190
Glu Leu Tyr Ala Gln Ala Asp Val Ile Ser Leu His Ala Pro Ala Thr
                195                 200                 205
Lys Asp Asn Asp His Met Leu Asp Asp Ala Ala Phe Ala Lys Met Lys
            210                 215                 220
Asp Gly Val Trp Ile Leu Asn Pro Ala Arg Gly Ala Leu Ile Asp Thr
225                 230                 235                 240
Asp Ala Leu Ile Leu Ala Leu Asp Ser Gly Lys Val Ala Gly Ala Ala
                245                 250                 255
Leu Asp Val Tyr Glu Asp Glu Val Gly Ile Phe Asn Ala Asp Phe Lys
            260                 265                 270
Asn Phe Asp Ala Ile Pro Asp Glu Arg Leu Lys Asn Leu Met Lys Arg
            275                 280                 285
Glu Asn Val Leu Val Thr Pro His Ile Ala Phe Tyr Thr Lys Thr Ala
    290                 295                 300
Val Lys Asn Met Val Gln Phe Ala Leu Asn Asn Lys Gln Leu Ile
305                 310                 315                 320
Glu Thr Gly Arg Ala Glu Asn Glu Val Ser Phe Asp
                325                 330

<210> SEQ ID NO 37
<211> LENGTH: 46
<212> TYPE: DNA
<213> ORGANISM: Artificial Sequence
<220> FEATURE:
<223> OTHER INFORMATION: Synthesized

<400> SEQUENCE: 37 gacactttt caaacatgaa aattattgca tatgctgtac gtgatg                46

<210> SEQ ID NO 38
<211> LENGTH: 45
<212> TYPE: DNA
<213> ORGANISM: Artificial Sequence
<220> FEATURE:
<223> OTHER INFORMATION: Synthesized

<400> SEQUENCE: 38
atcatcatca tccttgtaat cgtcaaactt aacttgcgtg tcagc                 45

<210> SEQ ID NO 39
<211> LENGTH: 332
<212> TYPE: PRT
<213> ORGANISM: Lactobacillus pentosus
<220> FEATURE:
<223> OTHER INFORMATION: LpDLDH

<400> SEQUENCE: 39

Met Lys Ile Ile Ala Tyr Ala Val Arg Asp Asp Glu Arg Pro Phe Phe
```

```
            5                   10                  15
Asp Thr Trp Met Lys Glu Asn Pro Asp Val Glu Val Lys Leu Val Pro
             20                  25                  30

Glu Leu Leu Thr Glu Asp Asn Val Asp Leu Ala Lys Gly Phe Asp Gly
             35                  40                  45

Ala Asp Val Tyr Gln Gln Lys Asp Tyr Thr Ala Glu Val Leu Asn Lys
 50                  55                  60

Leu Ala Asp Glu Gly Val Lys Asn Ile Ser Leu Arg Asn Val Gly Val
 65                  70                  75                  80

Asp Asn Leu Asp Val Pro Thr Val Lys Ala Arg Gly Leu Asn Ile Ser
                 85                  90                  95

Asn Val Pro Ala Tyr Ser Pro Asn Ala Ile Ala Glu Leu Ser Val Thr
                100                 105                 110

Gln Leu Met Gln Leu Leu Arg Gln Thr Pro Met Phe Asn Lys Lys Leu
                115                 120                 125

Ala Lys Gln Asp Phe Arg Trp Ala Pro Asp Ile Ala Lys Glu Leu Asn
130                 135                 140

Thr Met Thr Val Gly Val Ile Gly Thr Gly Arg Ile Gly Arg Ala Ala
145                 150                 155                 160

Ile Asp Ile Phe Lys Gly Phe Gly Ala Lys Val Ile Gly Tyr Asp Val
                165                 170                 175

Tyr Arg Asn Ala Glu Leu Glu Lys Glu Gly Met Tyr Val Asp Thr Leu
                180                 185                 190

Asp Glu Leu Tyr Ala Gln Ala Asp Val Ile Thr Leu His Val Pro Ala
                195                 200                 205

Leu Lys Asp Asn Tyr His Met Leu Asn Ala Asp Ala Phe Ser Lys Met
210                 215                 220

Lys Asp Gly Ala Tyr Ile Leu Asn Phe Ala Arg Gly Thr Leu Ile Asp
225                 230                 235                 240

Ser Glu Asp Leu Ile Lys Ala Leu Asp Ser Gly Lys Val Ala Gly Ala
                245                 250                 255

Ala Leu Val Thr Tyr Glu Tyr Glu Thr Lys Ile Phe Asn Lys Asp Leu
                260                 265                 270

Glu Gly Gln Thr Ile Asp Asp Lys Val Phe Met Asn Leu Phe Asn Arg
                275                 280                 285

Asp Asn Val Leu Ile Thr Pro His Thr Ala Phe Tyr Thr Glu Thr Ala
                290                 295                 300

Val His Asn Met Val His Val Ser Met Asn Ser Asn Lys Gln Phe Ile
305                 310                 315                 320

Glu Thr Gly Lys Ala Asp Thr Gln Val Lys Phe Asp
                325                 330
```

<210> SEQ ID NO 40
<211> LENGTH: 42
<212> TYPE: DNA
<213> ORGANISM: Artificial Sequence
<220> FEATURE:
<223> OTHER INFORMATION: Synthesized

<400> SEQUENCE: 40 gacactttt caaacatggc aaaaatttac gcatacggaa tc          42

<210> SEQ ID NO 41
<211> LENGTH: 44
<212> TYPE: DNA
<213> ORGANISM: Artificial Sequence
<220> FEATURE:
<223> OTHER INFORMATION: Synthesized

<400> SEQUENCE: 41
atcatcatca tccttgtaat caccaacctt aactggggtt tcag                          44

<210> SEQ ID NO 42
<211> LENGTH: 332
<212> TYPE: PRT
<213> ORGANISM: Lactobacillus fermentum
<220> FEATURE:
<223> OTHER INFORMATION: LfDLDH

<400> SEQUENCE: 42

Met Ala Lys Ile Tyr Ala Tyr Gly Ile Arg Lys Asp Glu Pro Tyr
                 5                  10                  15

Leu Asn Glu Trp Ala Lys Asn His Ala Asp Val Thr Val Asp Tyr Thr
             20                  25                  30

Ala Glu Leu Leu Thr Pro Glu Thr Ala Gln Ala Ala Gly Ala Asp
             35                  40                  45

Gly Val Val Tyr Gln Gln Leu Asp Tyr Thr Ala Glu Thr Leu Gln
     50                  55                  60

Ala Leu Ala Asp Gln Gly Val Thr Lys Met Ser Leu Arg Asn Val Gly
65                  70                  75                  80

Ile Asp Asn Ile Asp Met Ala Lys Ala Lys Glu Leu Gly Phe Glu Ile
                 85                  90                  95

Thr Asn Val Pro Val Tyr Ser Pro Asn Ala Ile Ala Glu His Ala Ala
                100                 105                 110

Ile Gln Thr Ala Arg Ile Leu Arg Gln Ser Lys Lys Leu Asp Lys Lys
            115                 120                 125

Ile Glu Asn Gly Asp Leu Arg Trp Ala Pro Thr Ile Gly Arg Glu Val
        130                 135                 140

Arg Asp Gln Val Val Gly Val Val Gly Thr Gly His Ile Gly Gln Val
145                 150                 155                 160

Phe Met Gln Ile Met Glu Gly Phe Gly Ala Lys Val Ile Ala Tyr Asp
                165                 170                 175

Val Phe Lys Asp Pro Glu Leu Glu Lys Lys Gly Tyr Tyr Val Ser Leu
            180                 185                 190

Asp Glu Ile Tyr Ala Gln Ala Asp Val Ile Ser Leu His Val Pro Ala
        195                 200                 205

Leu Glu Ser Thr Ile His Met Ile Asn Asp Glu Thr Ile Ala Lys Met
    210                 215                 220

Lys Asp Asp Ala Val Leu Val Asn Val Ser Arg Gly Pro Leu Val Asp
225                 230                 235                 240

Thr Asp Ala Val Ile Arg Ala Leu Asp Ser Gly Lys Leu Phe Gly Phe
                245                 250                 255

Val Met Asp Thr Tyr Glu Asp Glu Val Gly Ile Phe Asn Glu Asp Trp
            260                 265                 270

Gln Gly Lys Glu Phe Pro Asp Ala Arg Leu Asn Asp Leu Ile His Arg
        275                 280                 285

Asp Asn Val Leu Val Thr Pro His Thr Ala Phe Tyr Thr Thr His Ala
    290                 295                 300

Val Arg Asn Met Val Leu Lys Ala Phe Asp Asn Asn Leu Ala Leu Val
305                 310                 315                 320

Lys Gly Glu Glu Pro Glu Thr Pro Val Lys Val Gly
                325                 330

<210> SEQ ID NO 43
<211> LENGTH: 46
<212> TYPE: DNA
<213> ORGANISM: Artificial Sequence
<220> FEATURE:
<223> OTHER INFORMATION: Synthesized

<400> SEQUENCE: 43 gacactttt caaacatgaa aattattgca tatgctgtac gtgatg        46

<210> SEQ ID NO 44
<211> LENGTH: 50
<212> TYPE: DNA
<213> ORGANISM: Artificial Sequence
<220> FEATURE:
<223> OTHER INFORMATION: Synthesized

<400> SEQUENCE: 44
atcatcatca tccttgtaat cgtcaaactt aacttgcgta tcagctttac        50

<210> SEQ ID NO 45
<211> LENGTH: 332
<212> TYPE: PRT
<213> ORGANISM: Lactobacillus plantarum
<220> FEATURE:
<223> OTHER INFORMATION: LplDLDH

<400> SEQUENCE: 45

Met Lys Ile Ile Ala Tyr Ala Val Arg Asp Asp Glu Arg Pro Phe Phe
1               5                   10                  15

Asp Thr Trp Met Lys Glu Asn Pro Asp Val Glu Val Lys Leu Val Pro
            20                  25                  30

Glu Leu Leu Thr Glu Asp Asn Val Asp Leu Ala Lys Gly Phe Asp Gly
        35                  40                  45

Ala Asp Val Tyr Gln Gln Lys Asp Tyr Thr Ala Glu Val Leu Asn Lys
    50                  55                  60

Leu Ala Asp Glu Gly Val Lys Asn Ile Ser Leu Arg Asn Val Gly Val
65                  70                  75                  80

Asp Asn Leu Asp Val Pro Thr Val Lys Ala Arg Gly Leu Asn Ile Ser
                85                  90                  95

Asn Val Pro Ala Tyr Ser Pro Asn Ala Ile Ala Glu Leu Ser Val Thr
            100                 105                 110

Gln Leu Met Gln Leu Leu Arg Gln Thr Pro Leu Phe Asn Lys Lys Leu
        115                 120                 125

Ala Lys Gln Asp Phe Arg Trp Ala Pro Asp Ile Ala Lys Glu Leu Asn
    130                 135                 140

Thr Met Thr Val Gly Val Ile Gly Thr Gly Arg Ile Gly Arg Ala Ala
145                 150                 155                 160

Ile Asp Ile Phe Lys Gly Phe Gly Ala Lys Val Ile Gly Tyr Asp Val
                165                 170                 175

Tyr Arg Asn Ala Glu Leu Glu Lys Glu Gly Met Tyr Val Asp Thr Leu
            180                 185                 190

Asp Glu Leu Tyr Ala Gln Ala Asp Val Ile Thr Leu His Val Pro Ala
        195                 200                 205

Leu Lys Asp Asn Tyr His Met Leu Asn Ala Asp Ala Phe Ser Lys Met
    210                 215                 220

Lys Asp Gly Ala Tyr Ile Leu Asn Phe Ala Arg Gly Thr Leu Ile Asp
225                 230                 235                 240

-continued

```
Ser Glu Asp Leu Ile Lys Ala Leu Asp Ser Gly Lys Val Ala Gly Ala
                245                 250                 255

Ala Leu Asp Thr Tyr Glu Tyr Glu Thr Lys Ile Phe Asn Lys Asp Leu
            260                 265                 270

Glu Gly Gln Thr Ile Asp Asp Lys Val Phe Met Asn Leu Phe Asn Arg
        275                 280                 285

Asp Asn Val Leu Ile Thr Pro His Thr Ala Phe Tyr Thr Glu Thr Ala
    290                 295                 300

Val His Asn Met Val His Val Ser Met Asn Ser Asn Lys Gln Phe Ile
305                 310                 315                 320

Glu Thr Gly Lys Ala Asp Thr Gln Val Lys Phe Asp
                325                 330
```

<210> SEQ ID NO 46
<211> LENGTH: 38
<212> TYPE: DNA
<213> ORGANISM: Artificial Sequence
<220> FEATURE:
<223> OTHER INFORMATION: Synthesized

<400> SEQUENCE: 46 gcacttttt caaacatgaa gatcattgcc tacggtgc                               38

<210> SEQ ID NO 47
<211> LENGTH: 38
<212> TYPE: DNA
<213> ORGANISM: Artificial Sequence
<220> FEATURE:
<223> OTHER INFORMATION: Synthesized

<400> SEQUENCE: 47
atcatcatca tccttgtaat ccttggcggg accggtga                              38

<210> SEQ ID NO 48
<211> LENGTH: 332
<212> TYPE: PRT
<213> ORGANISM: Lactobacillus casei
<220> FEATURE:
<223> OTHER INFORMATION: LcDLDH

<400> SEQUENCE: 48

```
Met Lys Ile Ile Ala Tyr Gly Ala Arg Val Asp Glu Ile Gln Tyr Phe
                5                  10                  15

Lys Gln Trp Ala Lys Asp Thr Gly Asn Thr Leu Glu Tyr His Thr Glu
            20                  25                  30

Phe Leu Asp Glu Asn Thr Val Glu Trp Ala Lys Gly Phe Asp Gly Ile
        35                  40                  45

Asn Ser Leu Gln Thr Thr Pro Tyr Ala Ala Gly Val Phe Glu Lys Met
    50                  55                  60

His Ala Tyr Gly Ile Lys Phe Leu Thr Ile Arg Asn Val Gly Thr Asp
65                  70                  75                  80

Asn Ile Asp Met Thr Ala Met Lys Gln Tyr Gly Ile Arg Leu Ser Asn
                85                  90                  95

Val Pro Ala Tyr Ser Pro Ala Ala Ile Ala Glu Phe Ala Leu Thr Asp
            100                 105                 110

Thr Leu Tyr Leu Leu Arg Asn Met Gly Lys Val Gln Ala Gln Leu Gln
        115                 120                 125

Ala Gly Asp Tyr Glu Lys Ala Gly Thr Phe Ile Gly Lys Glu Leu Gly
    130                 135                 140
```

Gln Gln Thr Val Gly Val Met Gly Thr Gly His Ile Gly Gln Val Ala
145                 150                 155                 160

Ile Lys Leu Phe Lys Gly Phe Gly Ala Lys Val Ile Ala Tyr Asp Pro
            165                 170                 175

Tyr Pro Met Lys Gly Asp His Pro Asp Phe Asp Tyr Val Ser Leu Glu
        180                 185                 190

Asp Leu Phe Lys Gln Ser Asp Ile Ile Asp Leu His Val Pro Gly Ile
            195                 200                 205

Glu Gln Asn Thr His Ile Ile Asn Glu Ala Ala Phe Asn Leu Met Lys
        210                 215                 220

Pro Gly Ala Ile Val Ile Asn Thr Ala Arg Pro Asn Leu Ile Asp Thr
225                 230                 235                 240

Gln Ala Met Leu Ser Asn Leu Lys Ser Gly Lys Leu Ala Gly Val Gly
            245                 250                 255

Ile Asp Thr Tyr Glu Tyr Glu Thr Glu Asp Leu Leu Asn Leu Ala Lys
            260                 265                 270

His Gly Ser Phe Lys Asp Pro Leu Trp Asp Glu Leu Leu Gly Met Pro
            275                 280                 285

Asn Val Val Leu Ser Pro His Ile Ala Tyr Tyr Thr Glu Thr Ala Val
        290                 295                 300

His Asn Met Val Tyr Phe Ser Leu Gln His Leu Val Asp Phe Leu Thr
305                 310                 315                 320

Lys Gly Glu Thr Ser Thr Glu Val Thr Gly Pro Ala
            325                 330

<210> SEQ ID NO 49
<211> LENGTH: 55
<212> TYPE: DNA
<213> ORGANISM: Artificial Sequence
<220> FEATURE:
<223> OTHER INFORMATION: Synthesized

<400> SEQUENCE: 49 gacactttt caaacatgta cataatcttt aatttcactc atttactttt caatc       55

<210> SEQ ID NO 50
<211> LENGTH: 48
<212> TYPE: DNA
<213> ORGANISM: Artificial Sequence
<220> FEATURE:
<223> OTHER INFORMATION: Synthesized

<400> SEQUENCE: 50
gagctcgaat tcacatgtta atttaaacgt gtttcacatg taccagtg              48

<210> SEQ ID NO 51
<211> LENGTH: 351
<212> TYPE: PRT
<213> ORGANISM: Schizosaccharomyces pombe
<220> FEATURE:
<223> OTHER INFORMATION: SaDLDH

<400> SEQUENCE: 51

Met Tyr Ile Ile Phe Asn Phe Thr His Leu Leu Phe Asn Leu Leu Lys
                5                   10                  15

Ala Arg Phe Leu Ile Met Thr Lys Ile Met Phe Phe Gly Thr Arg Asp
            20                  25                  30

Tyr Glu Lys Glu Met Ala Leu Asn Trp Gly Lys Lys Asn Asn Val Glu
        35                  40                  45

```
Val Thr Thr Ser Lys Glu Leu Leu Ser Ser Ala Thr Val Asp Gln Leu
 50                  55                  60

Lys Asp Tyr Asp Gly Val Thr Thr Met Gln Phe Gly Lys Leu Glu Asn
 65                  70                  75                  80

Asp Val Tyr Pro Lys Leu Glu Ser Tyr Gly Ile Lys Gln Ile Ala Gln
                 85                  90                  95

Arg Thr Ala Gly Phe Asp Met Tyr Asp Leu Asp Leu Ala Lys Lys His
                100                 105                 110

Asn Ile Val Ile Ser Asn Val Pro Ser Tyr Ser Pro Glu Thr Ile Ala
            115                 120                 125

Glu Tyr Ser Val Ser Ile Ala Leu Gln Leu Val Arg Arg Phe Pro Asp
        130                 135                 140

Ile Glu Arg Arg Val Gln Thr His Asp Phe Thr Trp Gln Ala Glu Ile
145                 150                 155                 160

Met Ser Lys Pro Val Lys Asn Met Thr Val Ala Ile Ile Gly Thr Gly
                165                 170                 175

Arg Ile Gly Ala Ala Thr Ala Lys Ile Tyr Ala Gly Phe Gly Ala Thr
                180                 185                 190

Ile Thr Ala Tyr Asp Ala Tyr Pro Asn Lys Asp Leu Asp Phe Leu Thr
            195                 200                 205

Tyr Lys Asp Ser Val Lys Glu Ala Ile Lys Asp Ala Asp Ile Ile Ser
        210                 215                 220

Leu His Val Pro Ala Asn Lys Glu Ser Tyr His Leu Phe Asp Lys Ala
225                 230                 235                 240

Met Phe Asp His Val Lys Lys Gly Ala Ile Leu Val Asn Ala Ala Arg
                245                 250                 255

Gly Ala Val Ile Asn Thr Pro Asp Leu Ile Ala Val Asn Asp Gly
                260                 265                 270

Thr Leu Leu Gly Ala Ala Ile Asp Thr Tyr Glu Asn Glu Ala Ala Tyr
        275                 280                 285

Phe Thr Asn Asp Trp Thr Asn Lys Asp Ile Asp Lys Thr Leu Leu
        290                 295                 300

Glu Leu Ile Glu His Glu Arg Ile Leu Val Thr Pro His Ile Ala Phe
305                 310                 315                 320

Phe Ser Asp Glu Ala Val Gln Asn Leu Val Glu Gly Gly Leu Asn Ala
                325                 330                 335

Ala Leu Ser Val Ile Asn Thr Gly Thr Cys Glu Thr Arg Leu Asn
            340                 345                 350

<210> SEQ ID NO 52
<211> LENGTH: 41
<212> TYPE: DNA
<213> ORGANISM: Artificial Sequence
<220> FEATURE:
<223> OTHER INFORMATION: Synthesized

<400> SEQUENCE: 52 gacactttt caaacatgaa gattttgct tacggcattc g                    41

<210> SEQ ID NO 53
<211> LENGTH: 45
<212> TYPE: DNA
<213> ORGANISM: Artificial Sequence
<220> FEATURE:
<223> OTHER INFORMATION: Synthesized

<400> SEQUENCE: 53
```
gagctcgaat tcacatgtta atattcaaca gcaatagctg gcttc            45

<210> SEQ ID NO 54
<211> LENGTH: 331
<212> TYPE: PRT
<213> ORGANISM: Leuconostoc mesenteroides
<220> FEATURE:
<223> OTHER INFORMATION: LmDLDH

<400> SEQUENCE: 54

Met Lys Ile Phe Ala Tyr Gly Ile Arg Asp Asp Glu Lys Pro Ser Leu
                 5                  10                  15

Glu Glu Trp Lys Ala Ala Asn Pro Glu Ile Glu Val Asp Tyr Thr Gln
             20                  25                  30

Glu Leu Leu Thr Pro Glu Thr Ala Lys Leu Ala Glu Gly Ser Asp Ser
         35                  40                  45

Ala Val Val Tyr Gln Gln Leu Asp Tyr Thr Arg Glu Thr Leu Thr Ala
     50                  55                  60

Leu Ala Asn Val Gly Val Thr Asn Leu Ser Leu Arg Asn Val Gly Thr
65                  70                  75                  80

Asp Asn Ile Asp Phe Asp Ala Ala Arg Glu Phe Asn Phe Asn Ile Ser
                 85                  90                  95

Asn Val Pro Val Tyr Ser Pro Asn Ala Ile Ala Glu His Ser Met Leu
            100                 105                 110

Gln Leu Ser Arg Leu Leu Arg Arg Thr Lys Ala Leu Asp Ala Lys Ile
        115                 120                 125

Ala Lys Arg Asp Leu Arg Trp Ala Pro Thr Thr Gly Arg Glu Met Arg
    130                 135                 140

Met Gln Thr Val Gly Val Ile Gly Thr Gly His Ile Gly Arg Val Ala
145                 150                 155                 160

Ile Asn Ile Leu Lys Gly Phe Gly Ala Lys Val Ile Ala Tyr Asp Lys
                165                 170                 175

Tyr Pro Asn Ala Glu Leu Gln Ala Glu Gly Leu Tyr Val Asp Thr Leu
            180                 185                 190

Asp Glu Leu Tyr Ala Gln Ala Asp Ala Ile Ser Leu Tyr Val Pro Gly
        195                 200                 205

Val Pro Glu Asn His His Leu Ile Asn Ala Asp Ala Ile Ala Lys Met
    210                 215                 220

Lys Asp Gly Val Val Ile Met Asn Ala Ala Arg Gly Asn Leu Met Asp
225                 230                 235                 240

Ile Asp Ala Ile Ile Asp Gly Leu Asn Ser Gly Lys Ile Ser Asp Phe
                245                 250                 255

Gly Met Asp Val Tyr Glu Asn Glu Val Ala Cys Ser Met Lys Ile Gly
            260                 265                 270

Leu Val Lys Asn Ser Pro Asp Ala Lys Ile Ala Asp Leu Ile Ala Arg
        275                 280                 285

Glu Asn Val Met Ile Thr Pro His Thr Ala Phe Tyr Thr Thr Lys Ala
    290                 295                 300

Val Leu Glu Met Val His Gln Ser Phe Asp Ala Val Ala Phe Ala
305                 310                 315                 320

Lys Gly Glu Lys Pro Ala Ile Ala Val Glu Tyr
                325                 330

<210> SEQ ID NO 55
<211> LENGTH: 1116

-continued

```
<212> TYPE: DNA
<213> ORGANISM: Schizosaccharomyces pombe
<220> FEATURE:
<223> OTHER INFORMATION: leu1 gene

<400> SEQUENCE: 55
atgtgtgcaa agaaaatcgt cgtcttacca ggagaccata ttggccctga aattgttgct      60
tctgccttgg aggttttgaa agtcgttgag aagaagcgac ctgagttaaa actcgagttt     120
gaagaacaca agattggagg tgcctctatt gatgcctatg aaccccttt gactgacgag      180
actgtgaagg cttgtttgga agctgacggt gttcttttgg gtgccgttgg tggtcctgaa     240
tggaccaacc ccaattgtcg tcctgagcaa ggtttattga agcttcgtaa gagtatgggt     300
gtttgggcca accttcgacc ttgcaacttt gccagcaagt ctttagtcaa gtacagccct     360
ttgaagcctg aaatcgttga aggtgtcgat ttttgtgttg tacgagaact tactggaggt     420
tgttactttg gtgagcgcac tgaggacaac ggatcgggtt atgctatgga cacttggcct     480
tacagtttgg aagaagtttc tcgtattgct cgtttggctg cttggttagc tgaaacttcc     540
aaccctcctg ctcccgtcac attactcgac aaagctaatg ttttggcaac ttctcgtctt     600
tggcgcaaga ctgtagctaa gattttaag gaggaatatc ctcaccttac cttaaaaaac      660
cagctcattg actccgcagc catgcttttg gtcaagagcc ctcgtacact aacggtgtt     720
gttttgactg acaacttgtt tggtgacatt atttcagatg aggcttctgt cattcctggt     780
agcttgggcc ttttgccttc tgcctccctt tccggtgtgg taggaaaatc agaagaaaag     840
gttcattgtt tggttgagcc cattcacggt agcgctcccg atatcgctgg caagggcatt     900
gttaatcctg ttggtacaat tttatctgct tcccttctcc ttcgttatgg tttgaatgct     960
cctaaggagg ctgaagctat cgaagccgcc gtacgcaagg tcttggatga tacttcaatt    1020
ggtggacgtg gtctttatac tcgcgatttg ggaggtgagg cttctaccgc tgatattact    1080
aaggctgttg ttgaagaact tgaaaaaatt ttgtaa                              1116

<210> SEQ ID NO 56
<211> LENGTH: 795
<212> TYPE: DNA
<213> ORGANISM: Schizosaccharomyces pombe
<220> FEATURE:
<223> OTHER INFORMATION: Ura4 gene

<400> SEQUENCE: 56
atggatgcta gagtatttca aagctattca gctagagctg aggggatgaa aaatcccatt      60
gccaaggaat tgttggcttt gatggaagaa agcaaagca acttgtcagt cgcggtcgat     120
ttgacgaaga atccgaaat cttagaattg gtagataaaa ttggacccta tgtctgtgtt     180
atcaagacac atattgacgt tgtcgaggat ttcgaccagg atatggtaga aaaactggtg     240
gccttaggta aaaagcatcg ttttcttatc tttgaggatc gcaaattcgc agacattgga     300
aataccgtca gctacaata tgcatctggt gtgtacaaaa ttgcttcttg ggctcatatc     360
acaaattgcc atacagtgcc aggcgagggt attatacaag gcctcaaaga agttggttta     420
cctttgggac gtggtctctt gcttttggct gaaatgtctt ccaaaggctc tttggctact     480
ggttcctaca cagagaaaac cttagaatgg tttgagaagc ataccgattt ttgctttggc     540
tttatagctg tcgtcgatt tcctaacctt caaagcgact acataactat gtcccctggt     600
atcggcttgg atgttaaagg agacgggctg ggacagcaat atcgtactcc tgaagaagtg     660
attgtaaact gcggtagcga tatcatcatt gttggtcgtg gagtctatgg agctggtcgt     720
```

```
aatcctgttg tcgaagccaa gagatataga gaagctggtt ggaaggcata tcagcaaaga    780
ctttctcagc attaa                                                    795
```